(12) United States Patent
Huysseune et al.

(10) Patent No.: US 11,867,685 B2
(45) Date of Patent: Jan. 9, 2024

(54) OLFACTORY RECEPTOR INVOLVED IN THE PERCEPTION OF MUSK FRAGRANCE AND THE USE THEREOF

(71) Applicant: CHEMCOM S.A., Brussels (BE)

(72) Inventors: Sandra Huysseune, Brussels (BE); Alex Veithen, Genappe (BE); Yannick Quesnel, Wavre (BE)

(73) Assignee: CHEMCOM S.A., Brussels (BE)

( * ) Notice: Subject to any disclaimer, the term of this patent is extended or adjusted under 35 U.S.C. 154(b) by 548 days.

(21) Appl. No.: 16/770,457

(22) PCT Filed: Dec. 5, 2018

(86) PCT No.: PCT/EP2018/083570
§ 371 (c)(1),
(2) Date: Jun. 5, 2020

(87) PCT Pub. No.: WO2019/110630
PCT Pub. Date: Jun. 13, 2019

(65) Prior Publication Data
US 2021/0164967 A1 Jun. 3, 2021

(30) Foreign Application Priority Data
Dec. 5, 2017 (EP) .................................... 17205402

(51) Int. Cl.
*G01N 33/50* (2006.01)
(52) U.S. Cl.
CPC ................................ *G01N 33/5008* (2013.01)
(58) Field of Classification Search
None
See application file for complete search history.

(56) References Cited

FOREIGN PATENT DOCUMENTS

| WO | WO 01/02551 A2 | 1/2001 |
| --- | --- | --- |
| WO | WO 01/27158 A2 | 4/2001 |
| WO | WO 2006/094704 A2 | 9/2006 |
| WO | WO 2014/191047 A1 | 2/2014 |
| WO | WO 2015/020158 A1 | 2/2015 |
| WO | WO 2016/201152 A1 | 12/2016 |

OTHER PUBLICATIONS

Malnic, B., et al. 2004 (PNAS 101(8): 2584-2589. (Year: 2004).*
GenBank: DAA04706.1 TPA_inf: olfactory receptor OR11-248, 2004. (Year: 2004).*
Liu, J., et al. 2020 Synlett 31: 972-976. (Year: 2020).*
Database UniProt, XP002788018, retrieved from EBI accession No. UNIPROT: Q96R48 Database accession No. Q96R48, 2003.
International Preliminary Report On Patentability, dated Nov. 28, 2019, in International Application No. PCT/EP2018/083570.
International Search Report With Written Opinion dated Apr. 3, 2019, in International Application No. PCT/EP2018/083570.
Krautwurst et al., Identification Of Ligands For Olfactory Receptors By Functional Expression Of A Receptor, Cell, vol. 95, pp. 917-926, 1998.
Sato-Akuhara et al., Ligand Specificity and Evolution of Mammalian Musk Odor Receptors: Effect of Single Receptor Deletion on Odor Detection, Journal Of Neuroscience, vol. 36, No. 16, pp. 4482-4491, 2016.
Shirasu et al., Olfactory Receptor And Neural Pathway Responsible For Highly Selective Sensing Of Musk Odors, Neuron, vol. 81, pp. 165-178, 2013.
Trimmer et al., Genetic Variation Across The Human Olfactory Receptor Repertoire Alters Odor Perception, BioRxiv, 22 pages, 2017.
Adipietro et al., Functional Evolution of Mammalian Odorant Receptors, PLOS Genetics, vol. 8, Issue 7, pp. 1-14, e1002821, 2012.
Bird, Monitoring Phospholipid Signaling Pathways: Recipes from the Experts, TEM, vol. 9, No. 9, pp. 384-386, 1998.
Detheux et al., Natural Proteolytic Processing of Hemofiltrate CC Chemokine 1 Generates a Potent CC Chemokine Receptor (CCR)1 and CCR5 Agonist with Anti-HIV Properties, J. Exp. Med., vol. 192, No. 10, pp. 1501-1508, 2000.
Fujita et al., Deorphanization of Dresden G Protein-Coupled Receptor for an Odorant Receptor, Journal of Receptors and Signal Transduction, vol. 27, pp. 323-334, 2007.
Hubbard et al., Externally Disposed Plasma Membrane, The Journal of Cell Biology, vol. 64, pp. 461-479, 1975.
Horton et al., Mass Measurements of Cyclic AMP Formation by Radioimmunoassay, Enzyme Immunoassay and Scintillation Proximity Assay, Methods in Molecular Biology, vol. 41, pp. 91-105, 1995.
Jaeger et al., A Mendelian Trait for Olfactory Sensitivity Affects Odor Experience and Food Selection, Current Biology, vol. 23, pp. 1601-1605, 2013.
Keller et al., Genetic variation in a human odorant receptor alters odour perception, Nature, vol. 449, pp. 468-472, 2007.
Kenimer et al., Desensitization of Adenylate Cyclase to Prostaglandin $E_1$ or 2-Chloroadenosine, Molecular Pharmacology, vol. 20, pp. 585-591, 1981.
Kikkawa et al., Calcium-activated, Phospholipid-dependent Protein Kinase from Rat Brain, The Journal of Biological Chemistry, Vo. 257, No. 22, pp. 13341-13348, 1982.
Matarazzo et al., Functional Characterization of Two Human Olfactory Receptors Expressed in the Baculovirus Sf9 Insect Cell System, Chem. Senses, vol. 30, pp. 195-207, 2005.
McLintok et al., In Vivo Identification of Eugenol-Responsive and Muscone-Responsive Mouse Odorant Receptors, The Journal of Neuroscience, vol. 34, No. 47, pp. 15669-15678, 2014.
Mirzabekov et al., Paramagnetic proteoliposomes containing a pure, native, and oriented seven-transmembrane segment protein, CCR5, Nature Biotechnology, vol. 18, pp. 649-654, 2000.

(Continued)

*Primary Examiner* — Marsha Tsay
(74) *Attorney, Agent, or Firm* — Knobbe, Martens, Olson & Bear LLP

(57) ABSTRACT

The invention relates to the identification of OR5A2 as an Olfactory Receptor that binds natural musk and synthetic musks. The invention encompasses the use of the interaction of OR5A2 polypeptides and nitromusk, polycyclic musk, macrocyclic musk and alicyclic musks as the basis of screening assays for agents that specifically modulate the activity of the OR of the invention.

19 Claims, 21 Drawing Sheets
Specification includes a Sequence Listing.

(56) References Cited

OTHER PUBLICATIONS

Office Action dated Dec. 6, 2022 in Japanese Application No. 530474-2020.
Pinna et al., How do protein Kinases recognize their substrates?, Biochemicia et Biophyica Acta, vol. 1314, pp. 191-225, 1996.
Rudolph et al., Expression, Characterization, and Mutagenesis of the *Yersinia pestis* Murine Toxin, a Phospholipase D Superfamily Member, The Journal of Biological Chemistry, vol. 274, No. 17, pp. 11824-11831, 1999.
Sanz et al., Comparison of Odorant Specificity of Two Human Olfactory Receptors from Different Phylogenetic Classes and Evidence for Antagonism, Chem. Senses, vol. 30, pp. 69-80, 2005.
Saito et al., RTP Family Members Induce Functional Expression of Mammalian Odorant Receptors, Cell, vol. 119, pp. 679-691, 2004.
Saito et al., Odor Coding by a Mammalian Receptor Repertoire, Sci Signal, vol. 2, No. 60, pp. 1-14, 2009.
Salamon et al., Surface Plasmon Resonance Spectroscopy Studies of Membrane Proteins: Transducin Binding and Activation by Rhodopsin Monitored in Thin Membrane Films, Biophysical Journal, vol. 71, pp. 283-294, 1996.
Salamon et al., Plasmon resonance spectroscopy: probing molecular interactions within membranes, TIBS 24, pp. 213-219, 1999.
Salamon et al., Optical Anisotropy in Lipid Bilayer Membranes: Coupled Plasmon-Waveguide Resonance Measurements of Molecular Orientation, Polarizability, and Shape, Biophysical Journal, vol. 80, pp. 1557-1567, 2001.
Sarrio et al., The Heat Shock Cognate Protein hsc73 Assembles with A1 Adenosine Receptors To Form Functional Modules in the Cell Membrane, Mol. Cell. Biol., vol. 20, No. 14, pp. 5164-5174, 2000.
Shirasu et al., Olfactory Receptor and Neural Pathway Responsible for Highly Selective Sensing of Musk Odors, Neuron, vol. 81, pp. 165-178, 2014.
Shirokova et al., Identification of Specific Ligands for Orphan Olfactory Receptors G Protein-Dependent Agonism and Antagonism of Odorants, The Journal of Biological Chemistry, vol. 280, No. 12, pp. 11807-11815, 2005.
Schmeideberg et al., Structural determinants of odorant recognition by the human olfactory receptors OR1A1 and OR1A2, Journal of Structural Biology, vol. 159, pp. 400-412, 2007.
Spehr et al., Identification of a Testicular Odorant Receptor Mediating Human Sperm Chemotaxis, Science, vol. 299, 2054-2058, 2003.
Stables et al., A Bioluminescent Assay for Agonist Activity at Potentially Any G-Protein-Coupled Receptor, Analytical Biochemistry, vol. 252, pp. 115-126, 1997.
The Human Olfactory Data Explorer, https://genome.weizmann.ac.il/horde/, retrieved on Nov. 15, 2022.
Wetzel et al., Specificity and Sensitivity of a Human Olfactory Receptor Functionally Expressed in Human Embryonic Kidney 293 Cells and *Xenopus laevis* Oocytes, The Journal of Neuroscience, vol. 19, No. 17, pp. 7426-7433, 1999.
Yoshikawa et al., Diverse yet selective tuning of an odorant receptor for sensing four classes of musk compounds, Research Square, pp. 1-22, doi: https//doi.org/10.21203/rs.3.rs-1916850/v1, 2022.

* cited by examiner

Figure 1 A.
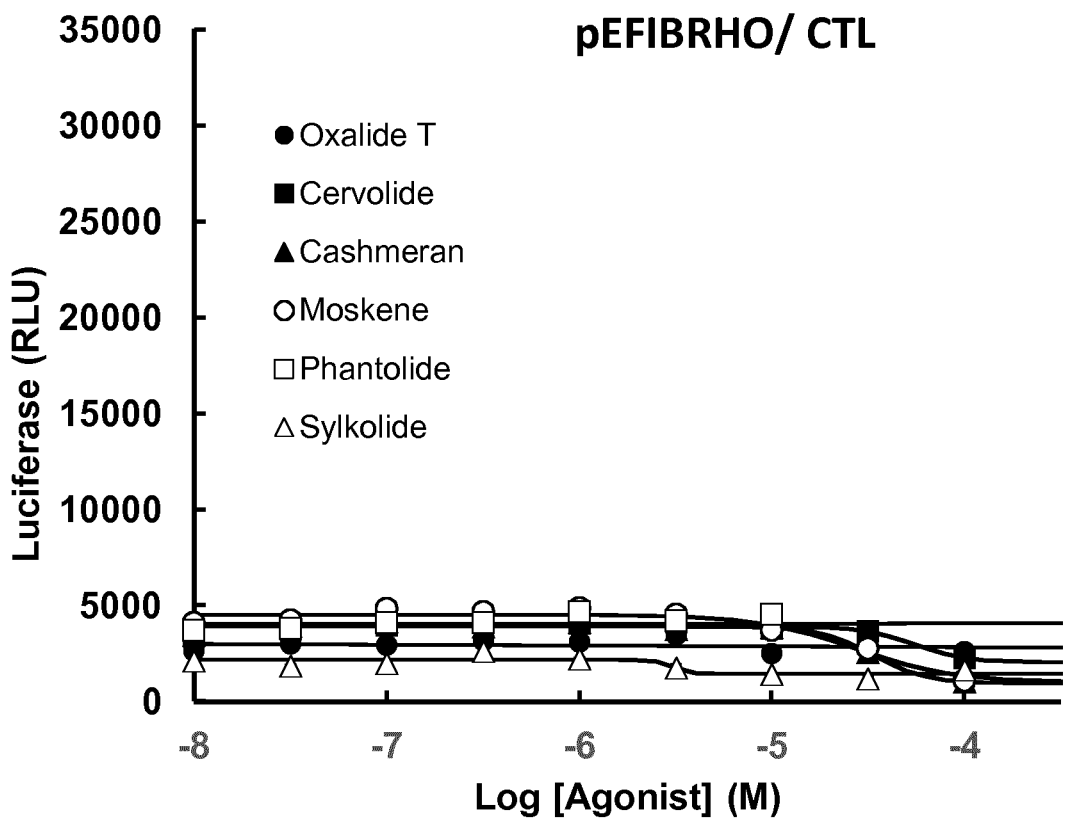
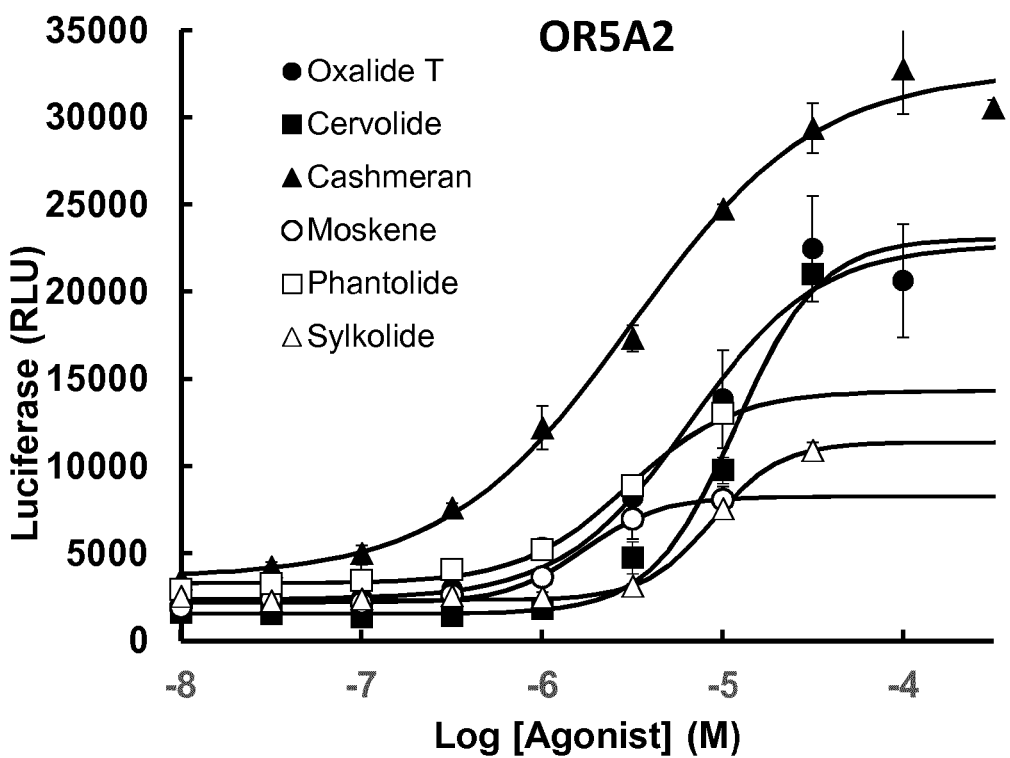

Figure 1 B.
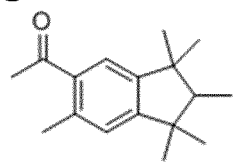
Phantolide
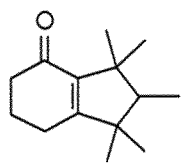
Cashmeran
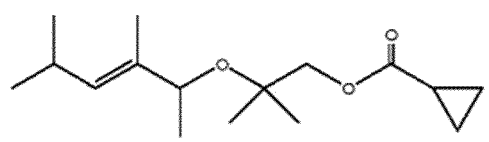
Sylkolide
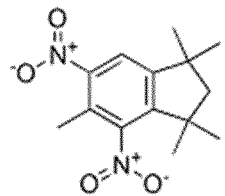
Moskene
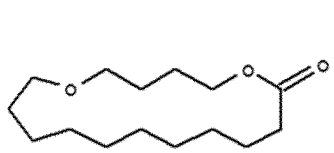
Cervolide
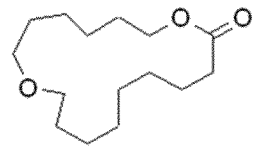
Oxalide T

Figure 2 A.

```
                        *        20         *        40         *
OR5A2_V1  : MAVGR--NNTIVTKFILLGLSDHPQMKIFLFMLFLGLYLLTLAWNLSLIA :  48
OR5A2_V2  : MAVGR--NNTIVTKFILLGLSDHPQMKIFLFMLFLGLYLLTLAWNLSLIA :  48
OR5A1     : MSITKAWNSSSVTMFILLGFTDHPELQALLFVTFLGIYLTTLAWNLALIF :  50
OR5AN1    : MTGGG--NITEITYFILLGFSDFPRIIKVLFTIFLVIYITSLAWNLSLIV :  48
OR11A1    : MEIVS-TGNETITEFVLLGFYDIPELHFLFFIVFTAVYVFIIIGNMLIIV :  49
            M      n    6T F6LLG  D P  6   1F  Fl  6Y6   6awN6 6I

60        *        80         *       100
OR5A2_V1  : LIKMDSHLHMPMYFFLSNLSFLDICYVSSTAPKMLSDIITEQKTISFVGC :  98
OR5A2_V2  : LIKMDSHLHMPMYFFLSNLSFLDICYVSSTAPKMLSDIITEQKTISFVGC :  98
OR5A1     : LIRGDTHLHTPMYFFLSNLSFIDICYSSAVAPNMLTDFFWEQKTISFVGC : 100
OR5AN1    : LIRMDSHLHTPMYFFLSNLSFIDVCYISSTVPKMLSNLLQGQQTITFVGC :  98
OR11A1    : AVVSSQRLHKPMYIFLANLSFLDILYTSAVMPKMLEGFLQEA-TISVAGC :  98
            l6   d  hLH PMYfFLsNLSF6D6cY S   PkML    eq TI3fvGC

*       120         *       140         *
OR5A2_V1  : ATQYFVFCGMGLTECFLLAAMAYDRYAAICNPLLYTVLISHTLCLKMVVG : 148
OR5A2_V2  : ATQYFVFCGMGLTECFLLAAMAYDRYAAICNPLLYTVLISHTLCLKMVVG : 148
OR5A1     : AAQFFFFVGMGLSECLLLTAMAYDRYAAISSPLLYPTIMTQGLCTRMVVG : 150
OR5AN1    : IIQYFIFSTMGLSESCLMTAMAYDRYAAICNPLLYSSIMSPTLCVWMVLG : 148
OR11A1    : LLQFFIFGSLATAECLLLAVMAYDRYLAICYPLHYPLLMGPRRYMGLVVT : 148
              Q5F F   6gl Ec L6 aMAYDRYaAIc PLlY   66   lc   6V6g

160        *       180         *       200
OR5A2_V1  : AYVGGFLSSFIETYSVYQHDFCGPYMINHFFCDLPPVLALSCSDTFTSEV : 198
OR5A2_V2  : AYVGGFLSSFIETYSVYQHDFCGLYMINHFFCDLPPVLALSCSDTFTSEV : 198
OR5A1     : AYVGGFLSSLIQASSIFRLHFCGPNIINHFFCDLPPVLALSCSDTFLSQV : 200
OR5AN1    : AYMTGLTASLFQIGALLQLHFCGSNVIRHFFCDMPQLLILSCTDTFFVQV : 198
OR11A1    : TWLSGFVVDGLVVALVAQLRFCGPNHIDQFYCDFMLFVGLACSDPRVAQV : 198
            a56 Gf  s      6 q  FCG    I hF5CD p  6 LsC3Dtf   2V

*       220         *       240         *
OR5A2_V1  : VTFIVSVVVGIVSVLVVLISYGYIVAAVVKISSATGRTKAFSTCASHLTA : 248
OR5A2_V2  : VTFIVSVVVGIVSVLVVLISYGYIVAAVVKISSATGRTKAFSTCASHLTA : 248
OR5A1     : VNFLVVVTVGGTSFLQLLISYGYIVSAVLKIPSAEGRWKACNTCASHLMV : 250
OR5AN1    : MTAILTMFFGIASALVIMISYGYIGISIMKITSAKGRSKAFNTCASHLTA : 248
OR11A1    : TTLILSVFCLTIPFGLILTSYARIVVAVLRVPAGASRRRAFSTCSSHIAV : 248
              t 66 6    g   s l 66iSYgyIv a6646 sa gR 4Af TCaSHL

260        *       280         *       300
OR5A2_V1  : VTLFYGSGFFMYMRPSSSYSLNRDKVVSIFYALVIPVVNPIIYSFRNKEI : 298
OR5A2_V2  : VTLFYGSGFFMYMRPSSSYSLNRDKVVSIFYALVIPVVNPIIYSFRNKEI : 298
OR5A1     : VTLLFGTALFVYLRPSSSYLLGRDKVVSVFYSLVIPMLNPLIYSLRNKEI : 300
OR5AN1    : VSLFYTSGIFVYLSSSGGSSSFDRFASVFYTVVIPMLNPLIYSLRNKEI : 298
OR11A1    : VTTFYGTLMIFYVAPSAVHSQLLSKVFSLLYTVVTPLFNPVIYTMRNKEV : 298
            V3lf5g3   f Y6 pSs   s    d4v S6fY 6ViP6 NP6IY3 RNKE6

*       320
OR5A2_V1  : KNAMRKAMERDPGISHGGPFIFMTLG : 324
OR5A2_V2  : KNAMRKAMERDPGISHGGPFIFMTLG : 324
OR5A1     : KDALWKVLERKKVFS----------- : 315
OR5AN1    : KDALKRLQKRKCC------------- : 311
OR11A1    : HQALRKILCIKQTETLD--------- : 315
            k A6 4    r
```

```
                Distance Matrix

```
CLUSTAL O(1.2.4) multiple sequence alignment

1: OR5A2_variant_1_P172
2: OR5A2_variant_2_P172L

1: MAVGRNNTIVTKFILLGLSDHPQMKIFLFMLFLGLYLLTLAWNLSLIALIKMDSHLHMPM 60
2: MAVGRNNTIVTKFILLGLSDHPQMKIFLFMLFLGLYLLTLAWNLSLIALIKMDSHLHMPM 60
   ************************************************************

1: YFFLSNLSFLDICYVSSTAPKMLSDIITEQKTISFVGCATQYFVFCGMGLTECFLLAAMA 120
2: YFFLSNLSFLDICYVSSTAPKMLSDIITEQKTISFVGCATQYFVFCGMGLTECFLLAAMA 120
   ************************************************************

1: YDRYAAICNPLLYTVLISHTLCLKMVVGAYVGGFLSSFIETYSVYQHDFCGPYMINHFFC 180
2: YDRYAAICNPLLYTVLISHTLCLKMVVGAYVGGFLSSFIETYSVYQHDFCGLYMINHFFC 180
   **************************************************** *******

1: DLPPVLALSCSDTFTSEVVTFIVSVVVGIVSVLVVLISYGYIVAAVVKISSATGRTKAFS 240
2: DLPPVLALSCSDTFTSEVVTFIVSVVVGIVSVLVVLISYGYIVAAVVKISSATGRTKAFS 240
   ************************************************************

1: TCASHLTAVTLFYGSGFFMYMRPSSSYSLNRDKVVSIFYALVIPVVNPIIYSFRNKEIKN 300
2: TCASHLTAVTLFYGSGFFMYMRPSSSYSLNRDKVVSIFYALVIPVVNPIIYSFRNKEIKN 300
   ************************************************************

1: AMRKAMERDPGISHGGPFIFMTLG 324
2: AMRKAMERDPGISHGGPFIFMTLG 324
   ************************
```

Figure 6 A.

```
                    *         20         *         40         *
OR5A2    : MAVGRNNTIVTKFILLGLSDHPQMKIELFMLELGLYLLTIAWNLSLIPLI  : 50
chimeric : --MTRNQTWVTDFILLGFPLSLRIQMLLSGLFSLLYVFTLLCNGAILGLI  : 48
             N T VT FILLG        L  LF LY  TL  N      LI 60        *         80        *        100
OR5A2    : KMDSLHMPMYFFLSNLSFLDICYVSSTAPKMLSDIITEQKTISFVGCAT  : 100
chimeric : WIDSRLHTPMYFFLSNLSFLDICYVSSTAPKMLSDIITEQKTISFVGCAT  : 98
             DS LH PMYFFLSNLSFLDICYVSSTAPKMLSDIITEQKTISFVGCAT

*        120         *        140         *
OR5A2    : QYFVFCGMGLTECFLLAAMAYDRYAAICNPLLYTVLISHTLCLKMVVGAY  : 150
chimeric : QYFVFCGMGLTECFLLAAMAYDRYAAICNPLLYTVLISHTLCLKMVVGAY  : 148
           QYFVFCGMGLTECFLLAAMAYDRYAAICNPLLYTVLISHTLCLKMVVGAY 160         *        180         *        200
OR5A2    : VGGFLSSFIETYSVYQHDFCGPYMINHFFCDLPPVLALSCSDTFTSEVVT  : 200
chimeric : VGGFLSSFIETYSVYQHDFCGPYMINHFFCDLPPVLALSCSDTFTSEVVT  : 198
           VGGFLSSFIETYSVYQHDFCGPYMINHFFCDLPPVLALSCSDTFTSEVVT

*        220         *        240         *
OR5A2    : FIVSVVVGIVSVLVVLISYGYIVAAVVKISSATGRTKAFSTCASHLTAVT  : 250
chimeric : FIVSVVVGIVSVLVVLISYGYIVAAVVKISSATGRTKAFSTCASHLTAVT  : 248
           FIVSVVVGIVSVLVVLISYGYIVAAVVKISSATGRTKAFSTCASHLTAVT 260         *        280         *        300
OR5A2    : LFYGSGFFMYMRPSSSYSLNRDKVVSIFYALVIPVVNPIIYSRRNKETKN  : 300
chimeric : LFYGSGFFMYMRPSSSYSLNRDKVVSIFYALVIPVVNPLIYSLRNABVKG  : 298
           LFYGSGFFMYMRPSSSYSLNRDKVVSIFYALVIPVVNP IYS RN E K

*        320
OR5A2    : AMRKAMERDPGISHGGPFIFMTLG          : 324
chimeric : ALKRVLWKQRSK------------          : 310
           A
```

Figure 6 B.
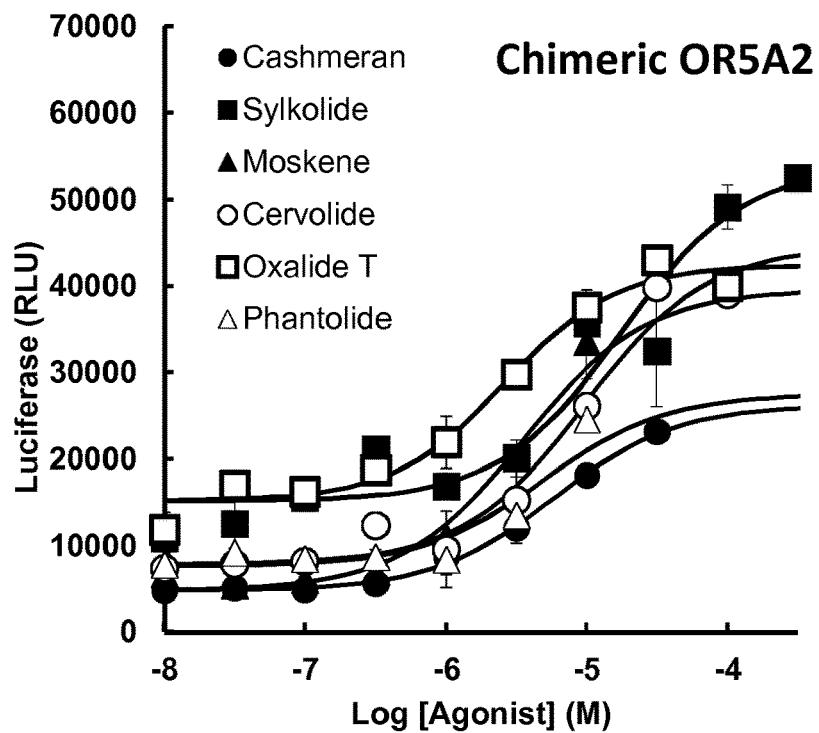
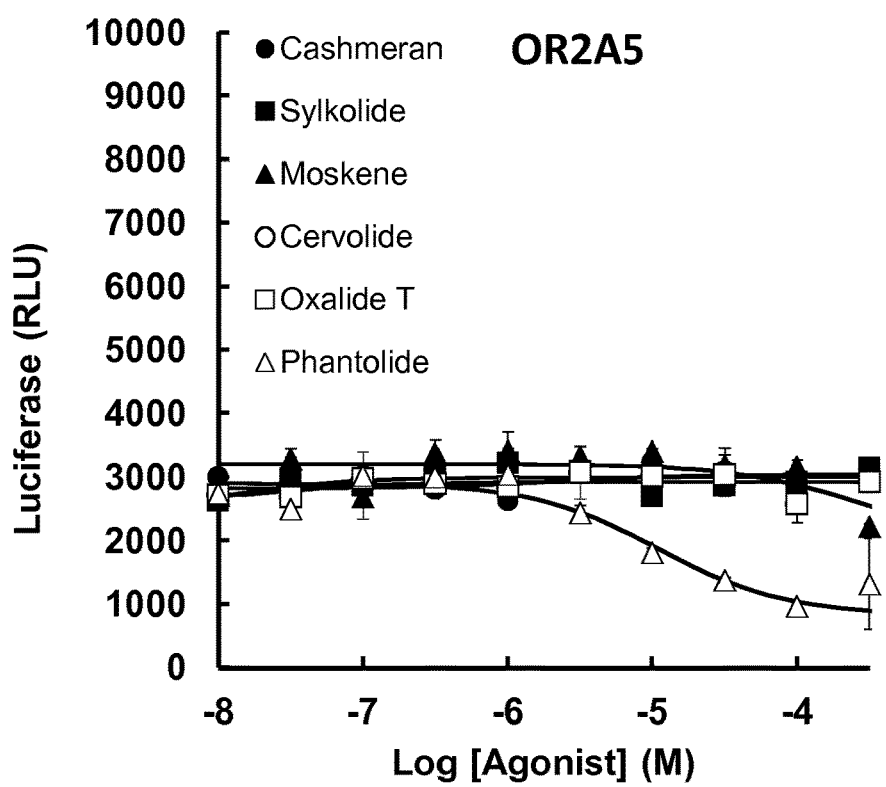

Figure 6 C.
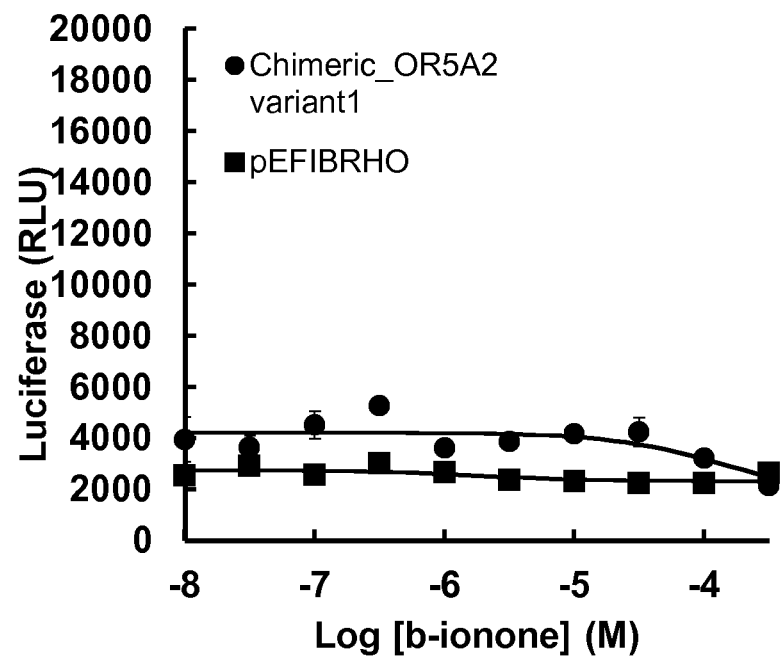
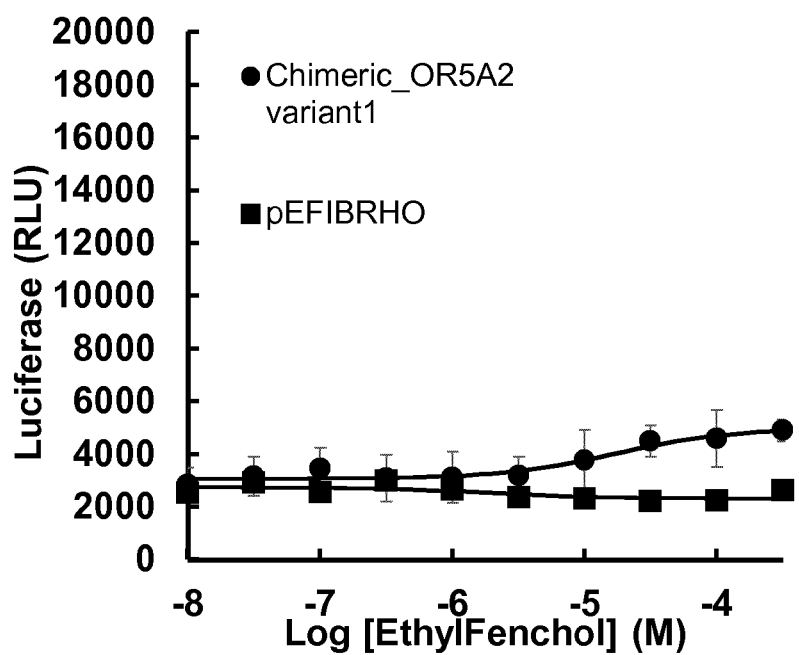

Figure 9
A.
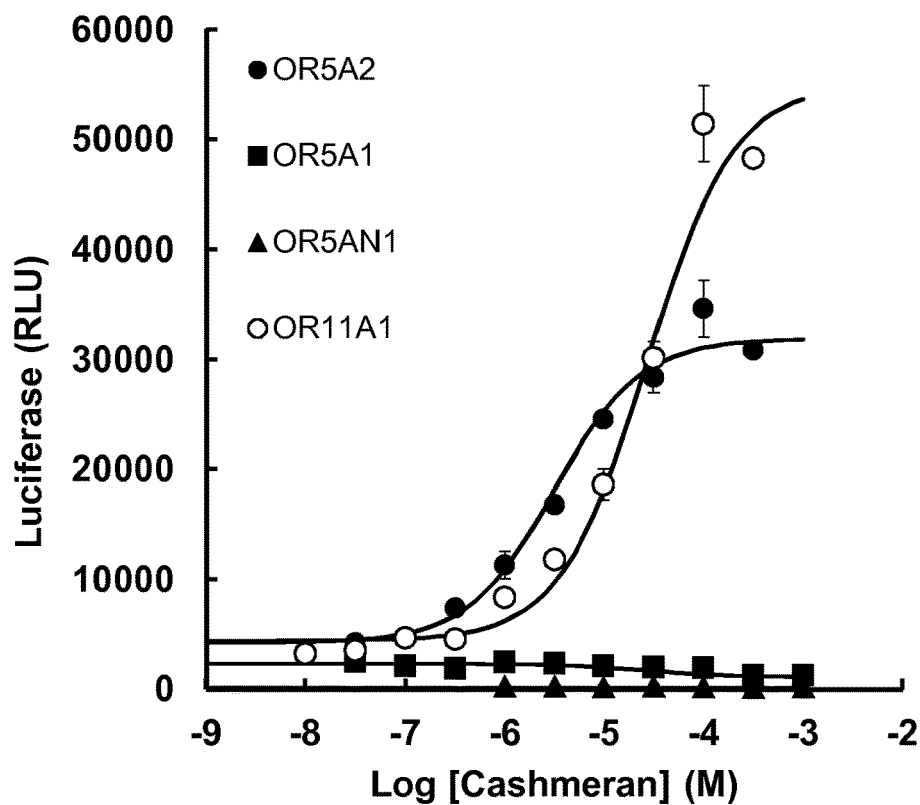
B.
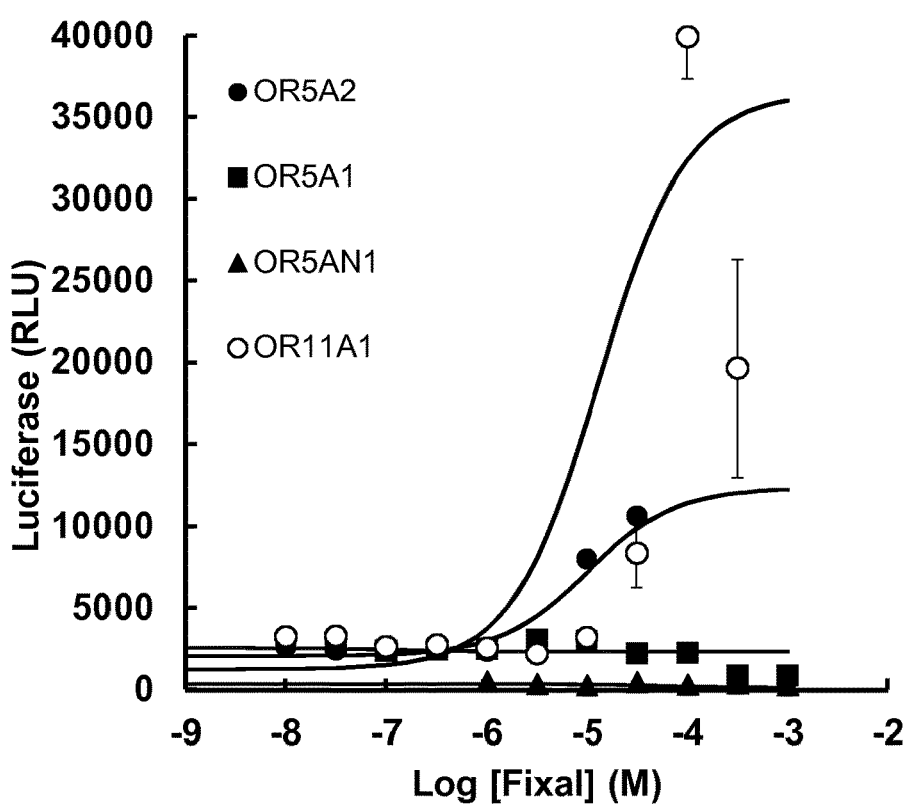

Figure 10
A.
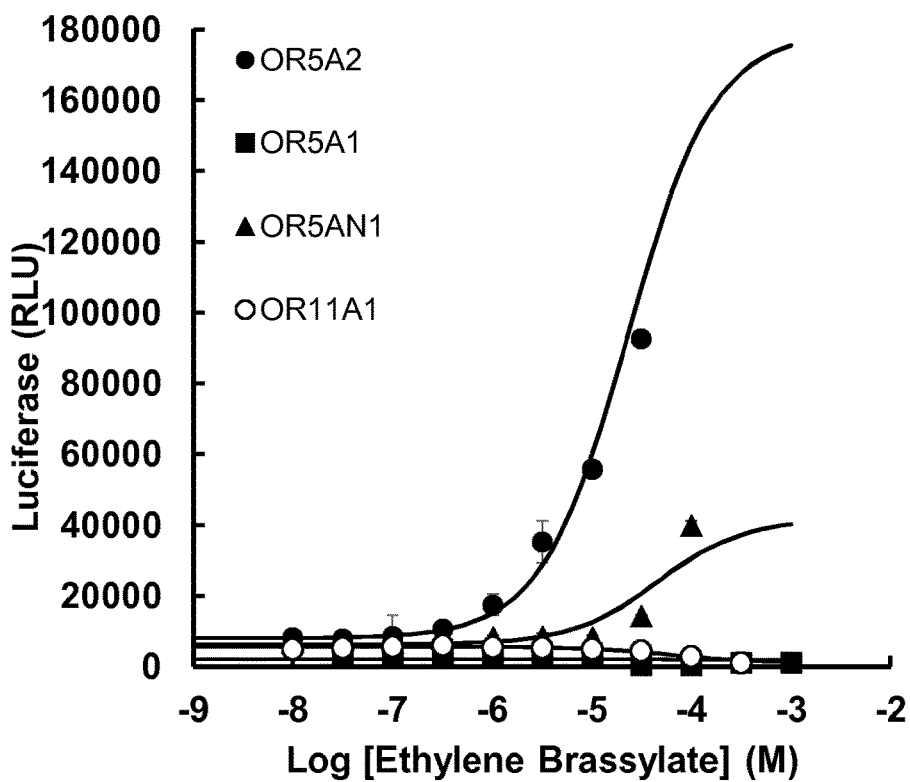
B.
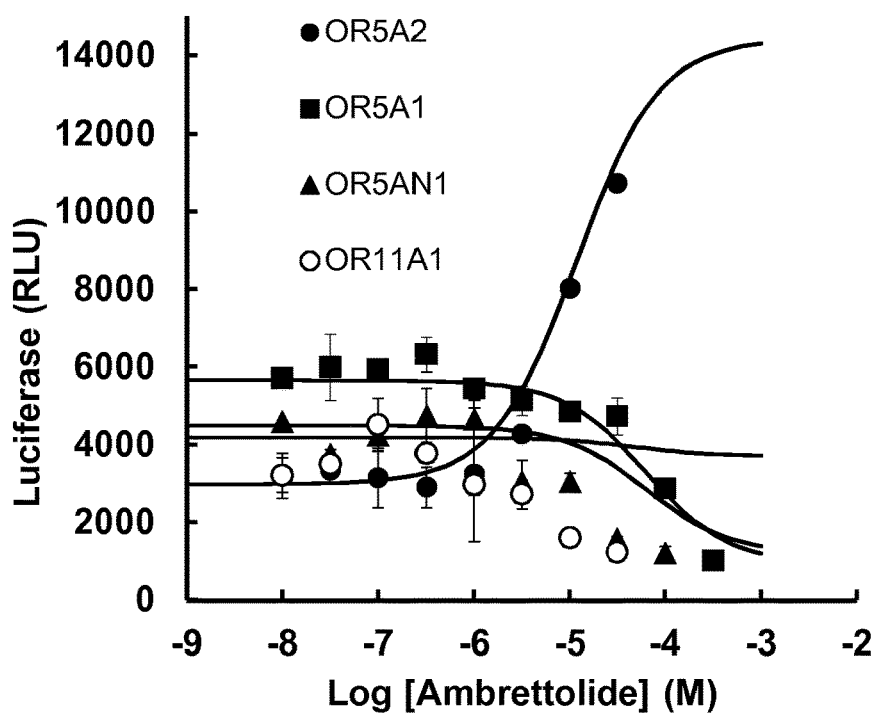

# OLFACTORY RECEPTOR INVOLVED IN THE PERCEPTION OF MUSK FRAGRANCE AND THE USE THEREOF

PRIORITY AND CROSS REFERENCE TO RELATED APPLICATIONS

This application is the U.S. National Stage Application under 35 U.S.C. § 371 of International Application No. PCT/EP2018/083570, filed Dec. 5, 2018, designating the U.S. and published in English as WO 2019/110630 A1 on Jun. 13, 2019, which claims the benefit of European Patent Application No. EP 17205402.5, filed Dec. 5, 2017. Any and all applications for which a foreign or a domestic priority is claimed is/are identified in the Application Data Sheet filed herewith and is/are hereby incorporated by reference in their entirety under 37 C.F.R. § 1.57.

SEQUENCE LISTING IN ELECTRONIC FORMAT

The present application is being filed along with an Electronic Sequence Listing as an ASCII text file via EFS-Web. The Electronic Sequence Listing is provided as a file entitled DECLE242001APCSEQLIST.txt, created on Jun. 3, 2020, and last modified on Jun. 4, 2020, which is 25,019 bytes in size. The information in the Electronic Sequence Listing is incorporated herein by reference in its entirety.

FIELD OF THE INVENTION

The technical field refers to the characterization of olfactory receptors. In particular, the present invention relates to the olfactory receptor five subfamily A member two, i.e. OR5A2 and the identification of its ligands corresponding to natural musk or synthetic musks. The present invention provides assays and methods of screening that can be used to identify compounds able to activate, mimic, block, inhibit, modulate and/or enhance the activity of this receptor (OR5A2).

BACKGROUND OF THE INVENTION

Olfactory Receptors

The genes coding for olfactory receptors (ORs) represent the largest family of genes (3% of the whole genome) in the human body dedicated to a single physiological function. These ORs belong to the superfamily of G protein coupled receptors (GPCRs). GPCRs are membrane receptors usually located at the surface of many different cell types. The common features of these receptors consist in seven transmembrane spans that form a barrel within the cell membrane and in their capacity to interact with heterotrimeric GTPase and thereby transducing a signal upon binding of their activators.

In the human genome, about 1.000 sequences containing characteristic signatures of olfactory receptors have been found. However, 60% of these appear to encode non-functional pseudogenes, thereby leaving humans with about 400 different functional OR proteins.

Based on phylogenetic analyses, the mammalian ORs can be classified into two different groups: class I and class II. The class 1 ORs, also called "fish-like receptors", forms a homogenous group that is more closely related to ORs found in fish and are therefore assumed to represent a conserved relic maintained throughout the evolution of the vertebrates. The persistence of this group of ancestral ORs suggests that they play an important role in mammalian chemical perception. In contrast to the fish-like ORs, the class 2 ORs first appeared in tetrapode vertebrates and expanded to form the majority of the OR repertoire presently known in humans. The class 2 ORs probably represents an adaptation to the terrestrial life where the detection of airborne odorant is required. In mammals the majority of the ORs belong to class II, but mammals do also have class I ORs.

Mechanisms of Odor Perception.

Odorant receptors are expressed in specialized olfactory sensory neurons (OSNs) located at the top of the nasal cavity in a small area that constitutes the olfactory epithelium. Filiform extensions at one end of these cells contain the ORs on their surface and float in the nasal mucus where the odorants are dissolved. At the opposite end, the OSN extends its axon across the ethmoid bone at the base of the cranium to connect to the olfactory bulb a small region of the brain dedicated to the integration of the olfactory stimuli. An outstanding feature of the tens of millions of OSN scattered throughout the olfactory epithelium is that each one expresses only one of the about 400 OR genes available in the human genome. In OSN, triggering of the OR promotes the activation of an olfactory-specific G protein (Galpha-olf) that stimulates a type III adenylate cyclase to produce cyclic AMP; this plays the role of a second messenger. Upon binding to a cAMP-gated cation channel, this messenger induces the entry of calcium into the cell. Calcium causes the opening of another channel that promotes the exit of chloride ions, and hence triggers an action potential of the neuron leading to a signal to the respective brain area. Each OR is able to interact with different molecules, and each odorant molecule can activate more than one OR. Thus, odor perception does not rely on the simple activation of a single OR, but rather on multiple activations of several ORs. With a pool of roughly 400 ORs, the number of possible combinations is almost infinite, thus explaining the outstanding discrimination properties of the olfactory system.

Characterization of Odorant Molecules with ORs

Cultured cell lines have been widely used to characterize and study receptors of interest in both academic and industrial contexts. This approach involves introduction of the corresponding gene into the cells, and subsequent promotion of its stable or transient overexpression. The activity of the receptor can be monitored using a functional assay. The use of easy-to-culture cell lines along with easy-to perform functional assays facilitates several thousand measurements per day. Typically, in the pharmaceutical industry, it is common to test libraries of million compounds per day on non-olfactory receptors. The production of cAMP arising in the cell upon activation of the OR by its odorant molecules may be detected by an indirect approach that consists of the use of a reporter gene, as described in (Saito et al., 2004 *Cell* Vol. 119, 679-691). This gene is placed under the control of a cAMP inducible promoter and is expressed only upon induction by cAMP. Different genes can be used for this purpose, but one of the most popular encodes the light-producing protein luciferase. While cleaving its substrate, luciferin, this enzyme releases light that is readily detected and quantified. The intensity of light emitted reflects the amount of luciferase produced, which is proportional to the cAMP increase and therefore directly related to the activity of the receptor. One of the advantages of reporter gene assays is dependent upon the signal amplification between receptor activation and reporter production. This makes the assay particularly sensitive to weak responses that can hardly be detected by other functional assays.

Other functional assays have also been used to demonstrate the activation of an OR by its odorant ligand. One of these assays consists in monitoring the increase in cytosolic calcium that occurs upon activation of the receptor (Krautwurtz D. et al. 1998. *Cell* 95, 917-26).

Identifications of human OR activators have also been reported. Examples of deorphanized human OR are given in Fujita Y et al. 2007. *J. Recept Signal. Transduct. Res.* 27, 323-34; Keller A. et al. 2007. *Nature* 449, 468-72; Matarazzo V. et al. 2005. *Chem. Senses* 30, 195-207; Saito H. et al. 2009. *Sci. Signal.* 2, 1-14; Sanz G. et al. 2005. *Chem. Senses* 30, 69-80; Schmiedeberg K. et al. 2007. *J Struct. Biol.* 159, 400-12.; Shirokova E. et al. 2004. *J. Biol. Chem.* 280, 11807-15.; Spehr M. et al. 2003. *Science* 299, 2054-58.; Wetzel, K. et al. 1999. *J. Neurosci.* 19, 7426-33; WO 2006/094704; Shirasu et al. 2014 *Neuron* 81, 165-78.

For several of the receptors, more than one ligand has been identified. Odorant activating the same OR can belong to different odorant families such as alcohol, aldehyde, esters, etc (Sanz G. et al. 2005. *Chem. Senses* 30, 69-80; Saito H. et al. 2009. *Sci. Signal.* 2, 1-14).

Musks

Musks are known to have been used in medicine and as fragrance for over 5000 years because of their fascinating scent and physiological effects. Nowadays, musk odors are widely used in cosmetic and perfume industry because of their warmth, elegance and animal scent as well as for their fixative properties.

The first natural musk compound, Muscone, was reported in 1906 by Walbaum as the major fragrant present in secretions of musk deer. Muscone presents a unique macrocyclic ketone structure with a 15-membered ring and has female attractive properties suggesting that it's male pheromone in musk deer. Since then, numerous compounds with a musky-like aroma have been purified from plants and animals like civet cat, musk shrew and muskarat. However, their physiological functions in these species have not been investigated.

In the past, musk deer was the principal source of natural musk used in the manufacturing of aromatic substances. Its rarity and high price presented an incentive for replacing natural musks with synthetic musks long before the issue of musk deer species conservation; which has later become a priority concern. The first synthetic musk compound, the "nitromusk", appeared in the 19th century by accident: Albert Baur, who wanted to find a way to get a powerful and safe explosive such as trinitrotoluene (TNT), obtained, instead, a strong musk-smelling substance. Since then, many compounds that mimic the aroma of Muscone have been synthetized and used in perfumery as base notes of many commercial formulations. These compounds are part of four structurally diverse groups of chemicals: nitromusks, polycyclic musks, macrocyclic musks, and linear/alicyclic musks.

Nitromusks belong to the nitrophenyl derivatives, which are technically easy to manufacture. They were the first generation of synthetic musks, and were massively used in perfumery until the 1950s. Nitromusks generally refer to the five most commercially relevant fragrant compounds: musk ketone (4-tert-butyl-2,6-dimethyl-3,5-dinitroacetophenone), musk ambrette (2,6-dinitro-3-methoxy-4-tert-butyltoluene), musk moskene (1,1,3,3,5-pentamethyl-4,6-dinitro-2H-indene), musk tibetene (1-tert-butyl-3,4,5-trimethyl-2,6-dinitrobenzene) and musk xylene (1-tert-butyl-3,5-dimethyl-2,4,6-trinitrobenzene). In this family, musk ketone was used in famous expensive perfumes such as Chanel no 5 and was considered as the benchmark smell of musk, since it closely resembles muscone. Since 1995, musk ambrette was banned by law in cosmetics by the European Union because of its photo-allergenic, carcinogenic and neurotoxic effects. Musk tibetene and musk moskene production has decreased in recent years due to concerns about their toxicity, bioaccumulation and persistence in the environment, and the resulting European Union ban on use of these musks in cosmetics. Musk Ketone and musk xylene continue to be used as additives in detergents, housecleaning products and other fragrant non-cosmetic products. Due to the fact that consumers did like the sweet powdery nitromusk smell and that some legendary fragrances were built upon nitromusks, scientists had to find some replacement for nitromusks.

In the 1950s, polycyclic musks were developed based on petrochemical-based materials. Structurally, they are formed by a bi-cyclic core structure such as indane or tetraline type, which is substituted with a combination of an acetyl group or a pyran ring in combination with methyl, isopropyl and/or t-butyl groups. The big advantages of this family are to be more stable, less reactive for functional use in perfumery and cheaper than nitromusks. Their high fixative effect as well as strong musky smell, sweet, with dry powdery and amber odor contribute to their success. The most widely used polycyclic musk is Galaxolide® followed by Tonalide®, are the two largest volume products in the group of polycyclic musks, representing about 95% of the EU market. Due to these high amounts produced and consumed as well as to their high bio-persistence, these substances are, nowadays, ubiquitous. Indeed, they can be detected in various environmental and human samples such as water, blood, breast milk, sediments and organisms such as various fish species. Moreover, they present a high level of lipophilicity and accumulate easily in fatty tissues causing modification of the chain food. As for nitromusks, the safety of the intake of these substances, not only via dermal contact, is under discussion, even although some animal studies and bio assays suggest yet that Galaxolide® may have hormone disrupting effects.

A third group of synthetic musk substitutes, macrocyclic musks, was synthetized in 1926. These molecules are very similar to those of natural musk and are clearly superior, in terms of odor characteristics, to other artificial musks. All members of this class possess at least a single ring composed of more than 6 carbons (often 10-15). In the past, owing to the relatively high cost of production, they were less extensively used in perfume formulation except for very exclusive composition. Although there remains very little information available on macrocyclic musks, these compounds appear to be more environment friendly. Moreover, up to now, no reports have demonstrated any adverse effect of macrocyclic musk on human health. For these reasons, we observe that the worldwide production of synthetic macrocyclic musks tends to increase currently.

Alicyclic musks, otherwise known as cycloalkyl ester or linear musks, are a relatively novel class of musk compounds with a structure dramatically different (modified alkyl esters) with respect to others musks previously described. The first compound of this class was introduced 1975 with Cyclomusk, having a warm, powdery, musky smell with hints of fruit and strawberries. This compound never entered on the market due to its uncompetitive price. Some years later, Helvetolide, a new compound of this class was produced at a commercial scale. Romandolide, a more ambrette and less fruity alicyclic musk compared to Helvetolide was introduced ten years later. The use of these musks is still very limited and they have been detected in some surface water. In general, little is known about these musks and considerations similar to those at polycyclic musks can be drawn. However, according different studies, Romandolide is readily biodegradable, therefore it is currently not expected to find linear musks at detectable levels in the environment.

Musk is a whole class of fragrant substances used as base notes in perfumery. Since the use of synthetic nitro- and polycyclic musks was reduced in recent years because of their health and environment damaging properties, it remains the most commonly used raw material present in almost all fragrant compositions. Its unique properties to balance the composition, to add a subtle touch of sensuality and warmth and to reduce the evaporation rate, make it a crucial, indispensable component in perfume industry. Hence, there is a real need for the development and the identification of new biodegradable, non-toxic musks or compounds that enhance the perception of these. Different strategies/methods have been developed in the past to find the musk fragrance or compound that activates, mimics, bloks, inhibits, modulates or enhances musk perception (Akuhara et al. 2016 *J Neurosci*. 36(16), 4482-91; Shirasu et al. 2014 *Neuron* 81, 165-78; WO 2016/201152A1; WO 2015/020158 A1). They are all based on the use of the two identified olfactory receptors in mice, olfr1440 (MOR215-1) or olfr96 (MOR221-1) and their human orthologs OR11A1 or OR5AN1 as musk-specific receptors.

SUMMARY OF THE INVENTION

In the present invention, it has surprisingly been discovered that an olfactory receptor, belonging to class 2 of OR, is activated by the four different structurally diverse groups of musks previously described. So far, none of the formerly identified musk-receptors showed such levels of responsiveness for the all four groups. Given the importance of musk in our everyday life, this unexpected discovery would allow the identification of musk compounds more safe, ecologically benign and useful for the perfumer and flavors companies.

The present invention relates to the identification of a new Olfactory Receptor (OR) belonging to class 2 of OR, namely, OR5A2 (the OR of the invention), as natural receptor for all structurally diverse group of chemicals comprising nitromusks, polycyclic musks, macrocyclic musks and linear musks. Preferably, the OR5A2 is defined herein by the amino acid sequence of SEQ ID NO:2 or polypeptide sequences having at least 80, preferably at least 85% or 86% amino acid identity, and more preferably 90%, 95%, 96%, 97%, 98%, 99% or higher, including 100% amino acid identity to SEQ ID NO:2, that are able to be activated by musk compounds. The invention encompasses the use of the interaction of these OR polypeptides and musk compounds as the basis of screening assays for agents that activate, mimic, block, inhibits, modulate or enhance the activity of the OR5A2 receptor as defined herein.

The invention further provides a chimeric receptor that comprises the central region of OR5A2, encompassing the transmembrane domains 2 to 7, defined by amino acid SEQ ID NO:11, which is fused at its N-terminus to the N-terminal extracellular moiety, the transmembrane domain 1 and the intracellular loop 1, of a G protein coupled receptor; and which is fused at its C-terminus to the intracellular C-terminal end of a G protein receptor. In preferred embodiments, said G protein coupled receptor is an olfactory receptor or the OR2A5 receptor defined by SEQ ID NO:12. Also provided is the use of such a chimeric receptor for identifying modulators of OR5A2 and the use of the central region of OR5A2, encompassing the transmembrane domains 2 to 7, defined by amino acid SEQ ID NO:11 or a polypeptide sequence having at least 95% amino acid identity, and preferably 96%, 97%, 98%, 99% or higher, including 100% amino acid identity, to SEQ ID NO:11, for identifying agents that interfere with the binding between said OR5A2 receptor and musk compounds.

The invention also encompasses kits for performing screening methods based upon the interaction of the OR5A2 receptor (SEQ ID NO:2) or the central region (transmembrane region 2 to 7—SEQ ID NO:11) of the OR5A2 receptor as defined herein with musk compounds.

The invention encompasses a method of identifying an agent or a sample, containing one or more agents, that modulates the activity of OR5A2 receptor as defined herein, said method comprising: a) contacting the OR polypeptide as defined herein, which can either be the OR5A2 receptor as defined herein (SEQ ID NO:2), its central region (SEQ ID NO:11), or a chimeric receptor comprising said central region (cf. for example SEQ ID NO:10), with an agent or a sample; b) measuring a signaling activity of said OR polypeptide in the presence of said agent or sample; and c) comparing the activity measured in the presence of said agent or sample to the activity measured in a reaction in which said OR polypeptide is contacted with one or more musk compound(s) at its/their $EC_{50}$, wherein said agent or sample is identified as an agent or a sample, that modulates the activity of the OR5A2 receptor as defined herein when the amount of the activity measured in the presence of the agent or sample is at least 10% of the amount induced by said musk compound(s) at its/their $EC_{50}$.

The invention further encompasses a method of identifying an agent or a sample, containing one or more agents, that modulates the activity of the OR5A2 receptor as defined herein, said method comprising: a) contacting said OR polypeptide with one or more musk compound(s) as defined herein in the presence and in the absence of an agent or sample; and b) measuring a signaling activity of the OR polypeptide as defined herein, which can either be the OR5A2 receptor as defined herein (SEQ ID NO:2), its central region (SEQ ID NO:11), or a chimeric receptor comprising said central region, and c) comparing the amount of said activity measured in a reaction containing said OR polypeptide and musk compound(s) without the agent or sample to the amount of said activity measured in a reaction containing said OR polypeptide, musk compound and said agent or sample, wherein a change in the activity in the presence of the agent or sample relative to the activity in the absence of the agent or sample, identifies said agent or sample as an agent or sample, that modulates the activity of the OR5A2 receptor as defined herein.

The invention further encompasses a method of identifying an agent or a sample, containing one or more agents, that increases the activity of the OR5A2 receptor as defined herein, said method comprising: a) contacting the OR polypeptide as defined herein, which can either be the OR5A2 receptor as defined herein (SEQ ID NO:2), its central region (SEQ ID NO:11), or a chimeric receptor comprising said central region, with one or more musk compound(s) as defined herein in the presence and in the absence of an agent or sample, under conditions permitting activation of said OR polypeptide by said musk compound(s); and b) measuring a signaling activity of said OR polypeptide, wherein a change in the activity in the presence of said agent or sample relative to the activity in the absence of said agent or sample identifies said agent or sample as an agent or sample, that increases the activity of the OR5A2 receptor as defined herein.

The invention further encompasses a method of identifying an agent or a sample, containing one or more agents, that decreases the activity of the OR5A2 receptor as defined herein, said method comprising: a) contacting the OR polypeptide as defined herein, which can either be the OR5A2 receptor as defined herein (SEQ ID NO:2), its central region (SEQ ID NO:11), or a chimeric receptor comprising said central region, with one or more musk compound(s) as defined herein in the presence and in the absence of an agent or sample, under conditions permitting activation of said OR polypeptide by said musk compound(s); and b) measuring a signaling activity of said OR polypeptide, wherein a change in the activity in the presence of said agent or sample relative to the activity in the absence of said agent or sample identifies said agent or sample as an agent or a sample that decreases the activity of the OR5A2 receptor as defined herein.

The invention encompasses a method of identifying an agent or a sample, containing one or more agents, that modulates the activity of the OR5A2 receptor as defined herein, said method comprising: a) contacting the OR polypeptide as defined herein, which can either be the OR5A2 receptor as defined herein (SEQ ID NO:2), its central region (SEQ ID NO:11), or a chimeric receptor comprising said central region, with an agent or sample; b) measuring the binding the said agent or sample to the said OR polypeptide; and c) comparing the binding of the said agent or sample to the binding of the said OR polypeptide to one or more musk compound(s) as defined herein at its/their $EC_{50}$, wherein said agent or sample is identified as an agent or a sample that modulates the activity of the OR5A2 receptor as defined herein when the amount of the binding of said agent or sample is at least 10% of the amount binding of said musk compound(s) present at its/their $EC_{50}$.

The invention further encompasses a method of identifying an agent, or a sample containing one or more agents, that modulates the interaction between one or more musk compound(s) as defined herein and the OR5A2 receptor as defined herein, said method comprising: a) contacting the OR polypeptide as defined herein, which can either be the OR5A2 receptor as defined herein (SEQ ID NO:2), its central region (SEQ ID NO:11), or a chimeric receptor comprising said central region, with said musk compound(s) in the presence and absence of an agent or sample under conditions permitting the binding of said musk compound(s) to said OR polypeptide; and b) measuring the binding of the OR polypeptide to said musk compound(s), wherein a modulation in binding in the presence of the agent or sample, relative to the binding in the absence of the agent or sample, identifies said agent or sample as an agent or a sample that modulates the interaction between one or more musk compound(s) as defined herein and the OR5A2 receptor as defined herein.

According to the present invention, when using binding methods, the one or more musk compound(s) may be detectably labeled. In said methods, the musk compound(s) may be detectably labeled with a moiety selected from the group consisting of a radioisotope, a fluorophore, and a quencher of fluorescence.

In one embodiment of any one of the preceding methods, the contacting is performed in or on a cell expressing the OR polypeptide as defined herein, which can either be the OR5A2 receptor as defined herein (SEQ ID NO:2), its central region (SEQ ID NO:11), or a chimeric receptor comprising said central region. According to the present invention, said cell may be, but is not limited to, Human embryonic kidney cells (HEK293), Chinese hamster cells (CHO), Monkey cells (COS), primary olfactory cells, *Xenopus* cells, insect cells, yeast or bacteria.

In another embodiment of any one of the preceding methods, the contacting is performed in or on synthetic liposomes (see Tajib et al., 2000, Nature Biotechnology 18: 649-654, which is incorporated herein by reference) or virus-induced budding membranes containing the OR polypeptide as defined herein, which can either be the OR5A2 receptor as defined herein (SEQ ID NO:2), its central region (SEQ ID NO:11), or a chimeric receptor comprising said central region (see WO0102551, 2001, incorporated herein by reference).

In another embodiment of any one of the preceding methods, the method is performed using a membrane fraction from cells expressing the OR polypeptide as defined herein, which can either be the OR5A2 receptor as defined herein (SEQ ID NO:2), its central region (SEQ ID NO:11), or a chimeric receptor comprising said central region.

In a preferred embodiment of either one of the preceding methods, the method is performed on a protein chip.

In another preferred embodiment of either one of the preceding methods, the measuring is performed using a method selected from label displacement, surface plasmon resonance, fluorescence resonance energy transfer, fluorescence quenching, and fluorescence polarization.

In another embodiment of either one of the preceding methods, the agent is selected from the group consisting of a peptide, a polypeptide, an antibody or antigen-binding fragment thereof, a lipid, a carbohydrate, a nucleic acid, and a small organic molecule.

According to the present invention, when a functional assay is used, the step of measuring a signaling activity of the OR5A2 receptor as defined herein may comprise detecting a change in the level of a second messenger.

In another embodiment, the step of measuring a signaling activity comprises measurement of guanine nucleotide binding/coupling or exchange, adenylate cyclase activity, cAMP, Protein Kinase C activity, Protein Kinase A activity phosphatidylinosotol breakdown, diacylglycerol, inositol triphosphate, intracellular calcium, calcium flux, arachidonic acid, MAP kinase activity, tyrosine kinase activity, melanophore assay, receptor initialization assay, or reporter gene expression. When the G-protein binding/coupling or exchange is measured, of all Gα subunits possible preferably the behaviors of GTP-binding protein G protein alpha-olf subunit (olfactory), also G-olf, is studied. The sequence of the human G-olf subunit has been deposited previously at the Genebank under accession number L10665. However, G-olf subunits of other species may be used and studied.

In a preferred embodiment, the measuring of the signaling activity comprises using a fluorescence or luminescence assay. Fluorescence and luminescence assays may comprise the use of $Ca^{2+}$ sensitive fluorophores including fluo3, Fluo4 or Fura, (Molecular probes); Ca3- and Ca6-kit family (Molecular Device) and aequorin. Furthermore, said assays may apply an automated fluorometric or luminescent reader such as FDSS (Hammamatsu) or FLIPR (Molecular Device).

The invention further encompasses a method of modulating the activity of the OR5A2 receptor as defined herein in a cell, said method comprising the step of delivering to said cell, a musk compound as defined herein or an agent that modulates the activity of the OR polypeptide as defined herein, which can either be the OR5A2 receptor as defined herein (SEQ ID NO:2), its central region (SEQ ID NO:11), or a chimeric receptor comprising said central region, such that the activity of the OR is modulated.

In another embodiment of any one of the preceding methods, the method is a high throughput screening method.

In another embodiment of any one of the preceding methods, the agent is part of a chemical library or animal organ extracts.

According to the present invention, the agent identified or detected by any of the preceding methods, or the composition comprising said agent, may be used to find new musk compounds. Alternatively, these may be used for the preparation of odorant activators or odorant enhancer. For instance, an OR activator or enhancer may be used as a deodorant. An OR activator or enhancer may be added to a fragrance or perfume formulation already used as a deodorant to reinforce its efficacy.

The present invention also encompasses a composition comprising the isolated OR polypeptide and a musk compound.

The present invention further relates to the use of musk compounds for the production of a kit for screening agents that modulate the signaling of the OR5A2 receptor as defined herein, or in combination with the OR5A2 receptor as defined herein for the production of a kit to screen odorant activators or odorant enhancers.

In addition, the present invention encompasses the use of a commercially or non-commercial available musk compound as a ligand for the OR5A2 receptor as defined herein.

The invention further encompasses a kit comprising the isolated OR5A2 polypeptide, one or more musk compound(s) as defined herein and packaging materials therefore; an isolated polynucleotide encoding the OR polypeptide as defined herein, which can either be the OR5A2 receptor as defined herein (SEQ ID NO:2), its central region (SEQ ID NO:11), or a chimeric receptor comprising said central region, one or more musk compound(s), and packaging materials therefore; a kit comprising a cell expressing said OR polypeptide or membranes thereof or several cells expressing said OR polypeptide or membranes thereof, one or more musk compound(s) as defined herein and packaging materials therefore. Said cell(s) may be transformed with a polynucleotide encoding said OR. In a preferred embodiment, said kit encompasses the OR5A2 receptor as defined herein, or any variant of said OR and one or more musk compound(s) as defined herein.

The invention hence provides for the following aspects:

Aspect 1. Use of the OR5A2 polypeptide defined by the amino acid sequence of SEQ ID NO. 2 or a polypeptide sequence having at least 80% amino acid identity, and preferably 90%, 95%, 96%, 97%, 98%, 99% or higher, including 100% amino acid identity, to SEQ ID NO. 2, for identifying agents that interfere with the binding between said OR5A2 receptor and one or more musk compounds.

Aspect 2. A method of identifying an agent or a sample containing one or more agent(s) that modulate(s) the activity of the OR5A2 polypeptide, said method comprising:
 a) contacting the OR5A2 polypeptide with said agent or sample;
 b) measuring a signaling activity of said OR5A2 polypeptide in the presence of said agent or sample; and
 c) comparing the activity measured in the presence of said agent or sample to the activity measured in a reaction in which said OR5A2 polypeptide is contacted with one or more musk compound(s) at its/their $EC_{50}$, wherein said agent or sample is identified as an agent or a sample, that modulates the activity of the OR5A2 receptor as defined herein when the amount of the activity measured in the presence of the agent or sample is at least 10% of the amount induced by said musk compound(s) at its/their EON.

Aspect 3. A method of identifying an agent or a sample, containing one or more agents, that modulates the activity of the OR5A2 receptor as defined herein, said method comprising: a) contacting said OR5A2 polypeptide with one or more musk compound(s) as defined herein in the presence and in the absence of an agent or sample; and b) measuring a signaling activity of said OR5A2 polypeptide, and c) comparing the amount of said activity measured in a reaction containing said OR5A2 polypeptide and musk compound(s) without the agent or sample to the amount of said activity measured in a reaction containing said OR5A2 polypeptide, musk compound and said agent or sample, wherein a change in the activity in the presence of the agent or sample relative to the activity in the absence of the agent or sample, identifies said agent or sample as an agent or sample, that modulates the activity of the OR5A2 receptor as defined herein.

Aspect 4. The method according to aspect 3, wherein an increase in the activity in the presence of said agent or sample relative to the activity in the absence of said agent or sample identifies said agent or sample as an agent or sample, that increases the activity of the OR5A2 receptor as defined herein.

Aspect 5. The method according to aspect 3, wherein a decrease in the activity in the presence of said agent or sample relative to the activity in the absence of said agent or sample identifies said agent or sample as an agent or a sample that decreases the activity of the OR5A2 receptor as defined herein.

Aspect 6. A method of identifying an agent or a sample, containing one or more agents, that modulates the activity of the OR5A2 receptor as defined herein, said method comprising: a) contacting said OR5A2 polypeptide with an agent or sample; b) measuring the binding the said agent or sample to the said OR5A2 polypeptide; and c) comparing the binding of the said agent or sample to the binding of the said OR5A2 polypeptide to one or more musk compound(s) as defined herein at its/their $EC_{50}$, wherein said agent or sample is identified as an agent or a sample that modulates the activity of the OR5A2 receptor as defined herein when the amount of the binding of said agent or sample is at least 10% of the amount binding of said musk compound(s) present at its/their $EC_{50}$.

Aspect 7. A method of identifying an agent, or a sample containing one or more agents, that modulates the interaction between one or more musk compound(s) as defined herein and the OR5A2 receptor as defined herein, said method comprising: a) contacting said OR5A2 polypeptide with said musk compound(s) in the presence and absence of an agent or sample under conditions permitting the binding of said musk compound(s) to said OR5A2 polypeptide; and b) measuring the binding of OR5A2 polypeptide to said musk compound(s), wherein a modulation in binding in the presence of the agent or sample, relative to the binding in the absence of the agent or sample, identifies said agent or sample as an agent or a sample that modulates the interaction between one or more musk compound(s) as defined herein and the OR5A2 receptor as defined herein.

Aspect 8. The method according to aspect 7, wherein an increase in the binding in the presence of said agent or sample relative to the binding in the absence of said agent or sample identifies said agent or sample as an agent or sample, that increases the binding of the OR5A2 receptor as defined herein.

Aspect 9. The method according to aspect 7, wherein a decrease in the binding in the presence of said agent or sample relative to the binding in the absence of said agent or sample identifies said agent or sample as an agent or a sample that decreases the binding of the OR5A2 receptor as defined herein.

Aspect 10. The method according to any one of aspects 2 to 9, wherein the one or more musk compound(s) is detectably labeled, preferably with a moiety selected from the group consisting of a radioisotope, a fluorophore, and a quencher of fluorescence.

Aspect 11. The method according to any one of aspects 2 to 10, wherein the contacting is performed in, or on a cell expressing said OR5A2 polypeptide, preferably wherein said cell is selected from: Human embryonic kidney cells (HEK293), Chinese hamster cells (CHO), Monkey cells (COS), primary olfactory cells, *Xenopus* cells, insect cells, yeast or bacteria.

Aspect 12. The method according to any one of aspects 2 to 11, wherein the contacting is performed in or on synthetic liposomes or virus-induced budding membranes containing an OR5A2 polypeptide.

Aspect 13. The method according to any one of aspects 2 to 12, wherein the method is performed using a membrane fraction from cells expressing said OR5A2 polypeptide or on a protein chip.

Aspect 14. The method according to any one of aspects 2 to 13, wherein the measuring is performed using a method selected from label displacement, surface plasmon resonance, fluorescence resonance energy transfer, fluorescence quenching, and fluorescence polarization.

Aspect 15. The method according to any one of aspects 2 to 14, wherein the agent is selected from the group comprising: a peptide, a polypeptide, an antibody or antigen-binding fragment thereof, a lipid, a carbohydrate, a nucleic acid, and a small organic molecule.

Aspect 16. The method according to any one of aspects 2 to 15, wherein the step of measuring a signaling activity of the OR5A2 receptor as defined herein comprises detecting a change in the level of a second messenger.

Aspect 17. The method according to any one of aspects 2 to 16, wherein measuring the signaling activity comprises using a fluorescence or luminescence assay, preferably the use of $Ca^{2+}$ sensitive fluorophores including fluo3, Fluo4 or Fura; Ca3- and Ca6-kit family or aequorin, or wherein said assays apply an automated fluorometric or luminescent reader such as FDSS or FLIPR.

Aspect 18. The method according to any one of aspects 2 to 17, wherein the method is a high throughput screening method.

Aspect 19. The method according to any one of aspects 2 to 18, wherein the agent is part of a chemical library or animal organ extracts.

Aspect 20. A method of modulating the activity of the OR5A2 receptor as defined herein in a cell, said method comprising the step of delivering to said cell, a musk compound or an agent that modulates the activity of said OR5A2 polypeptide, such that the activity of the OR5A2 is modulated.

Aspect 21. A method for the preparation of an odorant activator, odorant enhancer or a deodorant, comprising the steps of:
a) identifying a candidate agent according to any one of the methods of aspects 3 to 20, and
b) adding said agent to a composition for use as odorant activator, odorant enhancer or a deodorant.

Aspect 22. A kit comprising an isolated OR5A2 polypeptide, one or more musk compound(s) and packaging materials therefore.

Aspect 23. A kit comprising an isolated polynucleotide encoding the OR5A2 polypeptide, one or more musk compound(s), and packaging materials therefore.

Aspect 24. A kit comprising a cell expressing said the OR5A2 polypeptide, or membranes thereof or several cells expressing the OR5A2 polypeptide, or membranes thereof; one or more musk compound(s) as defined herein and packaging materials therefore.

Aspect 25. Use of the kit according to any one of aspects 22 to 24, for screening agents that modulate the signaling of the OR5A2 receptor, preferably for screening agents that can be used as odorant activators, odorant enhancers or deodorants.

Aspect 26. Use of a musk compound as a ligand for the OR5A2 receptor.

Aspect 27. Use of the kits according to any one of aspects 22 to 26, for performing screening methods based upon the interaction of the OR5A2 receptor with one or more musk compounds.

Aspect 28. Use or method according to any of the preceding aspects, wherein said musk compounds are selected from the group comprising: nitromusk compounds, linear musk compounds, polycyclic musk compounds and macrocyclic musk compounds.

Aspect 29. Use or method according to aspect 28, wherein said nitromusk compounds and/or said linear musk compounds and/or said polycyclic musk compounds and/or said macrocyclic musk compounds are selected from the group of molecules depicted in Table 2.

BRIEF DESCRIPTION OF THE FIGURES

FIG. 1: A. Concentration-response analysis of the OR of the invention (namely OR5A2, OR5A2 variant_1) with different activators corresponding to six different musks representative of the four structurally diverse groups of musk (macrocyclic musks: Oxalide T and Cervolide; polycyclic musks: Cashmeran and Phantolide; nitro musk: Moskene, alicyclic musks: Sylkolide). These analyses have been performed according to the procedure described in "Experimental procedure". pEFIBRHO corresponds to the empty vector and is used as control. B. Structure of the different musk used in the concentration-response analysis (FIG. 1A).

FIG. 4: BLASTP is used for polypeptide sequence alignment of OR5A2 variant_1 (SEQ ID NO:2) and OR5A2 variant 2 (SEQ ID NO:4). The protein sequence alignment shows one amino acid substitution (bold, underlined): proline (P) is substituted by leucine (L) at position 172.

FIG. 6: A. ClustalW2 is used for polypeptide sequences alignment of OR5A2 variant_1 (OR5A2) (SEQ ID NO:2) and the chimeric OR5A2_variant 1 (SEQ ID NO:2) proteins. The black boxes represent identical nucleotides and conserved motifs in the different ORs. B. Concentration-response analysis of the chimeric OR5A2_variant 1 and the OR2A5 with different activators corresponding to 6 different musks representative of the four structurally diverse groups of musk (Musk Xylene, Serenolide, Galaxolide®, Velvione, Cashmeran, Musk Ketone). Only the chimeric OR5A2_variant 1 (left panel), but not the OR2A5 (right panel) shows dose response curves to the different musks tested. C. Concentration-response analysis of the chimeric OR5A2_variant 1 with Beta-ionone and ethyl-fenchol the described activators of OR5A1 and OR11A1. pEFIBRHO corresponds to the empty vector and is used as control. Results indicate that Beta-ionone and ethyl-fenchol are not able to activate the chimeric OR5A2_variant 1. The chimeric OR5A2_variant 1 (cf. SEQ ID NO:10) has the same specificity than the OR of invention.

DETAILED DESCRIPTION OF THE INVENTION

Definitions

Figures 2, 3:
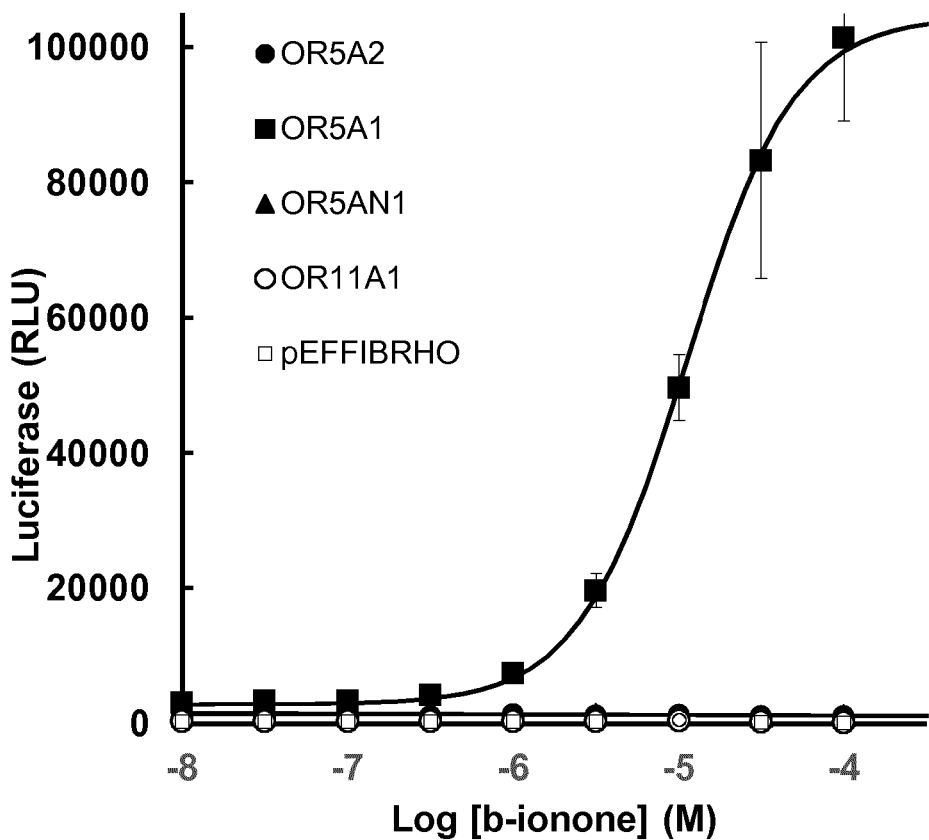
FIG. 2: A. ClustalW2 is used for polypeptide sequences alignment of OR5A2 variant_1 (SEQ ID NO2), OR5A2 variant_2 (SEQ ID NO4), OR5AN1 (SEQ ID NO7), OR11A1 (SEQ ID NO8) and OR5A1 (SEQ ID NO9) proteins. The black boxes represent identical nucleotides and conserved motifs in the five different ORs. B. Distance matrix showing that the OR5A2 is closer to OR5A1, a receptor activated by beta-ionone, than to OR5AN1 or OR11A1, two receptors known to respond to some musk subfamilies.
FIG. 3: A. Concentration-response analysis of the OR of the invention (i.e. OR5A2 as defined herein), OR5AN1, OR11A1 and OR5A1 with Beta-ionone the described activator of OR5A1. pEFIBRHO corresponds to the empty vector and is used as control. Results indicate that Beta-ionone is able to activate OR5A1 only. B. Concentration-response analysis of the OR of the invention (i.e. OR5A2 as defined herein), OR5AN1, OR11A1 and OR5A1 with ethyl-fenchol the described activator of OR11A1. pEFIBRHO corresponds to the empty vector and is used as control. Results indicate that ethyl-fenchol is able to activate OR11A1 only.
Figure 3:
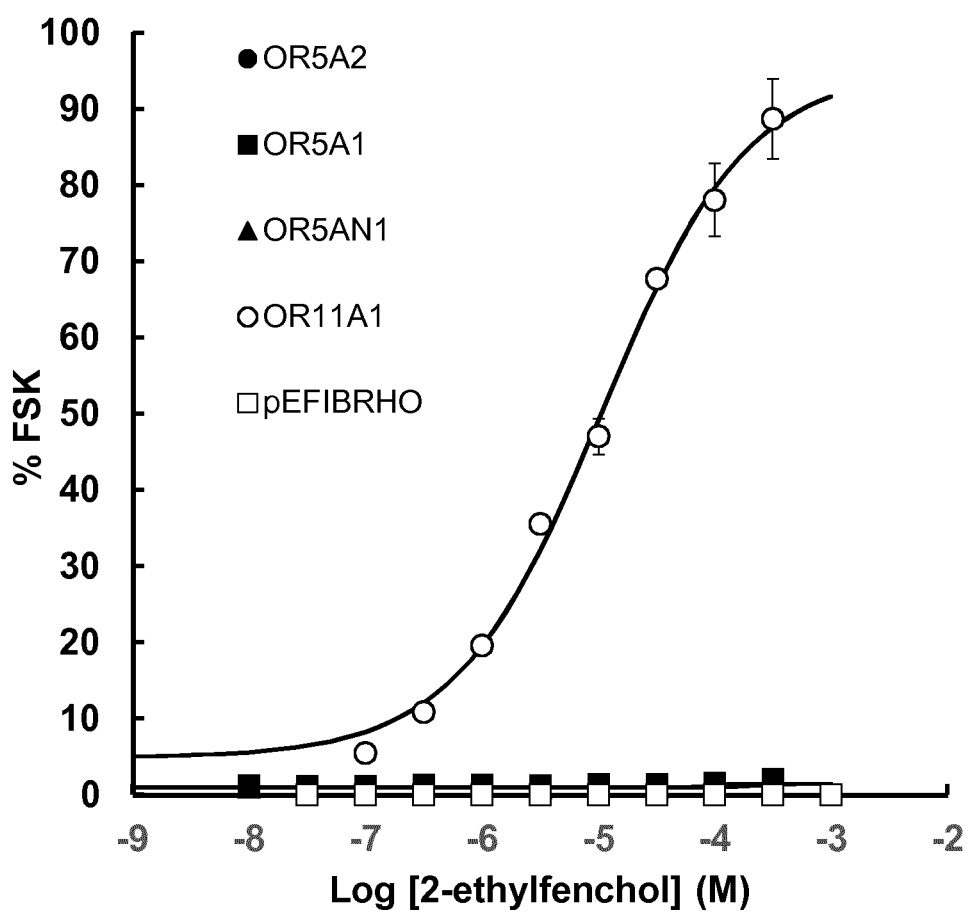

As used herein, the term "Olfactory Receptor polypeptides (ORs)" in general refers to polypeptides from the G protein coupled receptor family mainly expressed by olfactory neurons. ORs may have the ability to interact with odorant molecules and to transduce the odorant signal.

The terms "Olfactory Receptor (OR) according to the invention" or "Olfactory Receptor polypeptides according to the invention" or "OR of the invention" or "OR5A2 receptor as defined herein" or "said OR polypeptide" denote the olfactory receptor family five subfamily A member two including haplotype variants such as, but not limited to, "OR5A2_variant_1" and "OR5A2_variant_2", corresponding to the polypeptide sequences referred in the "sequences list" SEQ ID NO:2 and 4 respectively, that are able to be activated by Musk compound(s) as defined herein. Examples of the OR5A2 receptor as defined herein include, but are not limited to polypeptides having at least 80%, at least 85%, or 86% amino acid identity, and preferably 90%, 95%, 96%, 97%, 98%, 99% or higher, including 100% amino acid identity, to the sequence represented in "sequences list" (SEQ ID NO:2) which maintain the ability to be activated by Musk compound(s) as defined herein. Said homology may relate to the whole polypeptide or only part of the polypeptide such as CDR domain (ligand-binding domain of the receptor). According to Pilpel and Lancet (Protein Science 8:969-977, 1999) the CDR domain of a GPCR may be defined following the indications published: TM3-#4, TM3-#8, TM3-#11, TM3-#12, TM3-#15, TM4 #11, TM4 #15, TM4-#19, TM4-#22, TM4-#23, TM4-#26, TM5-#3, TM5-#6, TM5-#7, TM5-#10, TM5-#11 and TM5-#13, wherein TMx indicates the transmembrane region of said receptor, and # indicates the amino acid position within said region. More specifically, the inventors have identified the region covering TM2 to 7 of the OR as being particularly important for the specificity for musk compounds as defined herein. Said region is defined by SEQ ID NO:11. A specific example of a variant having a high degree of identity to the OR5A2 polypeptide of the invention is represented by SEQ ID NO:4 and denoted as OR5A2_variant_2. Said term OR polypeptide of the invention also encompasses "OR5A2 chimeric receptors or polypeptides" as defined herein.

As used herein, the term "OR5A2 polynucleotide" refers to a polynucleotide that encodes the OR5A2 polypeptides as defined herein. Preferably, said polynucleotide has an identity of at least 86% or more, preferably 90%, 95%, 96%, 97%, 98%, 99% or higher, including 100% nucleic acid identity, to the sequence represented by SEQ ID NO:1 (encoding OR5A2 variant 1) or SEQ ID NO:3 (encoding OR5A2 variant 2).

As used herein, the term "OR5A2 chimeric receptor or polypeptide" refers to a receptor that comprises the central region of the OR5A2 receptor, encompassing the transmembrane domains 2 to 7 defined by amino acid sequence ID NO:11 or a sequence having at least 95%, 96%, 97%, 98%, 99% or higher sequence identity, including 100% identity. Such chimeric receptors can further comprise the backbone of a G protein coupled receptor, more preferably of an olfactory receptor. More particularly, such a chimeric OR5A2 receptor comprises the TM2 to TM7 central region of the OR5A2 receptor (SEQ ID NO:11), fused at its N-terminus to the N-terminal extracellular moiety, the transmembrane domain 1 and the intracellular loop 1, of a G protein coupled receptor and fused at its C-terminus to the intracellular C-terminal end of a G protein receptor. Said G protein coupled receptor preferably is an olfactory receptor. A particular example of such a chimeric OR5A2 receptor is defined by SEQ ID NO:10.

As used herein, the term "OR binding" refers to specific binding of an odorant molecule by an OR polypeptide as defined herein. Examples of odorant molecules include, but are not limited to musk compounds from the four different subfamilies: nitromusks, macrocyclic musks, linear musks, polycyclic musks.

As used herein, the term "OR signaling activity" refers to the initiation or propagation of signaling by an OR polypeptide as defined herein. OR signaling activity is monitored by measuring a detectable step in a signaling cascade by assaying one or more of the following: stimulation of GDP for GTP exchange on a G protein and most particularly G-olf; alteration of adenylate cyclase activity; protein kinase C modulation; protein kinase A modulation; phosphatidylinositol breakdown (generating second messengers diacylglycerol, and inositol triphosphate); intracellular calcium flux; activation of MAP kinases; modulation of tyrosine kinases; internalization assay; modulation of gene or reporter gene activity; or melanophore assay. A detectable step in a signaling cascade is considered initiated or mediated if the measurable activity is altered by 10% or more above or below a baseline established in the substantial absence of a musk compound relative to any of the OR activity assays described herein. The measurable activity can be measured directly, as in, for example, measurement of cAMP or diacylglycerol levels. Alternatively, the measurable activity can be measured indirectly, as in, for example, a reporter gene assay. For most of these assays, kits are commercially available.

As used herein, the term "Musk compound(s)" refers to one or more compound(s) that has/have an organoleptic description reminiscent of the smell of the strong-smelling substance secreted by the male musk deer. Said compounds are a class of fragrant substances that could be used a bases note in perfumery.

Preferably, Musk compounds as defined herein encompass synthetic musk compounds or natural musk compounds or commercially or not yet commercially available musk compounds falling within or not into the four structurally diverse groups of following chemicals: nitromusks, polycyclic musks, macrocyclic musks, and linear/alicyclic musks.

More preferably Musk compounds as defined herein encompass synthetic musk compounds or natural musk compounds or commercially or not yet commercially available musk compounds falling within the four structurally diverse groups of following chemicals: nitromusks, polycyclic musks, macrocyclic musks, and linear/alicyclic musks.

As used herein, the "Nitromusks" belong to the nitrophenyl derivatives. Preferably, Nitromusks generally refer to the five most commercially relevant fragrant compounds: musk ketone (4-tert-butyl-2,6-dimethyl-3,5-dinitroacetophenone), musk ambrette (2,6-dinitro-3-methoxy-4-tert-butyltoluene), musk moskene (1,1,3,3,5-pentamethyl-4,6-dinitro-2H-indene), musk tibetene (1-tert-butyl-3,4,5-trimethyl-2,6-dinitrobenzene) and musk xylene (1-tert-butyl-3,5-dimethyl-2,4,6-trinitrobenzene). More preferably, Nitromusks refer to musk ketone (4-tert-butyl-2,6-dimethyl-3,5-dinitroacetophenone), musk ambrette (2,6-dinitro-3-methoxy-4-tert-butyltoluene), musk moskene (1,1,3,3,5-pentamethyl-4,6-dinitro-2H-indene), and musk xylol (1-tert-butyl-3,5-dimethyl-2,4,6-trinitrobenzene).

As used herein, the "Polycyclic musks" are formed by a bi-cyclic core structure such as indane or tetraline type, which is substituted with a combination of an acetyl group or a pyran ring in combination with methyl, isopropyl and/or t-butyl groups. Preferably, Polycyclic musks refer to crysolide, Tonalide®, phantolide, cashmeran, Galaxolide®, traseolide, moxalone, vernolide and fixal.

As used herein, the term "Macrocyclic musks" possess at least a single ring composed of more than 6 carbons (often 10-15). Preferably, Macrocyclic musks refer to ethylene brassylate, thibetolide also known as exaltolide, 1,16-hexadecalactone, exaltenone, globanone also known as animusk, musk R1, velvione, cyclopentadecanone; muscone, civetone, musk MC4, cervolide, co-6-hexadecenlactone, nirvanolide, isoambrettolide, habanolide, musk 77 and oxalide T.

As used herein, the "linear/alicyclic musks" otherwise known as cycloalkyl ester, are a class of musk compounds with a structure corresponding to modified alkyl esters. Preferably, linear musks refer to cyclopentenyl propionate musk, serenolide, sylkolide and helvetolide.

An "enhancer" as defined herein is a molecule that modulates or enhances the perception of an odor elicited by one or more odorant molecules. An enhancer may act by interacting with an OR that transduces the said odor or by interacting with the natural ligand for the receptor. A "enhancer" of the invention can increase the intracellular response induced by an agonist, for example a musk present in a perfume, by at least 10%, preferably 15-25%, more preferably 25-50% and most preferably, 50-100%. An enhancer, useful according to the present invention, includes, but is not limited to, small molecules, aptamer, photoaptamer, modified natural ligand, etc. that specifically binds to at least a portion of an OR which is required for signal transduction through musk compounds (such as the ligand binding site). Preferably, the activator agent is volatile, or can be made volatile in combination with appropriate solvents or additives.

As used herein, an "agonist" is a ligand which binds to a receptor and mimic the intracellular response induced by a natural ligand or another identify agonist, for example a new compound present in library.

As used herein, a "modulator" refers to a compound that increases or decreases the cell surface expression of a receptor of the invention, increases or decreases the binding of a ligand to the OR5A2 as defined herein, or any compound that increases or decreases the intracellular response initiated by an active form of the OR5A2 as defined herein, either in the presence or absence of a ligand for the receptor, for example a musk compound present in a perfume. A modulator includes an agonist, or enhancer, as defined herein. A modulator can be for example, a small molecule, a polypeptide, a peptide, an antibody or antigen-binding fragment thereof, a lipid, a carbohydrate, a nucleic acid, an aptamer, a photoaptamer, or a small chemical compound or small organic molecule. Candidate modulators can be natural or synthetic compounds, including, for example, synthetic small molecules, compounds contained in extracts of animal, plant, bacterial or fungal cells, as well as conditioned medium from such cells.

As used herein, the terms "increase" and "decrease" refer to a change in amount of ligand binding to the OR5A2 as defined herein and/or cell signaling through ORs of the invention of at least 10%. An "increase" or "decrease" in binding or signaling is preferably measured in response to contacting the OR5A2 as defined herein with a ligand in the presence of a candidate modulator, wherein the change in binding or signaling is relative to the binding or signaling in the absence of the candidate modulator.

As used herein, the term "small molecule" refers to a compound having a molecular mass of less than 3000 Daltons, preferably less than 2000 or 1500, still more preferably less than 1000, and most preferably less than 600 Daltons. A "small organic molecule" is a small molecule that comprises carbon.

As used herein, the terms "change", "difference", "decrease", or "increase" as applied to e.g., binding or signaling activity or amount of a substance refer to an at least 10% increase or decrease in binding, signaling activity, or for example, level of mRNA, polypeptide or ligand relative to a standard in a given assay.

As used herein, the term "conditions permitting the binding of musk compound to the OR5A2 as defined herein" refers to conditions of, for example, temperature, salt concentration, pH and protein concentration under which said OR binds a musk compound. Exact binding conditions will vary depending upon the nature of the assay, for example, whether the assay uses viable cells or only a membrane fraction of cells.

As used herein, the term "agent" refers to molecules selected from the group comprising: a peptide, a polypeptide, an antibody or antigen-binding fragment thereof, a lipid, a carbohydrate, a nucleic acid, and a small organic molecule.

As used herein, the term "sample" refers to the source of molecules being tested for the presence of an agent or modulator compound that modulates binding to or signaling activity of the OR5A2 as defined herein. A sample can be an environmental sample, a natural extract of animal, plant, yeast or bacterial cells, a clinical sample, a synthetic sample, or a conditioned medium from recombinant cells or from a fermentation process.

As used herein, the term "membrane fraction" refers to a preparation of cellular lipid membranes containing the OR5A2 as defined herein. As the term is used herein, a "membrane fraction" is distinct from a cellular homogenate, in that at least a portion (i.e., at least 10%, and preferably more) of non-membrane-associated cellular constituents has been removed. The term "membrane associated" refers to those cellular constituents that are either integrated into a lipid membrane or are physically associated with a component that is integrated into a lipid membrane.

As used herein, the term "second messenger assay" preferably comprises the measurement of guanine nucleotide binding or exchange, adenylate cyclase, intra-cellular cAMP, intracellular inositol phosphate, intra-cellular diacylglycerol concentration, arachidonic acid concentration, MAP kinase(s) or tyrosine kinase(s), protein kinase C activity, or reporter gene expression or an aequorin-based assay according to methods known in the art and defined herein.

As used herein, the term "second messenger" refers to a molecule, generated or caused to vary in concentration by the activation of a G-Protein Coupled Receptor that participates in the transduction of a signal from that GPCR. Non-limiting examples of second messengers include cAMP, diacylglycerol, inositol triphosphate, arachidonic acid release, inositol triphosphate and intracellular calcium. The term "change in the level of a second messenger" refers to an increase or decrease of at least 10% in the detected level of a given second messenger relative to the amount detected in an assay performed in the absence of a candidate modulator.

As used herein, the term "aequorin-based assay" refers to an assay for GPCR activity that measures intracellular calcium flux induced by activated GPCRs, wherein intracellular calcium flux is measured by the luminescence of aequorin expressed in the cell.

As used herein, the term "binding" refers to the physical association of a molecule (e.g., a ligand such as a musk compound or an antibody) with a receptor (e.g., the OR5A2s of the invention as defined herein). As the term is used herein, binding is "specific" if it occurs with an $EC_{50}$ or a Kd of 1 mM less, generally in the range of 1 mM to 10 nM for example, binding is specific if the $EC_{50}$ or Kd is 1 mM, 500 µM, 100 µM, 10 µM, 9.5 µM, 9 µM, 8.5 µM, 8 µM, 7.5 µM, 7 µM, 6.5 µM, 6 µM, 5.5 µM, 5 µM, 4.5 µM, 4 µM, 3.5 µM, 3 µM, 2.5 µM, 2 µM, 1.5 µM, 1 µM, 750 nM, 500 nM, 250 nM or 100 nM or less.

As used herein, the term "EC 50" refers to that concentration of a compound at which a given activity, including binding of a musk compound or other ligand and a functional activity of an OR, is 50% of the maximum for that OR activity measurable using the same assay in the absence of compound. Stated differently, the "EC 50" is the concentration of compound that gives 50% activation, when 100% activation is set at the amount of activity that does not increase with the addition of more agonist.

As used herein, the term "saturation" refers to the concentration of a musk compound at which further increases in ligand concentration fail to increase the binding of ligand or OR-specific signaling activity.

As used herein, the term "increase in binding" refers to an increase of at least 10% in the amount of ligand binding detected in a given assay with a known or suspected modulator of the OR5A2 as defined herein relative to binding detected in an assay lacking that known or suspected modulator.

As used herein, the term "G-Protein coupled receptor," or "GPCR" refers to a membrane-associated polypeptide with 7 alpha helical transmembrane domains. Functional GPCR's associate with a ligand or agonist and also associate with and activate G-proteins. The OR5A2 as defined herein belongs to the family of GPCRs.

As used herein, the term "antibody" is the conventional immunoglobulin molecule, as well as fragments thereof which are also specifically reactive with one of the subject polypeptides. Antibodies can be fragmented using conventional techniques and the fragments screened for utility in the same manner as described herein below for whole antibodies. For example, F(ab)2 fragments can be generated by treating antibody with pepsin. The resulting F(ab)2 fragment can be treated to reduce disulfide bridges to produce Fab fragments. The antibody of the present invention is further intended to include bispecific, single-chain, and chimeric and humanized molecules having affinity for a polypeptide conferred by at least one CDR region of the antibody. In preferred embodiments, the antibody further comprises a label attached thereto and able to be detected, (e.g., the label can be a radioisotope, fluorescent compound, chemiluminescent compound, enzyme, or enzyme co-factor). The antibodies, monoclonal or polyclonal and their hypervariable portion thereof (FAB, FAB", etc.) as well as the hybridoma cell producing the antibodies are a further aspect of the present invention which find a specific industrial application in the field of diagnostics and monitoring of specific diseases, preferably the ones hereafter described. Inhibitors according to the invention include but are not limited to labeled monoclonal or polyclonal antibodies or hypervariable portions of the antibodies.

As used herein, the term "OR constitutive activity" refers to a measurable activity of an olfactory receptor expressed into a cell that occurs spontaneously without addition of a ligand for the said olfactory receptor.

The invention relates to the finding that one or more musk compound(s) are able to activate the specific OR5A2 olfactory receptor present in human nasal epithelium, called the OR5A2 polypeptide as defined herein. The OR5A2/musk compound(s) interaction is useful for screening assays for agents that modulate such an interaction and thus the function of the OR5A2. This OR5A2/musk compound(s) interaction also provides for the identification of modulators, new agonists which could be of interest in industry. Unexpectedly, the OR5A2 olfactory receptor is the only OR that can be activated by all known classes of musk compounds as defined herein.

Assays for the Identification of Agents that Modulate the Activity of ORs

Agents that modulate the activity of ORs can be identified in a number of ways that take advantage of the interaction of said receptors with musk compounds. For example, the ability to reconstitute OR5A2/musk compound(s) binding either in vitro, on cultured cells or in vivo provides a target for identification of agents that modulate that binding. Modulators of OR/musks binding can then be screened using a binding assay or a functional assay that measures downstream signaling through the said receptor. Both binding assays and functional assays are validated using musk compounds.

Another approach that uses the OR5A2/musk compound(s) interaction more directly to identify agents that modulate OR5A2 function measures changes in OR5A2 downstream signaling induced by candidate agents or candidate modulators. These functional assays can be performed in isolated cell membrane fractions or on cells expressing the receptor on their surfaces.

The following description provides methods for both binding and functional assays based upon the interaction of OR5A2 and one or more musk compound(s).

A. Or Polypeptides.

Assays using the interaction of OR polypeptide and musk compounds as defined herein require a source of OR polypeptide. The polynucleotide and polypeptide sequences of human ORs are presented herein in "sequences list". The human OR5A2, is also available at GenBank database accession Nos NM_001001954.1 (SEQ ID No1), NM_001001954.1:c.515C>T (SEQ ID No3). The polypeptide sequences are also recorded at accession Nos Q8NGI9, VAR_024097 respectively in the Uniprot database.

One skilled in the art can readily amplify an OR sequence from a sample containing mRNA encoding the protein through basic PCR and molecular cloning techniques using primers or probes designed from the known sequences. Also, since OR genes are intron-less genes, a person skilled in the art can amplify an OR sequence from genomic DNA.

The expression of recombinant polypeptides is well known in the art. Those skilled in the art can readily select vectors and expression control sequences for the expression of OR polypeptides according to the invention in eukaryotic or prokaryotic cells. OR polypeptides are preferably associated with the cell membrane or synthetic liposomes in order to have binding or signaling function. Methods for the preparation of cellular membrane fractions are well known in the art, e.g., the method reported by Hubbard & Cohn, 1975, J. Cell Biol. 64: 461-479, which is incorporated herein by reference. In order to produce membranes comprising OR polypeptides, one can e.g. apply such membrane isolation techniques to cells endogenously or recombinantly expressing one of the OR polypeptide of the invention. Alternatively, OR polypeptides can be integrated into membrane preparations by dilution of detergent solution of the polypeptide (see, e.g., Salamon et al., 1996, Biophys. J. 71:283-294, which is incorporated herein by reference).

B. Musk Compounds.

The structure of Musk molecules are well known by a skilled person. In addition, the person skilled in the art may easily derive equivalent musk from said structure and may easily test if said equivalents are able to bind and/or modulate the OR5A2 polypeptide as defined herein. Musk compounds may be isolated from natural samples, or chemically synthesized.

Methods which can be used to quantify said compounds may be, but are not limited to, a) for extraction and purification: solvent extraction, oil extraction, vapor extraction, $CO_2$ supercritical extraction, liquid chromatography, distillation, gas chromatography; b) for quantifying: gas chromatography, liquid chromatography and mass spectrometry. Said methods are well known in the art.

Musk compounds may be used in purified form or used as compositions. The amounts of the musk necessary in a given binding or functional assay according to the invention will vary depending upon the assay. If necessary for a given assay, a musk compound can be labeled by incorporation or addition of radioactive labels as pointed out above.

C. Assays to Identify Modulators of ORs Activity

The discovery that musk compounds from the four currently known structurally diverse groups of chemicals are ligands of the OR5A2 as defined herein, belonging to the class 2 olfactory receptor family permits the development of screening assays to identify agonists and modulators of said OR's activity. The screening assays will have two general approaches.

1) Ligand binding assays, in which cells expressing said OR5A2, membrane extracts from such cells, or immobilized lipid membranes comprising said OR5A2 are exposed to one or more labeled musk compound(s) as defined herein, known to bind said OR5A2 and a candidate compound. Following incubation, the reaction mixture is measured for specific binding of the labeled musk compound(s) to said OR5A2. Compounds that interfere with or displace labeled musk compound(s) from the OR5A2 can be identified as modulators, preferably enhancer of OR5A2 activity. Functional analysis can be performed on positive compounds to determine in which of these categories they fit.

Binding of a compound may be classified into 3 main categories: competitive binding, non-competitive binding and uncompetitive binding. A competitive binding compound resembles a second (reference) compound and binds to the same binding pocket of a target molecule (here receptor). Upon addition, the competitive binding compound displaces said second compound from said target. A non-competitive binding compound does not bind to the same binding pocket of the target molecule as a second (reference) compound but may interact with the effect of said second compound on said target molecule. The second compound is not displaced upon addition of the non-competitive binding compound. An uncompetitive-binding compound binds to the target molecule when a second compound is already bound. Cooperative binding means that a compound facilitates the binding of another compound which may be a reference compound. The cooperative effect is thus seen in the analysis of the Kd of said other compound.

2) Functional assays, in which a signaling activity of OR5A2 as defined herein is measured.

For agonist screening, cells expressing said OR5A2 or membranes prepared from them are incubated with a candidate compound, and a signaling activity of said OR5A2 is measured.

The assays are validated using one or more musk compound(s) as defined herein, as agonist(s), and the activity induced by compounds that modulate receptor activity is compared to that induced by the musk compound(s). An agonist or partial agonist will have a maximal biological activity corresponding to at least 10% of the maximal activity of the musk compound(s) when the agonist or partial agonist is present at 100 μM or less, and preferably will have 50%, 75%, 100% or more, including 2-fold, 5-fold, 10-fold or more activity than the musk compound(s).

Ligand Binding and Displacement Assays:

One can use OR5A2 polypeptide as defined herein expressed in a cell, or isolated membranes containing such OR5A2 polypeptide, along with one or more musk compound(s) as defined herein in order to screen for compounds that enhance the binding of musk compounds to OR polypeptides. When identified in an assay that measures binding or musk compound displacement alone, compounds will have to be subjected to functional testing to determine whether they act as agonists, antagonists or inverse agonists.

For displacement experiments, cells expressing said OR5A2 polypeptide (generally 25,000 cells per assay or 1 to 100 µg of membrane extracts) are incubated in binding buffer (e.g., 50 mM Hepes pH 7.4; 1 mM $CaCl_2$); 0.5% Bovine Serum Albumin (BSA) Fatty Acid-Free; and 0.5 mM $MgCl_2$) for 1.5 hrs (at, for example, 27° C.) with labeled musk compound in the presence or in the absence of increasing concentrations of a candidate modulator. To validate and calibrate the assay, control competition reactions using increasing concentrations of unlabeled musk can be performed. After incubation, cells are washed extensively, and bound, labeled musk compound is measured as appropriate for the given label (e.g., scintillation counting, enzyme assay, fluorescence, etc.). A decrease of at least 10% in the amount of labeled musk compound bound in the presence of the candidate modulator indicates displacement of binding by the candidate modulator. Candidate modulators are considered to bind specifically in this or other assays described herein if they displace 50% of the labeled musk compound.

Alternatively, binding or displacement of binding can be monitored by surface plasmon resonance (SPR). Surface plasmon resonance assays can be used as a quantitative method to measure binding between two molecules by the change in mass near an immobilized sensor caused by the binding or loss of binding of musk compound from the aqueous phase to said OR5A2 polypeptide immobilized in a membrane on the sensor. This change in mass is measured as resonance units versus time after injection or removal of the musk or candidate modulator and is measured using a Biacore Biosensor (Biacore AB). OR5A2 polypeptides as defined herein can be immobilized on a sensor chip (for example, research grade CM5 chip; Biacore AB) in a thin film lipid membrane according to methods described by Salamon et al. (Salamon et al., 1996, Biophys J. 71: 283-294; Salamon et al., 2001, Biophys. J. 80: 1557-1567; Salamon et al., 1999, Trends Biochem. Sci. 24: 213-219, each of which is incorporated herein by reference). Sarrio et al. demonstrated that SPR can be used to detect ligand binding to the GPCR A(1) adenosine receptor immobilized in a lipid layer on the chip (Sarrio et al., 2000, Mol. Cell. Biol. 20: 5164-5174, incorporated herein by reference). Conditions for musk binding to said OR5A2 in an SPR assay can be fine-tuned by one skilled in the art using the conditions reported by Sarrio et al. as a starting point.

SPR can assay for modulators of binding in at least two ways. First, one or more musk compound(s) as defined herein can be pre-bound to immobilized OR5A2 polypeptide as defined herein, followed by injection of the candidate modulator at approximately 10 µl/min flow rate and a concentration ranging from 1 nM to 1000 µM, preferably about 100 µM. Displacement of the bound musk compound(s) can be quantified, permitting detection of modulator binding. Alternatively, the membrane-bound musk compound(s) can be pre-incubated with a candidate modulator and challenged with musk compound(s). A difference in musk binding to said OR5A2 exposed to the modulator relative to that on a chip not pre-exposed to the modulator will demonstrate binding. In either assay, a decrease of 10% or more in the amount of musk compound(s) bound in the presence of candidate modulator, relative to the amount of musk compound(s) bound in the absence of candidate modulator indicates that the candidate modulator inhibits the interaction of said OR5A2 and said musk compound(s). A Biacore system can be plugged to a system identifying candidate modulator such as mass spectrometry, or gas chromatography.

Another method of measuring inhibition of binding of musk compounds as defined herein to the OR5A2 receptor as defined herein uses fluorescence resonance energy transfer (FRET). FRET is a quantum mechanical phenomenon that occurs between a fluorescence donor (D) and a fluorescence acceptor (A) in close proximity to each other (usually <100 A of separation) if the emission spectrum of D overlaps with the excitation spectrum of A. The molecules to be tested, e.g., one or more musk compound(s) and an OR5A2 polypeptide, are labeled with a complementary pair of donor and acceptor fluorophores. While close to each other due to the OR5A2/musk compound(s) interaction, fluorescence emitted upon excitation of the donor fluorophore will have a different wavelength from that emitted in response to the excitation wavelength when the molecules are not bound, thus allowing quantification of bound versus unbound polypeptides by measurement of emission intensity at each wavelength. Donor/acceptor pairs of fluorophores with which to label the target molecules are well known in the art.

A variation on FRET uses fluorescence quenching to monitor molecular interactions. One molecule in the interacting pair can be labeled with a fluorophore, and the other with a molecule that quenches the fluorescence of the fluorophore when brought into close apposition with it. A change in fluorescence upon excitation is indicative of a change in the association of the molecules tagged with the fluorophore: quencher pair. Generally, an increase in fluorescence of the labeled OR5A2 polypeptide is indicative that musk compound(s) bearing the quencher has been displaced. For quenching assays, a 10% or greater increase in the intensity of fluorescent emission in samples containing a candidate modulator, relative to samples without the candidate modulator, indicates that the candidate modulator inhibits OR5A2/musk compound(s) interaction.

Bioluminescence Resonance Energy Transfer (BRET) is a system for monitoring intermolecular interactions in vivo. The assay is based on non-radiative energy transfer between fusion proteins containing *Renilla* luciferase (Rluc) and e.g. Yellow Fluorescent Protein (YPF) or Green Fluorescent Protein (GFP). The BRET signal is generated by the oxidation of a coelenterazine derivative substrate. Said system may apply a cell-permeable and non-toxic coelenterazine derivative substrate DeepBlueC™ (DBC) and a mutant of the Green Fluorescent Protein (GFP) as acceptor. When the donor and acceptor are in close proximity the energy resulting from the catalytic degradation of the DBC is transferred from Rluc to GFP which will then emit fluorescence at its characteristic wavelength. This method allows higher distance between the two tested molecules and is fluorophore-angle independent.

In addition to the surface plasmon resonance, FRET and BRET methods, fluorescence polarization measurement is useful for quantification of musk/receptor binding. The fluorescence polarization value for a fluorescently-tagged molecule depends on the rotational correlation time or tumbling rate. Protein complexes, such as those formed by an OR5A2 associating with one or more fluorescently labeled musk compound(s), have higher polarization values than uncomplexed, labeled musk compound(s). The inclusion of a candidate modulator of the OR5A2/musk compound(s) interaction results in an increase (activator) or a decrease (inhibitor) in fluorescence polarization, relative to a mixture without the candidate modulator, e.g. if the candidate inhibitor disrupts or inhibits the interaction of the OR5A2 with the musk compound(s). Fluorescence polarization is well suited for the identification of small molecules that disrupt the formation of polypeptide or protein complexes. A modulation of 10% or more in fluorescence polarization in samples containing a candidate modulator, relative to fluorescence polarization in a sample lacking the candidate modulator, indicates that the candidate modulator modulates the OR5A2/musk compound(s) interaction. Another alternative for monitoring OR5A2/musk compound(s) interactions uses a biosensor assay. ICS biosensors have been described by AMBRI (Australian Membrane Biotechnology Research Institute; ambri.com.au). In this technology, the association of molecules such as an OR and a musk compound, is coupled to the closing of gramacidin-facilitated ion channels in suspended membrane bilayers and thus to a measurable change in the admittance (similar to impedance) of the biosensor. This approach is linear over six orders of magnitude of admittance change and is ideally suited for large scale, high throughput screening of small molecule combinatorial libraries. A 10% or greater change (increase or decrease) in admittance in a sample containing a candidate modulator, relative to the admittance of a sample lacking the candidate modulator, indicates that the candidate modulator impacts the interaction of OR5A2 and musk compound(s).

It is important to note that in assays of acid-protein interaction, it is possible that a modulator of the interaction need not necessarily interact directly with the domain(s) of the proteins that physically interact. It is also possible that a modulator will interact at a location removed from the site of acid-protein interaction and cause, for example, a conformational change in the OR5A2 polypeptides. Modulators (inhibitors or agonists) that act in this manner are nonetheless of interest as agents to modulate the activity of OR5A2.

Any of the binding assays described can be used to determine the presence of an agent in a sample, e.g., a tissue sample, that binds to the OR5A2 polypeptide as defined herein, or that affects the binding of one or more musk compound(s) to said OR5A2. To do so, OR5A2 polypeptides are reacted with one or more musk compound(s) or another ligand in the presence or in the absence of the sample, and said musk compound(s) or ligand binding is measured as appropriate for the binding assay being used. A modulation of 10% or more in the binding of said musk compound(s) or other ligand indicates that the sample contains an agent that modulates musk compound or ligand binding to OR5A2 polypeptides.

Proteins Chips

The methods as defined herein may be applied on protein chips. Said protein chip may be, but is not limited to, a glass slide or a nitrocellulose membrane. Array-based methods for protein chips are well known in the art. The protein arrays preferably comprise one or more OR5A2 polypeptides as defined herein or fragments thereof that are responsible for the binding with musk compound such as the TM 2 to 7 central region of said OR polypeptide. The protein chip preferably comprises all variant OR5A2 polypeptides or chimeric polypeptides as defined herein, or fragments thereof that are responsible for the binding with musk compound(s).

Functional Assays of Receptor Activity

A non-exhaustive list of functional assays is detailed in this section:

i. GTPase/GTP Binding Assays:

For GPCRs such as OR polypeptides, a measure of receptor activity is the binding of GTP by cell membranes containing receptors. In the method described by Traynor and Nahorski, 1995, Mol. Pharmacol. 47: 848-854, incorporated herein by reference, one essentially measures G-protein coupling to membranes by measuring the binding of labeled GTP to the membrane. For GTP binding assays, membranes isolated from cells expressing the receptor are incubated in a buffer generally containing 20 mM HEPES, pH 7.4, 100 mM NaCl, and 10 mM MgCl2, 80 pM 35S-GTPγS and 3 μM GDP. The assay mixture is incubated for a period of time at a given temperature, for example 60 minutes at 30° C., after which unbound labeled GTP is removed by filtration onto GF/B filters. Bound, labeled GTP is measured by liquid scintillation counting. In order to assay for modulation of musk compound-induced OR5A2 activity, membranes prepared from cells expressing an OR5A2 polypeptide as defined herein are mixed with one or more musk compound(s) as defied herein, and the GTP binding assay is performed in the presence and in the absence of a candidate modulator of OR5A2 activity. A modulation of 10% or more in labeled GTP binding as measured by scintillation counting in an assay of this kind containing the candidate modulator, relative to an assay without the modulator, indicates that the candidate modulator inhibits or activates OR5A2 activity.

A similar GTP-binding assay can be performed without the musk compound(s) to identify compounds that act as agonists. In this case, the musk-compound-stimulated GTP binding is used as a standard. A compound is considered an agonist if it induces at least 50% of the level of GTP binding induced by the musk compound(s) when the compound(s) is(are) present at 1 mM or less, and preferably will induce a level the same as or higher than that induced by the musk compound(s).

GTPase activity is measured by incubating the membranes containing an OR polypeptide with gamma-32P-GTP. Active GTPase will release the label as inorganic phosphate, which is detected by separation of free inorganic phosphate in a 5% suspension of activated charcoal in 20 mM $H_3PO_4$, followed by scintillation counting. Controls include assays using membranes isolated from cells not expressing OR (mock-transfected), in order to exclude possible non-specific effects of the candidate compound.

In order to assay for the effect of a candidate modulator on OR5A2-regulated GTPase activity, membrane samples are incubated with one or more musk compound(s) as defied herein, with and without the modulator, followed by the GTPase assay. A change (increase or decrease) of 10% or more in the level of GTP binding or GTPase activity relative to samples without modulator is indicative of musk compound modulation by a candidate modulator.

ii. Downstream Pathway Activation Assays:

a. Calcium Flux—the Aequorin-Based Assay.

The aequorin assay takes advantage of the responsiveness of mitochondrial or cytoplasmic apoaequorin to intracellular calcium release or calcium flux (entrance) induced by the activation of GPCRs (Stables et al., 1997, Anal. Biochem. 252:115-126; Detheux et al., 2000, J. Exp. Med., 192 1501-1508; both of which are incorporated herein by reference). Briefly, OR-expressing clones are transfected to coexpress mitochondrial or cytoplasmic apoaequorin and G-alpha-16 or G-olf. Cells are incubated with 5 μM Coelenterazine H or derivates (Molecular Probes) for 4 hours at room temperature, washed in DMEM-F12 culture medium and resuspended at a concentration of $0.5 \times 10^6$ cells/ml. Cells are then mixed with test agonist peptides and light emission by the aequorin is recorded with a luminometer for 30 sec. Results are expressed as Relative Light Units (RLU). Controls include assays using membranes isolated from cells not expressing C356 (mock-transfected), in order to exclude possible non-specific effects of the candidate compound.

Aequorin activity or intracellular calcium levels are "changed" if light intensity increases or decreases by 10% or more in a sample of cells, expressing an OR polypeptide and treated with a candidate modulator, relative to a sample of cells expressing the OR polypeptide but not treated with the candidate modulator or relative to a sample of cells not expressing the OR polypeptide (mock-transfected cells) but treated with the candidate modulator.

When performed in the absence of a musk compound as defined herein, the assay can be used to identify an agonist or inverse agonist of OR5A2 activity. When the assay is performed in the presence of a musk compound as defined herein, it can be used to assay for an enhancer of OR5A2 activity.

1) A Fluo3, Fluo4, Fura2, Calcium3 or Calcium6 Based-Assay.

Fluorescence-based assays take advantage of calcium fluxes triggered by receptor activation: either calcium entrance through CNG for instance or calcium release from endoplasmic reticulum. Some fluorophores including but not limited to Fluo3, Fluo4 and Fura2 (Molecular Probes) and Calcum3 or Calcium6 kit series (Molecular Device) are known to bind calcium. Such fluorophore-calcium complexes emit fluorescence at specific wavelengths. Thereby, upon activation of a G-protein coupled receptor, calcium released from endoplasmic reticulum or entered through CNG binds to fluorophore leading to specific fluorescence emission. OR-overexpressing cells are incubated for 30 to 60 minutes with a solution of 1 to 8 µM fluorophore at 37° C. After thorough washing with saline buffer, 50 µl of the same buffer is poured into each well containing cells (6 to 1536). Tested agonists are then injected into such loaded cells and activation of an OR is followed by fluorescence measurement.

Intracellular calcium levels are "changed" if fluorescence intensity increases or decreases by 10% or more in a sample of cells, expressing an OR5A2 polypeptide as defined herein and treated with a candidate modulator, relative to a sample of cells expressing an OR5A2 polypeptide but not treated with the candidate modulator or relative to a sample of cells not expressing an OR5A2 polypeptide (mock-transfected cells) but treated with the candidate modulator.

2) Depolarization/Hyperpolarization Membrane Assay (DiBac Fluorophore for Instance).

The principle of this assay is to follow depolarization of the cell membrane. The anionic probe DiBAC4(3) partitions between intra- and extracellular compartments in a membrane potential-dependent manner. With increasing membrane potential (depolarization), the probe further partitions into the cell resulting in an increase of fluorescence. Conversely, hyperpolarization leads to a decrease of fluorescence due to dye extrusion.

The DiBAC4(3) probe is excited with a wavelength of 488 nm, and emits at a wavelength of 540 nm.

On the day of the experiment, add the glucose to the assay buffer (saline buffer) to a final concentration of 10 mM and the DiBAC4(3) probe to a final concentration of 5 µM. Maintain the assay buffer at 37° C. Remove the cell culture medium and rinse twice each well containing OR-overexpressing cells with 200 µl of pre-heated assay buffer. Place 180 µl of Assay buffer containing DiBAC4(3) and incubate the cells for 30 min at the appropriate temperature. Cell plates will be ready for assay after these 30 mins. incubation.

Collect baseline for 2 mins. prior any addition. Add 20 µl of candidate modulators to the appropriate well and collect the data for an additional 25 mins.

Membrane polarization is "changed" if fluorescence intensity increases or decreases by 10% or more in a sample of cells, expressing an OR5A2 polypeptide as defined herein and treated with a candidate modulator, relative to a sample of cells expressing an OR5A2 polypeptide but not treated with the candidate modulator or relative to a sample of cells not expressing an OR5A2 polypeptide (mock-transfected cells) but treated with the candidate modulator.

3) Melanophore assay. The melanophore assay is a color-based assay. Basically cells used for this assay are derived from skin of the frog *Xenopus laevis*. These immortalized cells contain melanosomes, which are organelles containing dark pigment. Activation of endogenous or recombinant GPCR that trigger activation of adenylate cyclase or phospholipase C lead to melanosome dispersion and therefore cell darkening. Alternatively, a GPCR that inhibits adenylate cyclase or phospholipase C leads to cell lightening. Thereby, instead of measuring concentrations of second messenger, one can easily pinpoint hit observing cell coloration change. This color change can easily be quantified on a microplate reader measuring absorbance at 650 nM or by examination on a video imaging system.

b. Adenylate Cyclase Assay: Assays for adenylate cyclase activity are described by Kenimer & Nirenberg, 1981, Mol. Pharmacol. 20: 585-591, incorporated herein by reference. That assay is a modification of the assay taught by Solomon et al., 1974, Anal. Biochem. 58: 541-548, also incorporated herein by reference. Briefly, 100 µl reactions contain 50 mM Tris-Hcl (pH 7.5), 5 mM MgCl2, 20 mM creatine phosphate (disodium salt), 10 units (71 µg of protein) of creatine phosphokinase, 1 mM α-32P-ATP (tetrasodium salt, 2 pCi), 0.5 mM cyclic AMP, G-3H-labeled cyclic AMP (approximately 10,000 cpm), 0.5 mM Ro20-1724, 0.25% ethanol, and 50-200 µg of protein homogenate to be tested (i.e., homogenate from cells expressing or not expressing an OR polypeptide, treated or not treated with carboxylic acid with or without a candidate modulator). Reaction mixtures are generally incubated at 37° C. for 6 minutes. Following incubation, reaction mixtures are deproteinized by the addition of 0.9 ml of cold 6% trichloroacetic acid. Tubes are centrifuged at 1800×g for 20 minutes and each supernatant solution is added to a Dowex AG50W-X4 column. The cAMP fraction from the column is eluted with 4 ml of 0.1 mM imidazole-HCl (pH 7.5) into a counting vial. Assays should be performed in triplicate. Control reactions should also be performed using protein homogenate from cells that do not express an OR polypeptide.

Assays should be performed using cells or extracts of cells expressing an OR5A2 polypeptide as defined herein, treated or not treated with one or more musk compound(s) as defined herein with or without a candidate modulator. Control reactions should be performed using mock-transfected cells, or extracts from them in order to exclude possible non-specific effects of some candidate modulators.

According to the invention, adenylate cyclase activity is "changed" if it increases or decreases by 10% or more in a sample taken from cells treated with a candidate modulator of OR5A2 activity, relative to a similar sample of cells not treated with the candidate modulator or relative to a sample of cells not expressing an OR5A2 polypeptide (mock-transfected cells) but treated with the candidate modulator. Alternatively, a decrease of activity by 10% or more by the candidate modulator of OR5A2 polypeptides in a sample treated with a reference compound may be tested.

c. cAMP Assay:

Intracellular cAMP is measured using a cAMP radioimmunoassay (RIA) or cAMP binding protein according to methods widely known in the art. For example, Horton & Baxendale, 1995, Methods Mol. Biol. 41: 91-105, which is incorporated herein by reference, describes an RIA for cAMP.

A number of kits for the measurement of cAMP are commercially available, such as the High Efficiency Fluorescence Polarization-based homogeneous assay marketed by LJL Biosystems and NEN Life Science Products. Control reactions should be performed using extracts of mock-transfected cells to exclude possible non-specific effects of some candidate modulators. Assays should be performed using cells or extracts of cells expressing an OR5A2 polypeptide as defined herein, treated or not treated with a musk compound with or without a candidate modulator. Control reactions should be performed using mock-transfected cells, or extracts from them in order to exclude possible non-specific effects of some candidate modulators The level of cAMP is "changed" if the level of cAMP detected in cells, expressing an OR5A2 polypeptide as defined herein and treated with a candidate modulator of OR5A2 activity (or in extracts of such cells), using the RIA-based assay of Horton & Baxendale, 1995, supra, increases or decreases by at least 10% relative to the cAMP level in similar cells not treated with the candidate modulator.

d. Phospholipid Breakdown, DAG Production and Inositol Triphosphate Levels:

Receptors that activate the breakdown of phospholipids can be monitored for changes due to the activity of known or suspected modulators of an OR by monitoring phospholipid breakdown, and the resulting production of second messengers DAG and/or inositol triphosphate (IP3). Methods of measuring each of these are described in Phospholipid Signaling Protocols, edited by Ian M. Bird. Totowa, NJ, Humana Press, 1998, which is incorporated herein by reference. See also Rudolph et al., 1999, J. Biol. Chem. 274: 11824-11831, incorporated herein by reference, which also describes an assay for phosphatidylinositol breakdown. Assays should be performed using cells or extracts of cells expressing an OR5A2 polypeptide as defined herein, treated or not treated with one or more musk compound(s) as defined herein with or without a candidate modulator. Control reactions should be performed using mock-transfected cells, or extracts from them in order to exclude possible non-specific effects of some candidate modulators.

According to the invention, phosphatidylinositol breakdown, and diacylglycerol and/or inositol triphosphate levels are "changed" if they increase or decrease by at least 10% in a sample from cells expressing an OR5A2 polypeptide and treated with a candidate modulator in the presence or in the absence of one or more musk compound(s), relative to the level observed in a sample from cells expressing a carboxylic polypeptide that is not treated with the candidate modulator.

e. PKC Activation Assays:

GrOwth factor receptor tyrosine kinases tend to signal via a pathway involving activation of Protein Kinase C (PKC), which is a family of phospholipid- and calcium-activated protein kinases. PKC activation ultimately results in the transcription of an array of proto-oncogene transcription factor-encoding genes, including c-fos, c-myc and c-jun, proteases, protease inhibitors, including collagenase type I and plasminogen activator inhibitor, and adhesion molecules, including intracellular adhesion molecule I (ICAM I). Assays designed to detect increases in gene products induced by PKC can be used to monitor PKC activation and thereby receptor activity. In addition, activity of receptors that signal via PKC can be monitored through the use of reporter gene constructs driven by the control sequences of genes activated by PKC activation. This type of reporter gene-based assay is discussed in more detail below.

For a more direct measure of PKC activity, the method of Kikkawa et al., 1982, J. Biol. Chem. 257: 13341, incorporated herein by reference, can be used. This assay measures phosphorylation of a PKC substrate peptide, which is subsequently separated by binding to phoephocellulose paper. This PKC assay system can be used to measure activity of purified kinase, or the activity in crude cellular extracts. Protein kinase C sample can be diluted in 20 mM HEPES/2 mM DTT immediately prior to assay.

The substrate for the assay is the peptide Ac-FKKSFKL-NH2 (SEQ ID No5), derived from the myristoylated alanine-rich protein kinase C substrate protein (MARCKS). The Km of the enzyme for this peptide is approximately 50 µM. Other basic, protein kinase C-selective peptides known in the art can also be used, at a concentration of at least 2-3 times their Km. Cofactors required for the assay include calcium, magnesium, ATP, phosphatidylserine and diacylglycerol. Depending upon the intent of the user, the assay can be performed to determine the amount of PKC present (activating conditions) or the amount of active PCK present (non-activating conditions). For most purposes according to the invention, non-activating conditions will be used, such that the PKC that is active in the sample when it is isolated is measured, rather than measuring the PKC that can be activated. For non-activating conditions, calcium is omitted in the assay in favor of EGTA.

The assay is performed in a mixture containing 20 mM HEPES, pH 7.4, 1-2 mM DTT, 5 mM MgCl2, 100 µM ATP, ~1 µCi γ-32P-ATP, 100 µg/ml peptide substrate (~100 µM), 140 µM/3.8 µM phosphatidylserine/diacylglycerol membranes, and 100 µM calcium (or most preferably 500 µM EGTA). 48 µl of sample, diluted in 20 mM HEPES, pH 7.4, 2 mM DTT is used in a final reaction volume of 80 µl. Reactions are performed at 30° C. for 5-10 minutes, followed by addition of 25 µl of a solution containing 100 mM ATP and 100 mM EDTA with a pH value of 8.0, which stops the reactions.

After the reaction is stopped, a portion (85 µl) of each reaction is spotted onto a Whatman P81 cellulose phosphate filter, followed by washes: four times 500 ml of 0.4% phosphoric acid, (5-10 min. per wash); and a final wash in 500 ml 95% EtOH, for 2-5 min. Bound radioactivity is measured by scintillation counting. Specific activity (cpm/nmol) of the labeled ATP is determined by spotting a sample of the reaction onto P81 paper and counting without washing. Units of PKC activity, defined as nmol phosphate transferred per min, are calculated as follows:

The activity, in UNITS (nmol/min) is:

=(cpm on paper)×(105 µl total/85 µl spotted)/(assay time, min) (specific activity of ATP cpm/nmol).

An alternative assay can be performed using a Protein Kinase C Assay Kit sold by PanVera (Cat. #P2747).

Assays are performed on extracts from cells expressing an OR5A2 polypeptide as defined herein, treated or not treated with one or more musk compound(s) as defined herein with or without a candidate modulator. Control reactions should be performed using mock-transfected cells, or extracts from them in order to exclude possible non-specific effects of some candidate modulators.

According to the invention, PKC activity is "changed" by a candidate modulator when the units of PKC measured by either assay described above increase or decrease by at least 10%, in extracts from cells expressing an OR5A2 polypeptide and treated with a candidate modulator, relative to a reaction performed on a similar sample from cells not treated with a candidate modulator.

f. PKA Activation Assays

PKA activity can be assayed using any of several kits available commercially, for example from molecular device IMAP PKA assay kit, or from promega ProFluor PKA assay kit.

Assays should be performed using cells or extracts of cells expressing an OR5A2 polypeptide as defined herein, treated or not treated with one or more musk compound(s) as defined herein with or without a candidate modulator. Control reactions should be performed using mock-transfected cells, or extracts from them in order to exclude possible non-specific effects of some candidate modulators PKA activity is "changed" if the level of activity is increased or decreased by 10% or more in a sample from cells, expressing an OR polypeptide, treated with a candidate modulator relative to PKA kinase activity in a sample from similar cells not treated with the candidate modulator.

g. Kinase Assays:

MAP kinase activity can be assayed using any of several kits available commercially, for example, the p38 MAP Kinase assay kit sold by New England Biolabs (Cat #9820) or the FlashPlate™ MAP Kinase assays sold by Perkin-Elmer Life Sciences.

Assays should be performed using cells or extracts of cells expressing an OR5A2 polypeptide as defined herein, treated or not treated with one or more musk compound(s) as defined herein with or without a candidate modulator. Control reactions should be performed using mock-transfected cells, or extracts from them in order to exclude possible non-specific effects of some candidate modulators MAP Kinase activity is "changed" if the level of activity is increased or decreased by 10% or more in a sample from cells, expressing an OR5A2 polypeptide as defined herein, treated with a candidate modulator relative to MAP kinase activity in a sample from similar cells not treated with the candidate modulator.

Direct assays for tyrosine kinase activity using known synthetic or natural tyrosine kinase substrates and labeled phosphate are well known, as are similar assays for other types of kinases (e.g., Ser/Thr kinases). Kinase assays can be performed with both purified kinases and crude extracts prepared from cells expressing an OR5A2 polypeptide as defined herein, treated with or without a musk compound, with or without a candidate modulator. Control reactions should be performed using mock-transfected cells, or extracts from them in order to exclude possible non-specific effects of some candidate modulators. Substrates can be either full length protein or synthetic peptides representing the substrate. Pinna & Ruzzene (1996, Biochem. Biophys. Acta 1314: 191-225, incorporated herein by reference) list a number of phosphorylation substrate sites useful for measuring kinase activities. A number of kinase substrate peptides are commercially available. One that is particularly useful is the "Src-related peptide," (RRLIEDAEYAARG (SEQ ID No6); available from Sigma #A7433), which is a substrate for many receptor and nonreceptor tyrosine kinases. Because the assay described below requires binding of peptide substrates to filters, the peptide substrates should have a net positive charge to facilitate binding. Generally, peptide substrates should have at least 2 basic residues and a free amino terminus. Reactions generally use a peptide concentration of 0.7-1.5 mM.

Assays are generally carried out in a 25 µl volume comprising 5 µl of 5× kinase buffer (5 mg/mL BSA, 150 mM Tris-CI (pH 7.5), 100 mM MgCl2; depending upon the exact kinase assayed for, $MnCl_2$ can be used in place of or in addition to the $MgCl_2$), 5 µl of 1.0 mM ATP (0.2 mM final concentration), gamma-32P-ATP (100-500 cpm/pmol), 3 µl of 10 mM peptide substrate (1.2 mM final concentration), cell extract containing kinase to be tested (cell extracts used for kinase assays should contain a phosphatase inhibitor (e.g. 0.1-1 mM sodium orthovanadate)), and $H_2O$ to 25 µl. Reactions are performed at 30° C., and are initiated by the addition of the cell extract.

Kinase reactions are performed for 30 seconds to about 30 minutes, followed by the addition of 45 µl of ice-cold 10% trichloroacetic acid (TCA). Samples are spinned for 2 minutes in a microcentrifuge, and 35 µl of the supernatant is spotted onto Whatman P81 cellulose phosphate filter circles. The filters are washed three times with 500 ml cold 0.5% phosphoric acid, followed by one wash with 200 ml of acetone at room temperature for 5 minutes. Filters are dried and incorporated $^{32}P$ is measured by scintillation counting. The specific activity of ATP in the kinase reaction (e.g., in cpm/pmol) is determined by spotting a small sample (2-5 µl) of the reaction onto a P81 filter circle and counting directly, without washing. Counts per minute obtained in the kinase reaction (minus blank) are then divided by the specific activity to determine the moles of phosphate transferred in the reaction.

Assays should be performed using cells or extracts of cells expressing an OR5A2 polypeptide as defined herein, treated or not treated with a musk compound with or without a candidate modulator. Control reactions should be performed using mock-transfected cells, or extracts from them in order to exclude possible non-specific effects of some candidate modulators.

Tyrosine kinase activity is "changed" if the level of kinase activity is increased or decreased by 10% or more in a sample from cells, expressing an OR5A2 polypeptide, treated with a candidate modulator relative to kinase activity in a sample from similar cells not treated with the candidate modulator.

h. Transcriptional Reporters for Downstream Pathway Activation:

The intracellular signal initiated by binding of a modulator to a receptor, e.g., the OR5A2 polypeptide as defined herein, sets in motion a cascade of intracellular events, the ultimate consequence of which is a rapid and detectable change in the transcription and/or translation of one or more genes. The activity of the receptor can therefore be monitored by measuring the expression of a reporter gene driven by control sequences responsive to OR5A2 activation. As used herein "promoter" refers to the transcriptional control elements necessary for receptor-mediated regulation of gene expression, including not only the basal promoter, but also any enhancers or transcription-factor binding sites necessary for receptor-regulated expression. By selecting promoters that are responsive to the intracellular signals resulting from agonist binding, and operatively linking the selected promoters to reporter genes whose transcription, translation or ultimate activity is readily detectable and measurable, the transcription based reporter assay provides a rapid indication of whether a given receptor is activated.

Reporter genes such as luciferase, Chloramphenicol Acetyl Transferase (CAT), Green Fluorescent Protein (GFP), beta-lactamase or beta-galactosidase are well known in the art, as are assays for the detection of their products.

Genes particularly well suited for monitoring receptor activity are the "immediate early" genes, which are rapidly induced, generally within minutes of contact between the receptor and the effector protein or ligand. The induction of immediate early gene transcription does not require the synthesis of new regulatory proteins. In addition to rapid responsiveness to ligand binding, characteristics of preferred genes useful to make reporter constructs include: low or undetectable expression in quiescent cells; induction that is transient and independent of new protein synthesis; subsequent shut-off of transcription requires new protein synthesis; and mRNAs transcribed from these genes have a short half-life. It is preferred, but not necessary that a transcriptional control element have all of these properties for it to be useful.

In order to assay OR5A2 activity with a musk-responsive transcriptional reporter construct, cells that stably express an OR5A2 polypeptide as defined herein are stably transfected with the reporter construct. To screen for agonists, untreated cells are exposed to candidate modulators, or exposed to one or more musk compound(s) as defined herein, and expression of the reporter is measured. The musk compound-treated cultures serve as a standard for the level of transcription induced by a known agonist. An increase of at least 10% in reporter expression in the presence of a candidate modulator compared to reporter expression in the absence of any modulator indicates that the candidate is a modulator of OR5A2 activity. An agonist will induce at least as much, and preferably the same amount or more reporter expression than the musk compound(s). Partial agonists may activate the receptor less compared to the musk. This approach can also be used to screen for inverse agonists where cells express an OR5A2 polypeptide as defined herein at levels such that there is an elevated basal activity of the reporter in the absence of musk compound(s) or other agonists. A decrease in reporter activity of 10% or more in the presence of a candidate modulator, relative to its absence, indicates that the compound is an inverse agonist.

To screen for an enhancer, the cells expressing an OR5A2 polypeptide as defined herein and carrying the reporter construct are exposed to one or more musk compound(s) (or another agonist) in the presence and absence of a candidate modulator. An increase of 10% or more in reporter expression in the presence of candidate modulator, relative to the absence of the candidate modulator, indicates that the candidate is an enhancer of OR5A2 activity.

Controls for transcription assays include cells not expressing an OR5A2 polypeptide as defined herein but carrying the reporter construct, as well as cells with a promoter less reporter construct. Compounds that are identified as modulators of OR5A2-regulated transcription should also be analyzed to determine whether they affect transcription driven by other regulatory sequences and by other receptors, in order to determine the specificity and spectrum of their activity.

The transcriptional reporter assay, and most cell-based assays, are well suited for screening chemical libraries of chemical compounds for those that modulate OR5A2 activity. The libraries can be, for example, libraries from natural sources, e.g., plants, animals, bacteria, etc.

Candidate Modulators Useful According to the Invention

Candidate modulators can be screened from large libraries of synthetic or natural compounds. Numerous means are currently used for random and directed synthesis of various kinds of compounds. Synthetic compound libraries are commercially available from a number of companies including, for example, Maybridge Chemical Co. (Trevillet, Cornwall, UK), Comgenex (Princeton, NJ), Brandon Associates (Merrimack, NH), and Microsource (New Milford, CT). A rare chemical library is available from Aldrich (Milwaukee, WI). Combinatorial libraries of small organic molecules are available and can be prepared. Alternatively, libraries of natural compounds in the form of bacterial, fungal, plant and animal extracts are available from e.g., Pan Laboratories (Bothell, WA) or MycoSearch (NC), or are readily produceable by methods well known in the art. Additionally, natural and synthetically produced libraries and compounds are readily modified through conventional chemical, physical, and biochemical means.

EXAMPLES

Experimental Procedures:
Cell Culture and Cell Line Generation
HEK293T-RTP1A1/RTP2 cells were maintained in minimal essential medium (EMEM, Lonza) containing 10% fetal bovine serum (M10). These cells were generated by transfecting HEK293T with an expression vector containing the sequences of the chaperone proteins RTP1A1 and RTP2 and a resistance gene to puromycin, using Lipofectamine 2000. The recombinant cell population, used in these experiments, was selected by adding 10 µg/ml of puromycin into the culture medium and subsequently subcloned (WO 2014/191047 A1).

Odorant Molecule Dilution
Odorant molecules were diluted at a concentration of 1 mole/liter (M) into dimethyl sulfoxide (DMSO) to generate stock solutions.

For screening experiments, stock solutions of odorant molecules were diluted in EMEM 30 disposed in 96-well plates. Plates containing the tested compounds (1 compound/well) at a concentration of 2 mM, at a concentration of 632 µM and at a concentration of 200 µM were prepared.

For concentration-response analysis, serial dilutions of the tested molecules were prepared from stock solutions in EMEM plated into 96-well plates.

Luciferase Assay
For the initial deorphanisation screening and dose-response analysis, a Luciferase-based gene reporter assay (Promega, Leiden, The Nederlands) was used. Briefly, cells were platted on Poly-D-lysine-coated 96-well and transfected with a plasmid containing the CRE-luciferase and a plasmid containing the olfactory receptor. Sixteen hours after transfection, the culture medium was replaced by serum-free EMEM containing the tested compounds at a determined concentration. After four hours of incubation at 37° C. degree, cells were lysed and processed for luminescence measurement. Luminescene emission was recorded. Results were expressed as luciferase activity (Relative Fluorescence Unit (RLU)) or as percentage of the response induced by 10 µM of the adenylate cyclase activator Forskolin. An empty plasmid is used as negative control.

Example 1: Screening of Odorant Molecule Libraries

Odorant compound libraries containing musks and other types of compounds were used to identify activators of the OR of the invention. The deorphanisation campaign was performed on OR of the invention with a series of 891 odorant compounds. Musks from the four structurally different groups were included in the 891 tested odorants (Table 1).

Each compound was tested at 3 different concentrations (1 mM, 316 µM, 100 µM). The different compounds of the tested libraries were disposed at the same concentration into 96 well plates (1 molecule/well) containing cells expressing the OR of the invention. The activity of the tested compounds was measured using the luciferase activity as explained above. The median luciferase activity induced by the tested compounds and the associated standard deviation were determined. Putatively active compounds (hits) were defined as compounds inducing a luciferase activity higher or equal to the median+2 standard deviations.

Figure 5:
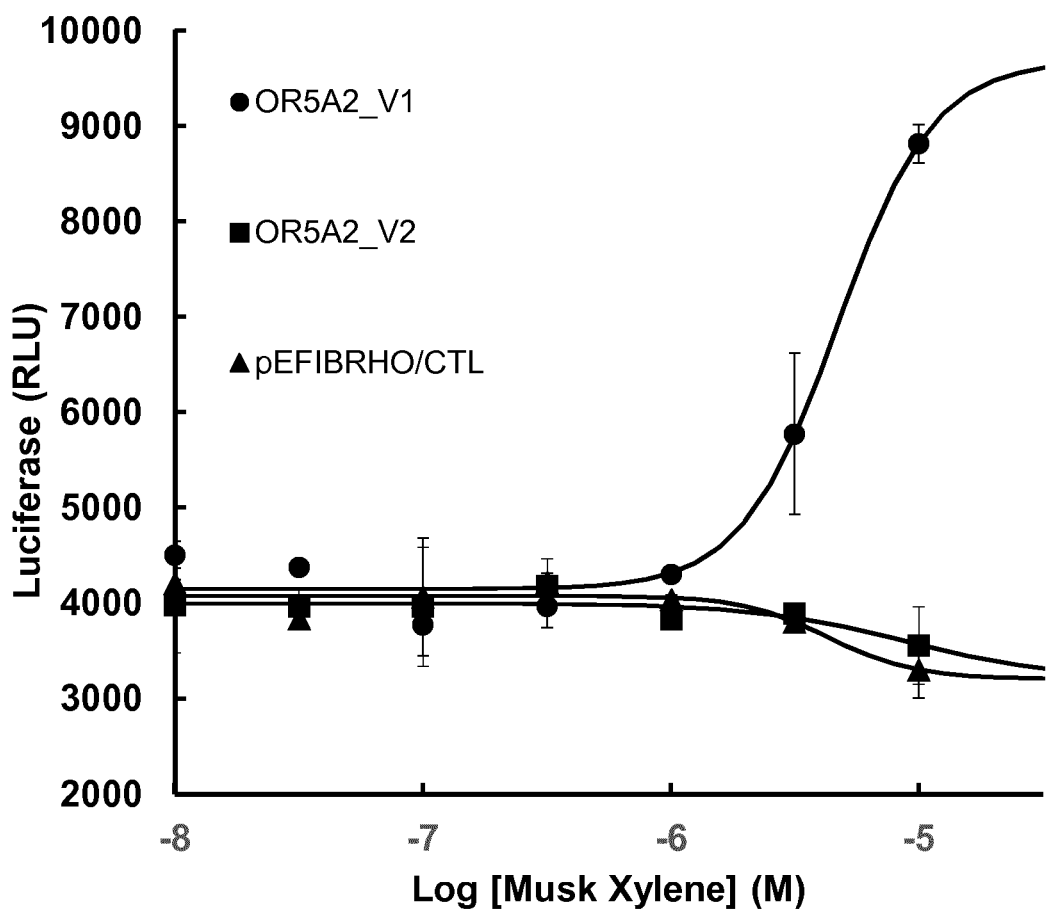
FIG. 5: Concentration-response analysis of the OR of the invention (i.e. OR5A2 variant_1), OR5A2 variant_2, and empty vector pEFIBRHO with different activators corresponding to 6 different musks representative of the four structurally diverse groups of musk (Musk Xylene, Serenolide, Galaxolide®, Velvione, Cashmeran, Musk Ketone). Only OR5A2 variant_1 shows dose response curves to the different musk tested.
Figure 5:
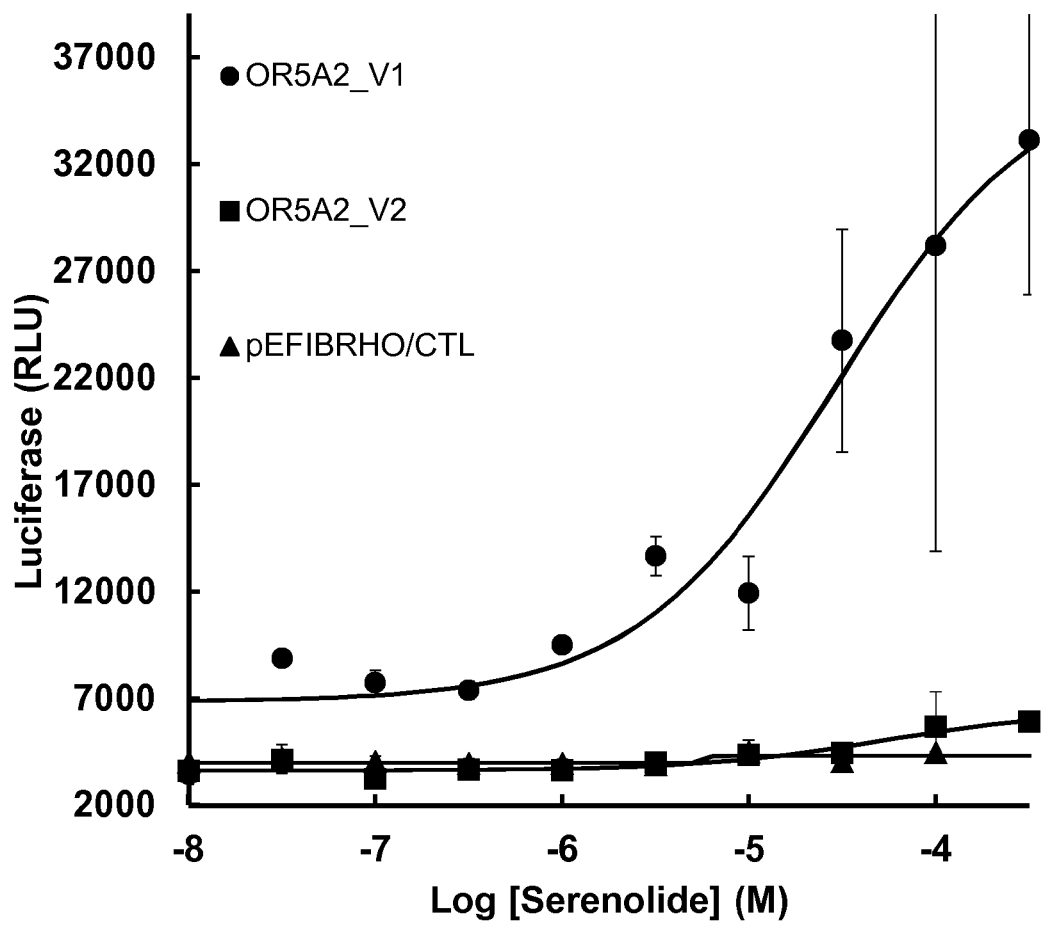
Figure 5:
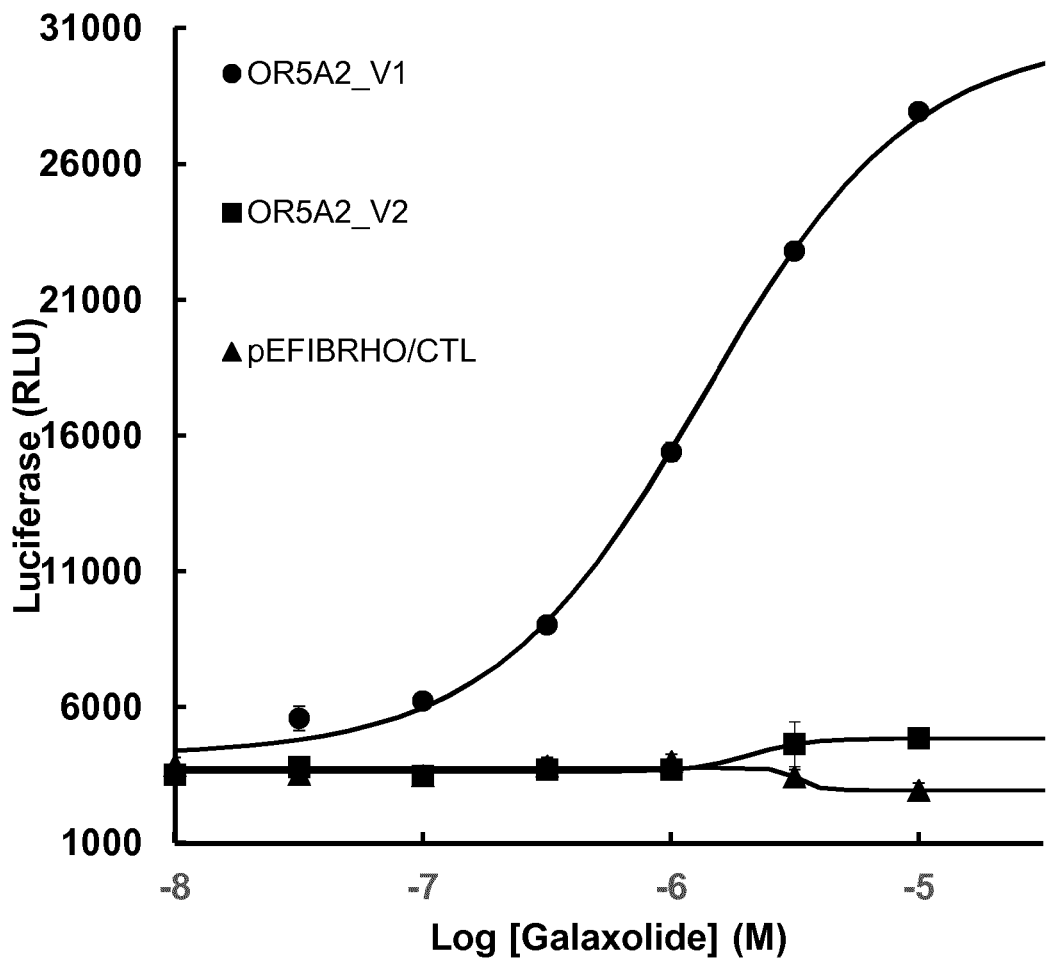
Figure 5:
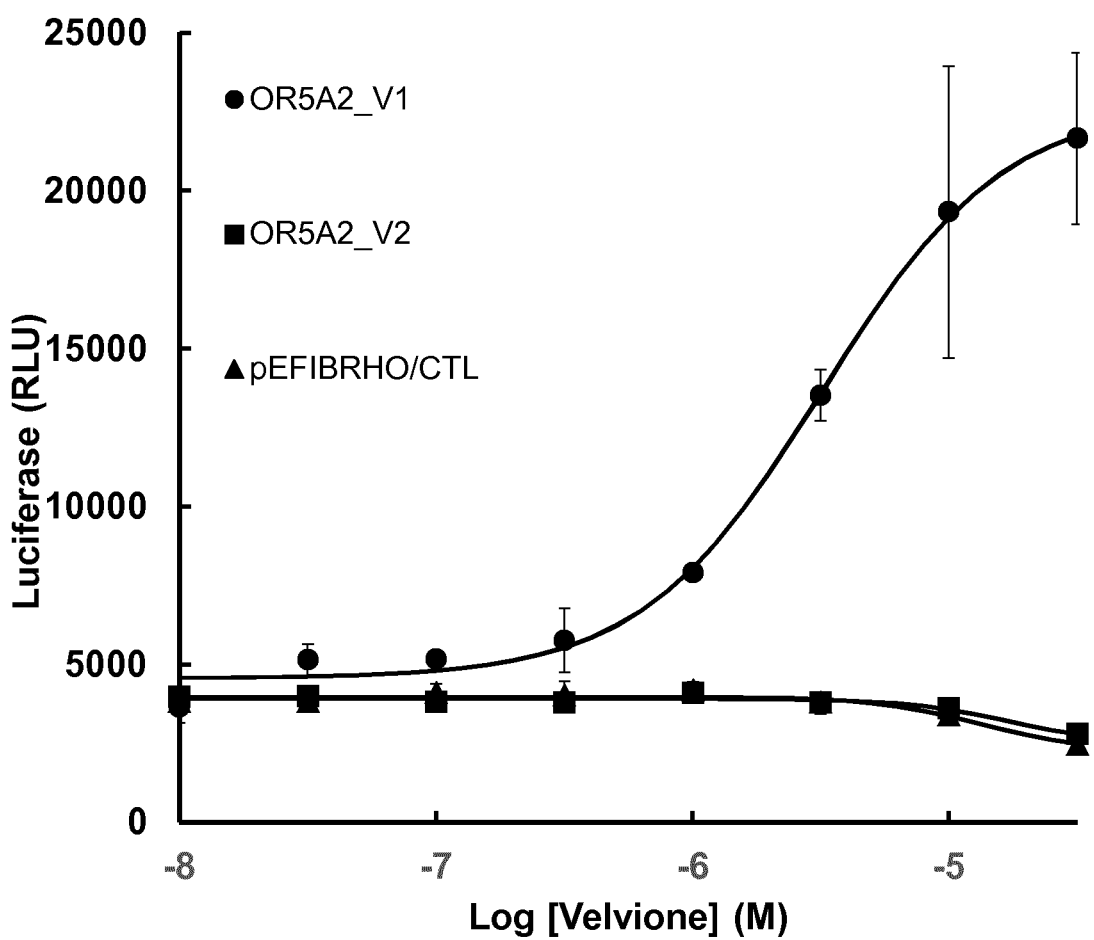
Figure 5:
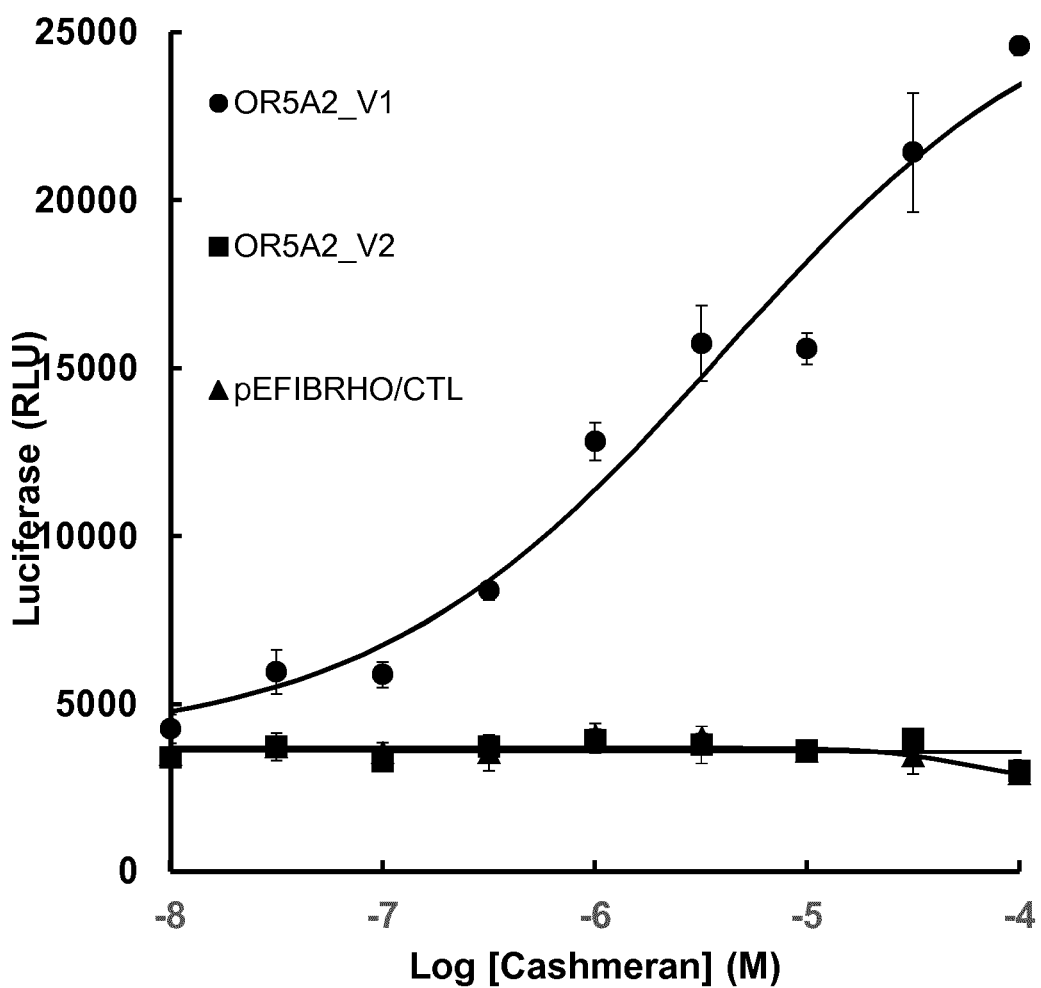
Figure 5:
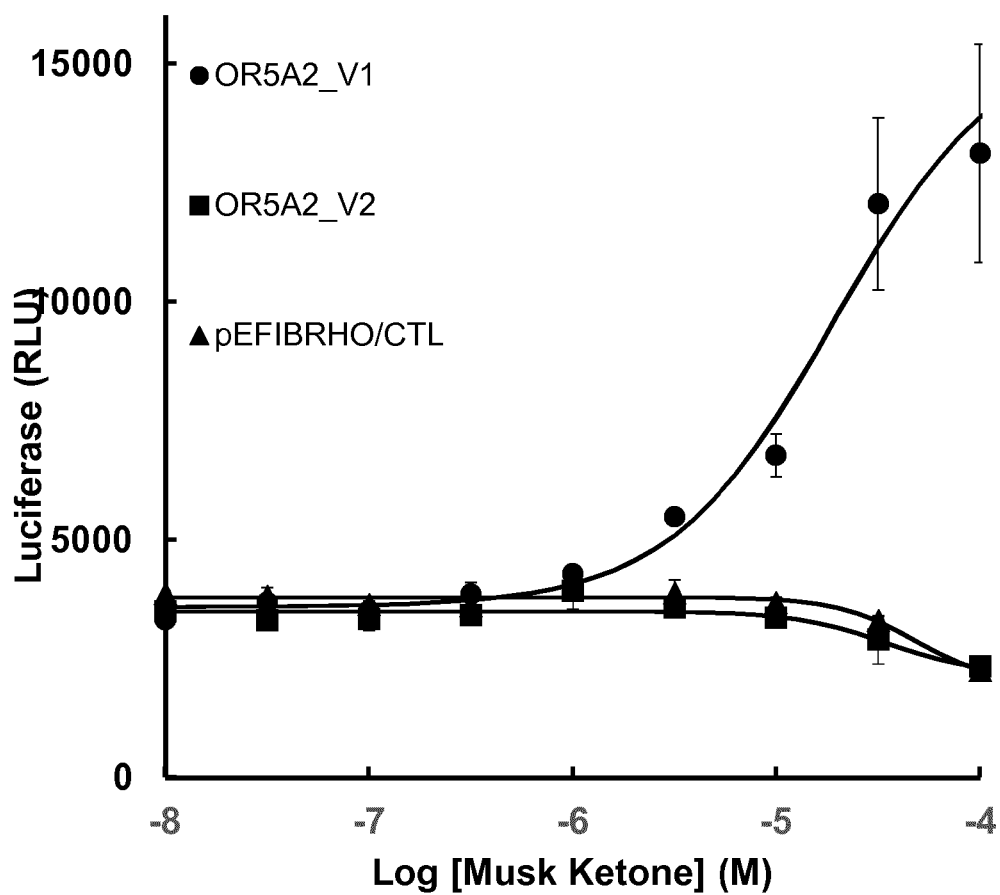

In these experimental conditions, the tested OR (corresponding to the OR of the invention, namely: OR5A2, in particular OR5A2_variant 1) was therefore found to respond specifically and exclusively to different musks: serenolide, ethylene brassylate and malaxone. Table 1 summarizes the complete list of odorant compounds tested for the deorphanization of the OR of the invention. The results clearly show that, among the 891 tested compounds, the OR of the invention is only activated by macrocyclic musks, polycyclic musks, nitromusks and linear musks. This result is all the more surprising since OR5A2 was previously excluded as a musk-specific receptor by 2 different publications (Shirasu et al. 2014 *Neuron* 81, 165-78; FIG. 5F supplemental, Sato-Akuhara N et al. 2016 *J Neurosci.* 36(16), 4482-91).

Example 2: Concentration-Response Analyses of Musk Ligand-OR Interactions

In order to validate the aforementioned hits, concentration-response analyses using the luciferase-based reporter assay were achieved using semi-logarithmic serial dilutions of hit molecules, from 1 mM to 316 nM, on OR5A2_variant 1. In these analyses we also included ORs previously described as musk-specific receptors OR5AN1 (SEQ ID n° 7) (WO 2015/020158 A1, Shirasu et al. 2014 Neuron 81, 165-78, Sato-Akuhara N et al. 2016 J Neurosci. 36(16), 4482-91) and OR11A1 (SEQ ID n° 8) (WO 2016/201152 A1). By phylogenic analysis, we found that the most similar OR gene to OR5A2 was OR5A1 (SEQ ID n° 9) with 71% nucleic acid identity and 67% amino acid identity (FIGS. 2A-B). Therefore, OR5A1 was included in the analyses. 35 musk compounds from the four structurally different chemical groups previously described were tested in concentration-response analyses (Table 2). In each experiment, an empty vector was used as negative control (pEF1BRHO). Representative concentration-response curves using musk compounds are given in FIG. 1A. FIG. 1B shows their structures. Full results including the calculated EC50 are given in Table 2; "non active" represent negative experiments, no activation after testing.

Figure 7:
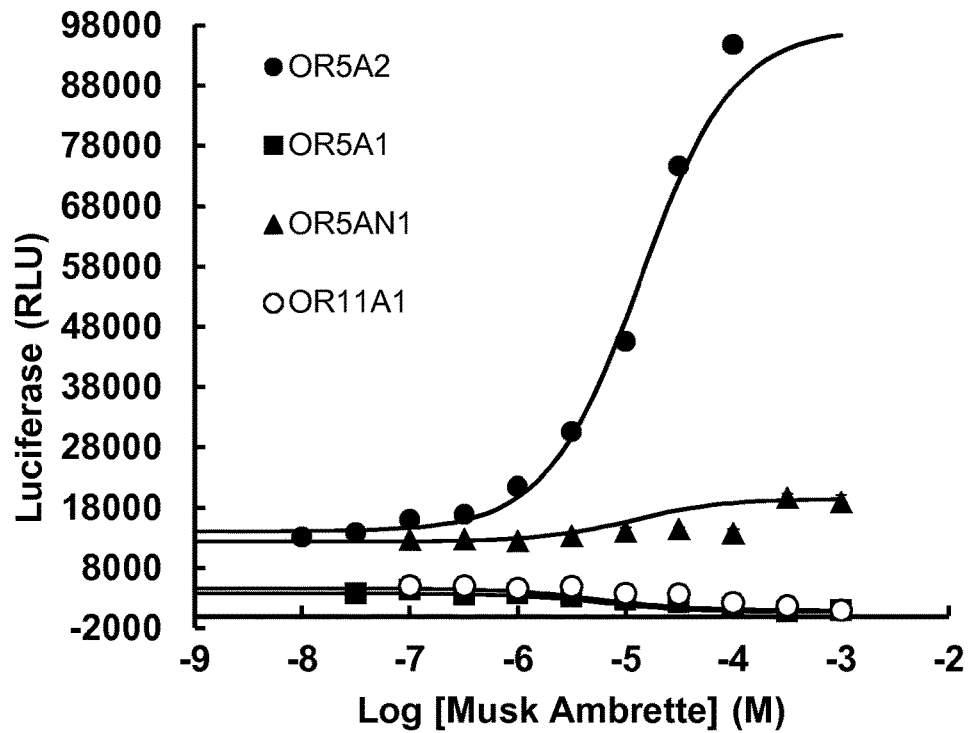
FIG. 7: Dose response curves of (A) Musk Ambrette and (B) Moskene on receptors OR5A2, OR5A1, OR5AN1, and OR11A1.
Figure 7B:
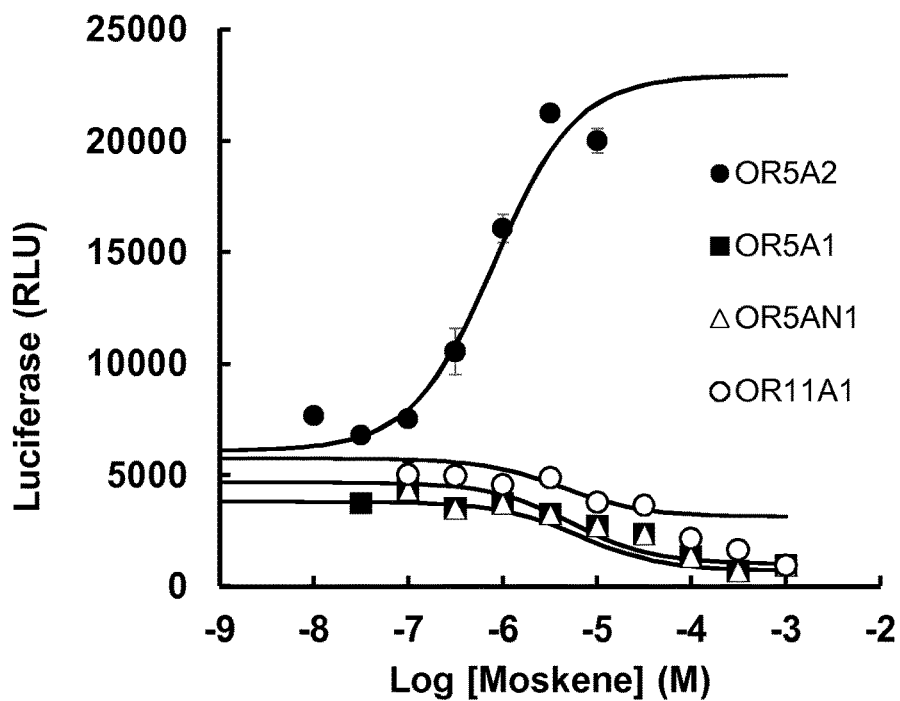
Figure 8:
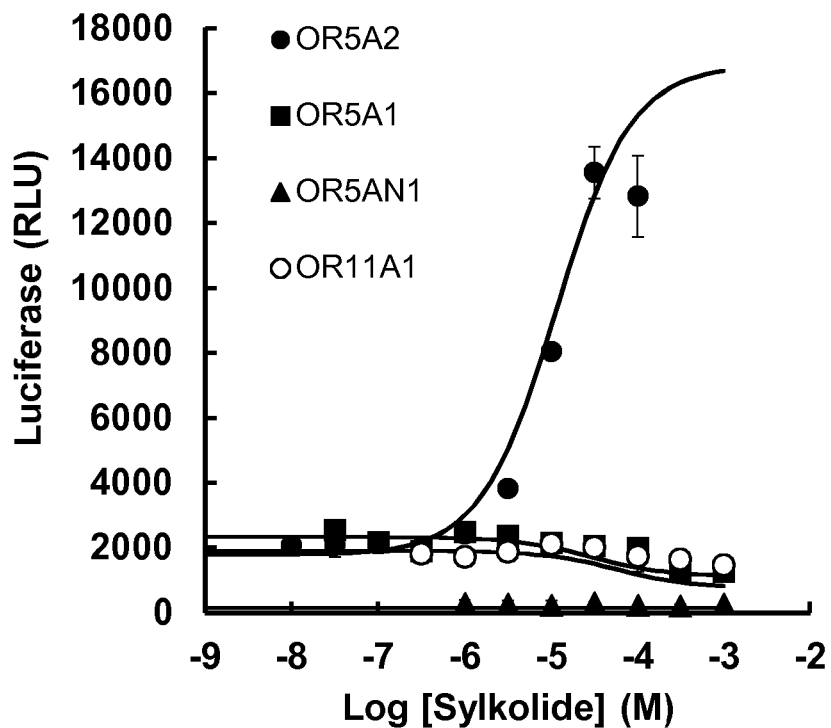
FIG. 8: Dose response curves of (A) Sylkolide and (B) Serenolide on receptors OR5A2, OR5A1, OR5AN1 and OR11A1.
Figure 8:
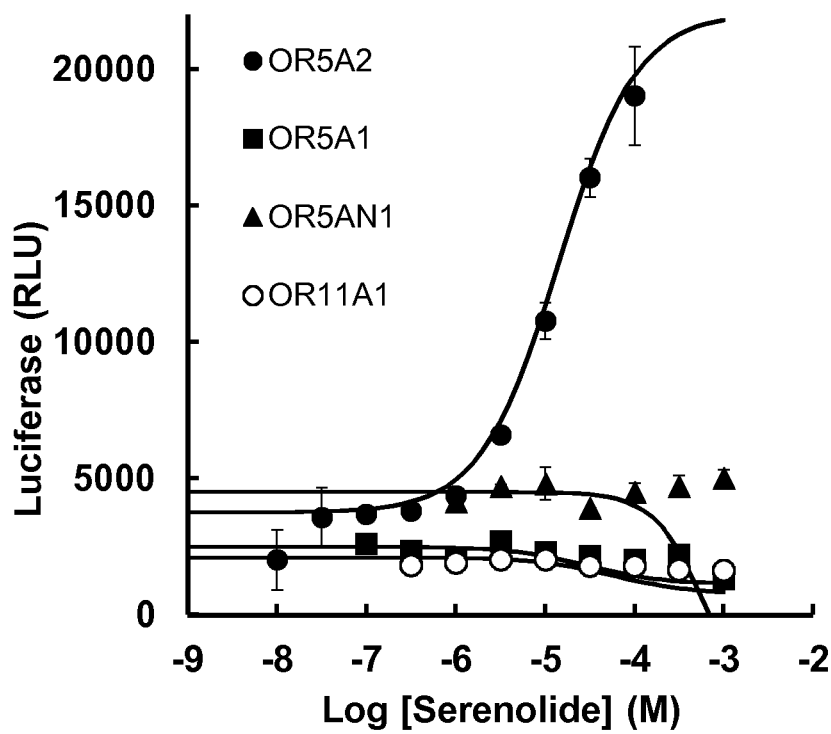
Figure 9:
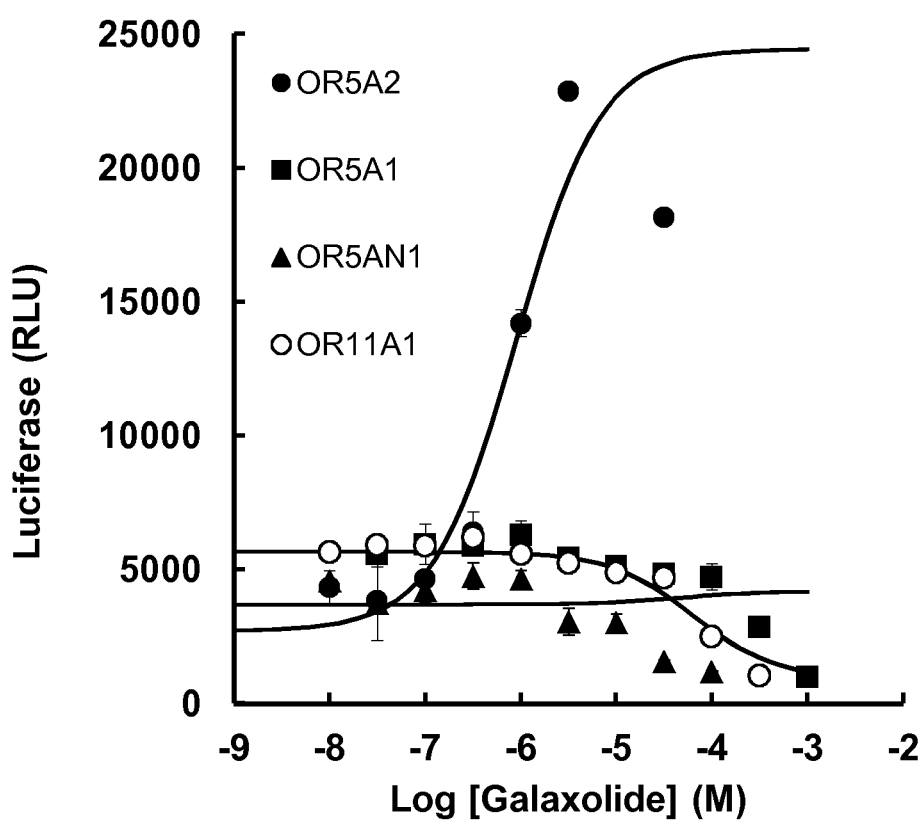
FIG. 9: Dose response curves of (A) Cashmeran, (B) Fixal and (C) Galaxolide® on receptors OR5A2, OR5A1, OR5AN1 and OR11A1.
Figure 10:
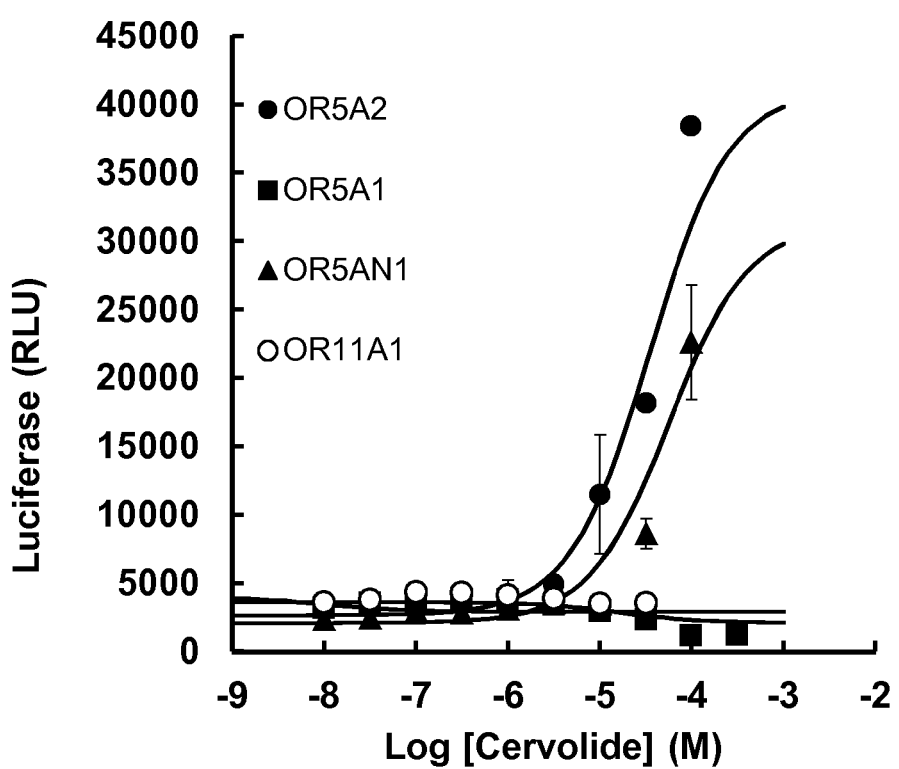
FIG. 10: Dose response curves of (A) Ethylene Brassylate, (B) Ambrettolide and (C) Cervolide on receptors OR5A2, OR5A1, OR5AN1 and OR11A1.

As examples, concentration-response curves of (A) Musk Ambrette and (B) Moskene on receptors OR5A2, OR5A1, OR5AN1, and OR11A1 are illustrated in FIG. 7. Concentration-response curves of (A) Sylkolide and (B) Serenolide on receptors OR5A2, OR5A1, OR5AN1 and OR11A1 are shown in FIG. 8. Concentration-response curves of (A) Cashmeran, (B) Fixal and (C) Galaxolide on receptors OR5A2, OR5A1, OR5AN1 and OR11A1 are shown in FIG. 9. Concentration-response curves of (A) Ethylene Brassylate, (B) Ambrettolide and (C) Cervolide on receptors OR5A2, OR5A1, OR5AN1 and OR11A1 are shown in FIG. 10.

It was observed that OR of the invention (namely OR5A2) is activated by musk compounds belonging to the 4 groups of chemicals described formerly. OR5A1, the closest paralog of OR5A2, was not activated by any of the musk compounds tested. Moreover, musk-specific ORs (OR5AN1 and OR11A1) respond mainly to nitromusks and macrocyclic musks or polycyclic musks and nitromusks respectively (Tables 2). None of the musk compounds tested was able to activate exclusively OR5AN1. Furthermore, our results indicate that the OR of the invention (namely OR5A2) is the only OR activated by the linear musk family, known to be more environment friendly.

The OR of the invention is therefore involved in the perception of all types of musks and constitutes a valuable candidate receptor for identifying a compound that activates, mimics, blocks, inhibits, modulates and/or enhances the perception of musk fragrances.

Example 3: Dose-Responses Analysis of OR11A1 and OR5A1 Specific Ligands —OR Interaction Amino acids sequences alignment shows 67% identity between OR5A1 and OR5A2, 58% with OR5AN1 and 41% with OR11A1 (FIGS. 2A-B). To further address the question of how well paralogy predicts functionality and selectivity, we compared the response of these ORs to beta-ionone and 2-ethyl fenchol, the two well-known agonists of OR5A1 and OR11A1 respectively (Jaeger et al., 2013; Adipietro et al., 2012). These compounds were tested in concentration-response analysis in luciferase assays, as described previously. In each experiment, an empty vector was used as negative control (pEFlBRHO). Representative concentration-response curves are given in FIGS. 3A-B.

It was observed that OR5A1, the closest paralog of OR5A2, and OR11A1 are both activated by their own cognate agonist. On the contrary, in these experimental conditions, OR of the invention (namely OR5A2) as well as OR5AN1 are stimulated neither by beta-ionone nor by 2 ethyl-fenchol, both showing concentration-response curves similar to the empty vector.

Altogether, these results indicate that OR5A1 and OR5A2, although members of the same subfamily, show different agonist specificity (beta-ionone vs musk) indicating that amino acids similarity doesn't robustly predict OR selectivity and functionality among paralogs.

Example 4: Dose-Response Analysis of Ligand —OR Haplotypes Interaction

OR genes are highly variable, with many alleles resulting in differences in smell perception from person to person. These differences can be attributed to genetic variations like, for example, nucleotide polymorphisms. Using the HORDE database (The Human Olfactory Data Explorer, genome.weizmann.ac.il/horde), we found that 5 protein variants (haplotypes) of OR of the invention (namely OR5A2, OR5A2 variant_1) were identified in the population. The most frequent haplotype, present at a frequency of 79,72%, was used in the previous examples (OR5A2-variant_1; SEQ ID NO.1) and is sensitive to musk compounds. The second haplotype, present at 16,59%, encodes a proline to leucine substitution at the position 172 (P172L, OR5A2_variant 2; SEQ ID NO.3). Together, the 2 haplotypes are expressed in more than 96% of the population. Amino acids alignment of the 2 haplotypes are represented in FIG. 4.

To test if the substitution could impact the musk sensitivity, luciferase assays were performed as described previously after transfection of both OR5A2 variants. Cells were treated with semi-logarithmic serial dilutions of musk compounds from the four structurally different groups described earlier. In each experiment, an empty vector was used as negative control (pEFIBRHO). Representative concentration-response curves are given in FIG. 5.

These experimental results indicate that OR5A2_variant 2 is not activated by musk compounds (musk xylene, serenolide, Galaxolide®, velvione, cashmeran, musk ketone), unlike the other haplotype of the receptor of the invention. In these experiments, OR5A2_variant 1 shows concentration-response curves similar to those obtained in example 2. Overall, these observations clearly suggest that the haplotype with the substitution in position 172 (P172L) loses its ability to be activated by musk compounds. This observation could explain why different studies have, so far, excluded the OR of invention as a musk receptor (Shirasu et al. 2014 *Neuron* 81, 165-78; FIG. 5F supplemental, Sato-Akuhara 'N et al. 2016 *J Neurosci.* 36(16), 4482-91).

Example 5: Dose-Response Analysis of Ligand-Chimeric OR5A2_Variant 1 Interaction In 1998, Krautwurst and collaborators have provided a model system for the study of ligand specificity and structure-function relationships for olfactory receptors (Krautwurst et al., 1998 *Cell* 95, 917-26). They showed that ligand recognition by olfactory receptors was largely imparted by the protein region going from transmembrane domain 2 (TM2) to transmembrane domain 7 (TM7). Based on their publication, a chimeric OR5A2_variant 1 olfactory receptor was created containing the TM2-TM7 amino acid sequence of OR5A2_variant 1 flanked by the N-terminal and C-terminal sequence of the olfactory receptor OR2A5 (cf. SEQ ID NO: 12). This chimeric OR5A2_variant 1 receptor shared 86 percent identity with the native OR5A2_variant 1 receptor (FIG. 6A and SEQ ID NO: 10).

To test if the amino acids substitution could impact the musk sensitivity, and specificity and to validate the Krautwurst's model, luciferase assays were performed as described previously after transfection of the chimeric OR5A2_variant 1. Cells were treated with semi-logarithmic serial dilutions of musk compounds from the four structurally different groups described earlier.

In each experiment, an empty vector was used as negative control (pEFIBRHO). Moreover, these cells were treated with beta-ionone and 2 ethyl-fenchol, 2 compounds that are not able to activate the originating OR5A2 receptor (cf. FIG. 2A-B). Representative concentration-response curves are given in FIG. 6 B-C.

Altogether, these results indicate that a chimeric OR5A2_variant 1, although sharing only 86% identity, responds to all types of musks tested. Additionally, the chimeric OR5A2_variant 1 is not activated by beta-ionone or 2 ethyl-fenchol indicating that this chimeric receptor has the same specificity than the OR5A2 receptor and represents a valuable candidate receptor for the identification of compounds that activates, mimics, blocks, inhibits, modulates and/or enhances the perception of musk fragrances.

TABLE 1 complete list of odorant molecules tested on the OR of the invention:

| | | | |
|---|---|---|---|
| VANILLIN #1 | CEDROXYDE | DIMETHYL | GUAIYL |
| VANILLIN #2 | CEDRYL | OCTENONE | ACETATE |

TABLE 1-continued complete list of odorant molecules tested on the OR of the invention:

| | | | |
|---|---|---|---|
| FENCHONE (+) | ACETATE | DIMETHYL | HELVETOLIDE |
| ROSE OXIDE | LIQUID | PHENYL | HEPTAL- |
| (−) | CETALOX | ETHYL | ACTONE |
| 2,3- | CETONAL | CARBINOL | GAMMA |
| DIMETHYL- | CETONE V | DI- | HERBAVERT |
| PYRAZINE | CINNAMYL | MYRCETOL | HERCOLYN |
| ACETAL CD | CINNAMATE | DIONE | DE |
| ACETAL R | DISTILLED | DIPENTENE | HEXENOL-2- |
| ACETATE PA | CITRAL | DODECAL- | TRANS |
| ACETOIN | DIMETHYL | ACTONE | HEXENYL |
| ACETYL | ACETAL | DELTA | ACETATE |
| CARYO- | CITRONELLYL | DODECAL- | CIS & TRANS |
| PHYLLENE | ISOBUTYRATE | ACTONE | HEXENYL-3- |
| ADOXAL | CITRONELLYL | GAMMA | CIS |
| ALCOHOL | OXYACET- | ELINTAAL | BENZOATE |
| C 6 | ALDEHYDE | ETHYL | HEXENYL-3- |
| HEXYLIC | CITRONELLYL | BENZOATE | CIS |
| ALDEHYDE | PROPIONATE | ETHYL | BUTYRATE |
| C 9 | CLARITONE | CAPRYLATE | HEXENYL- |
| ISONONYLIC | CLONAL | ETHYL | 3-CIS |
| ALLYL | CONIFERAN | CINNAMATE | HEXENOATE |
| CAPROATE | CORANOL | ETHYL | HEXENYL-3- |
| AMBRINOL | COUMAREX | ISOAMYL | CIS |
| AMYL | I MOD | KETONE | ISOBUTYRATE |
| BENZOATE | CYCLE- | ETHYL | HEXYL |
| AMYL | MONE A | LINALOOL | BENZOATE |
| PHENYL | CYCLO- | ETHYL | HEXYL |
| ACETATE | GALBANATE | LINALYL | BUTYRATE |
| APHERMATE | CYCLOHEXYL | ACETATE | HEXYL |
| AURANTIOL | ETHYL | ETHYL | PROPIONATE |
| PURE | ACETATE | METHYL-2- | HYDRA- |
| BENZYL | CYCLOHEXYL | BUTYRATE | TROPIC |
| ACETONE | SALICYLATE | ETHYL | ALDEHYDE |
| BENZYL | CYMENE | OENANTH- | DIMETHYL |
| BENZOATE | PARA | ATE | ACETAL |
| BENZYL | DECAL- | ETHYL | HYDROXY- |
| BUTYRATE | ACTONE | PEL- | CITRONELLAL |
| BENZYL | DELTA | ARGONATE | DIMETHYL |
| ISOBUTYRATE | DECAL- | ETHYL | ACETAL |
| BENZYL | ACTONE | PROPIONATE | INDOFLOR |
| METHYL | GAMMA | ETHYL | INDOLENE |
| ETHER | DECATONE | SALICYLATE | IRALIA PURE |
| BENZYL | DECENAL-4- | FARNESENE | IRONE F |
| PHENYL | TRANS | FENCHONE | ISO |
| ACETATE | DELTA-3 | ALPHA | JASMONE FR |
| BERRYFLOR | CARENE | FLORAMAT | ISOAMYL |
| BISABOLENE | DIBENZYL | FLOROPAL | BUTYRATE |
| BOISIRIS | ETHER | FOLENOX | FR |
| BORNYL | DIHYDRO | FOLIONE | ISOBORNYL |
| ACETATE | AMBRATE | FOLROSIA | ISOBUTYRATE |
| LIQUID | DIHYDRO | FRESKO- | ISOBUTYL |
| BUTYL | LINALOOL | MENTHE | ISOBUTYRATE |
| ACETATE | DIHYDRO | GALBANONE | ISOBUTYL |
| BUTYL | TERPINEOL | PURE | PHENYL |
| HYDROXY | DIMETHYL | GERANYL | ACETATE |
| TOLUENE | ANTHRANIL- | ACETONE | ISOBUTYL |
| CASSIONE | ATE | GERANYL | SALICYLATE |
| FIRMENICH | DIMETHYL | ISOBUTY- | ISOCYCLO- |
| CEDRENE | BENZYL | RATE | CITRAL |
| WASHED | CARBINOL | GRISALVA | ISONONANOL |
| ISOPROPYL | DIMETHYL | TETRA- | ISONONANYL |
| MYRISTATE | BENZYL | HYDRO | ACETATE |
| ISOPROPYL | CARBINYL | CITRAL | PURE |
| QUINOLINE | BUTYRATE | TRIACETIN | ISOPENTY- |
| ISOPULEGOL | NEROLIONE | TRIETHYL | RATE |
| JASMOL- | NERYL | CITRATE | ISOPROPYL |
| ACTONE | ACETATE HC | VELOUTONE | ALCOHOL |
| JASMONE CIS | NON- | VERDALIA | CANTHOXAL |
| JASMONYL | ADIENOL-2,6 | VERDANTIOL | LILIAL |
| JASMO- | NOPYL | VERN- | MEFRANAL |
| PYRANE | ACETATE | ALDEHYDE | CARYO- |
| FORTE T | OCTA- | VERTOFIX | PHYLLENE |
| KOHINOOL | LACTONE | COEUR | HYDROGEN |
| LAITONE | GAMMA | VETIVERYL | SULPHIDE |
| LEAF ACETAL | ONCIDAL | ACETATE | METHANE- |
| LIFFAROME | ORIVONE | VETYNAL | THIOL |
| GIV | OXY- | VIOLIFF | BENZYL |

TABLE 1-continued complete list of odorant molecules tested on the OR of the invention:

| | | | |
|---|---|---|---|
| LIME OXIDE | OCTALINE | VIRIDINE | MERCAPTAN |
| LIMETOL | FORMATE | AQUAN- | 3-MERCAPTO- |
| LINALOOL | PARSOL 1789 | TRAAL | 2-METHYL- |
| OXIDE | PEOMOSA | (FLEUR- | 1-BUTANOL |
| LINALYL | PERANAT | ANTIOL) | 3-MERCAPTO- |
| CINNAMATE | PHENOXY | ARBOROMA | 3-METHYL- |
| LINALYL | ETHYL | AVALONE | 1-HEXANOL |
| FORMATE | ALCOHOL | CARYO- | 2-MERCAPTO- |
| LINALYL | PHENYL | PHYLLENE | ACETIC ACID |
| ISOBUTYRATE | ETHYL | ALCOHOL | DIMETHYL |
| LINALYL | FORMATE | CISTULAC | SULPHIDE |
| PROPIONATE | PHENYL | CORNOLINE | DIALLYL |
| MAGNOLAN | ETHYL | DECYL | SULPHIDE |
| MALTYL | ISOVALERATE | ACETATE | 1- |
| ISOBUTYRATE | PHENYL | ETHYL 2- | BUTYLAMINE |
| MENTHANYL | ETHYL | PHENYL- | TRIMETHYL- |
| ACETATE | SALICYLATE | BUTYRATE | AMINE |
| METHYL | CRYSTALS | INONYL | 1,5-DIAMINO- |
| CAMOMILLE | PHENYL | FORMATE | PENTANE |
| METHYL | PROPYL | INONYL | INDOLE |
| CINNAMIC | ACETATE | PROPIONATE | SKATOLE |
| ALDEHYDE | PHENYL | MEVAN- | 3-METHYL-2- |
| METHYL | PROPYL | TRAAL | HEXENOIC |
| DIPHENYL | ALCOHOL | OCTYL | ACID* |
| ETHER | PINOACET- | ACETATE | 3-HYDROXY- |
| METHYL | ALDEHYDE | PRENYL | 3-METHYL- |
| HEPTENONE | POIRENATE | BENZOATE | HEXANOIC |
| PURE | PRENYL | PROPYL- | ACID |
| METHYL | ACETATE | IDENE | (E),(E)-2,4- |
| LINOLEATE | PROPYL | PHTHALIDE | DECADIENAL |
| METHYL | DIANTILIS | FLEURANIL | GEOSMIN |
| PHENYL | RADJANOL | UNDECA- | AMMONIA |
| ACETATE | SUPER | TRIENE | ZINARINE |
| MILK | RHUBOFIX | CIS-3- | 1-CYCLO- |
| LACTONE 2067 | RHUBOFLOR | HEXENYL | HEXYL- |
| MUSCONE | ROSAPHEN | PROPIONATE | ETHANOL |
| MYRALDYL | RUM ACETAL | CIS-3- | 1-CYCLO- |
| ACETATE | SCENTENAL | HEXENYL- | HEXYLETHYL |
| NEROLIDOL | STYRALLYL | TIGLATE | ACETATE |
| EXTRA | PROPIONATE | CITRO- | 1-CYCLO- |
| NEROLIDOL | SYVERTAL | NELLOL | HEXYLETHYL |
| SYNTHETIC | TANGERINOL | LINALOOL | BUTYRATE |
| NEROLIDYLE | TERPINENE | MENTHONE | 1-CYCLO- |
| AMBROFIX | GAMMA | UNDECA- | HEXYLETHYL |
| ANAPEAR | TERPINOLENE | VERTOL | PROPIONATE |
| ANJERUK | METHYL | VERDYL | 10- |
| AZURONE | CINNAMATE | ACETATE | UNDECENAL |
| BELAMBRE | METHYL | VERDYL | 10- |
| BENZYL | DIHYDRO- | PROPIONATE | UNDECENOL |
| CINNAMATE | JASMONATE | YARA-YARA | 10-UN- |
| BENZYL | METHYL | TONALIDE | DECYLENIC |
| SALICYLATE | SALICYLATE | GALAXO- | ACID |
| BETA-PINENE | METHYL | LIDE ® | ARGARBOIS |
| BOURGEONAL | UNDECA- | THIBE- | ALDE- |
| CAMONAL | NOATE | TOLIDE | HYDE MNA |
| CIS-3- | MUSK R1 | MUSK | FURNISAL |
| HEXENYL | NECTARYL | KETONE | EMPETAL |
| ACETATE | NIRVANOLIDE | MUSK | SUPER |
| CIS-3- | OPALAL | XYLENE | MUGUET |
| HEXENYL | PANDANOL | CASHMERAN | GERANIOL |
| SALICYLATE | PARADIS- | AMBRET- | GERANYL |
| CITRAL | AMIDE | TOLIDE | ACETATE |
| COSMONE | P-CRESYL | ETHYLENE | CITRONELLYL |
| CYPRISATE | METHYL | BRASSYL- | ACETATE |
| DIHEXYL | ETHER | ATE | NEROL |
| FUMARATE | PEONILE | HAB- | PHENYL- |
| DIHYDRO- | PEPPERWOOD | ANOLIDE | ETHANOL |
| FARNESAL | PHARAONE | VELVIONE | PHENYL |
| DIHYDRO- | POMAROSE | EXALTOLIDE | ETHYL |
| MYRCENOL | RADJANOL | MUSK MC4 | ACETATE |
| DIHYDRO- | ROSSITOL | MUSCENONE | TETRA- |
| MYRCENYL | SERENOLIDE | HEXA- | HYDRO- |
| ACETATE | SINODOR | DECANOL- | GERANIOL |
| DUPICAL | SPIRO- | IDE | TETRA- |
| ETHYLENE | GALBANONE | CYCLO- | HYDRO- |
| GLYCOL | STEMONE | PENTA- | LINALOOL |
| MONOPHEN- | SUPER | DECANONE | BENZO- |
| OXYACETATE | MUGUET | MUSK R1 | PHENONE |
| FARNESOL | TANAISONE | CERVOLIDE | DIPHENYL |
| FLORIDILE | A-TERPINYL | TRASEOLIDE | OXIDE |
| FLORYMOSS | ACETATE | NIRVAN- | ROSE OXIDE |
| Γ-UNDECA- | TETRA- | OLIDE | 9-DECEN-1-OL |
| LACTONE | HYDRO- | MOXALONE | DIMETHYL |
| GEORGY- | LINALYL | FREESIOL | BENZYL |
| WOOD | ACETATE | FLOROSA | CARBINYL |
| GERANODYLE | THIBETOLIDE | HYDROXY- | ACETATE |
| HELIOTROPIN | TONKAROSE | CITRO- | MEFROSOL |
| ISOBUTAVAN | TRIDEC-2- | NELLAL | ETHYL |
| ISORALDEINE | ENE NITRILE | CYCLAMEN- | SAFRANATE |
| LIMONENE | TRIMOFIX | ALDEHYDE | PIVAROSE |
| METHYL 10- | ULTRAVANIL | LYRAL | ANTHER |
| UNDECYLEN- | UNDECANAL | MAJANTOL | HINDINOL |
| ATE | UNDECANOIC | MAYOL | POLYSANTOL |
| HELIONAL | ACID | SILVIAL | SANDALORE |
| L-CARVONE | UNDECANOL | FLOR- | EBANOL |
| D-CARVONE | DIETHYL | HYDRAL | OSYROL |
| 1-NONANOL | MALONATE | CITRO- | JAVANOL |
| INDOCLEAR | ETHYL | NELLYL | ISOBORNYL- |
| PHENYL- | ACETO- | NITRILE | CYCLO- |
| ACETIC ACID | ACETATE | GERANYL | HEXANOL |
| BORNEOL | HEXYL | NITRILE | CALONE |
| Δ-UNDECAL- | ACETATE | HYPO-LEM | MARENIL |
| ACTONE | ISOAMYL | LEMONILE | MELONAL |
| PIVACYCLENE | ACETATE | MYRCENYL | FLORALO- |
| NEO- | B-PHENOXY- | ACETATE | ZONE |
| CASPIRENE | ETHYLISO- | A-TERPINYL | MACEAL |
| BUCCOXIME | BUTYRATE | ISO- | PHELL- |
| LABIENOXIME | RASPBERRY | BUTYRATE | ANDRENE |
| ETHYL | KETONE | METHYL | SAFRALEINE |
| HEXANOATE | ETHYL | PAMPLE- | ETHYL- |
| ETHYL | BUTYRATE | MOUSSE | VANILLIN |
| METHYL | PEAR ESTER | RHUBA- | MALTOL |
| PHENYL | AMBER | FURAN | ETHYL- |
| GLYCIDATE | KETAL | THIO- | MALTOL |
| ETHYL | AMBERMAX | TERPINEOL | LEVISTAMEL |
| PHENYL | CEDRAMBER | NOOT- | COUMARIN |
| GLYCIDATE | KARANAL | KATONE | PARA- |
| NON- | AMBRO- | ALICATE | METHYL- |
| ALACTONE | CENIDE | DECANAL | ACETO- |
| OCTAHYDRO- | AMBERCORE | FRESCILE | PHENONE |
| COUMARIN | MET- | LINALYL | PARA- |
| A- | AMBRATE | ACETATE | METHOXY- |
| DAMASCONE | OKOUMAL | MANDARINE | ACETO- |
| B- | SPIR- | ALDEHYDE | PHENONE |
| DAMASCONE | AMBRENE | VETIKOL | METHYL |
| Δ- | CIS-3- | ACETATE | EPI- |
| DAMASCONE | HEXENOL | 9-DECENAL | JASMONATE |
| DAM- | 2,6- | UNDECENE- | AMYL |
| ASCENONE | NONADIENAL | 2-NITRILE | CINNAMIC |
| MANZANATE | METHYL | EUGENOL | ALDEHYDE |
| APPLINAL | OCTYNE | ISOEUGENOL | HEXYL |
| ORTHOLATE | CARBONATE | METHYL- | CINNAMIC |
| ALLYL AMYL | STYRRALLYL | ISOEUGENOL | ALDEHYDE |
| GLYCOLATE | ACETATE | BENZYL- | DIHYDROISO- |
| ALLYL | DYNASCONE | ISOEUGENOL | JASMONATE |
| CYCLO- | RESEDA | FORTE | BENZYL |
| HEXYL- | BODY | DIHYDRO- | ACETATE |
| PROPIONATE | LIGUSTRAL | EUGENOL | BENZYL |
| ALLYL | VERDORA- | METHYL | PROPIONATE |
| HEPTANOATE | CINE | DIANTILIS | DIHYDRO- |
| FRUITATE | CHRYS- | CINNAMIC | JASMONE |
| FRUTONILE | ANTHAL | ALCOHOL | JESSATE |
| HERBANATE | BEAU- | CINNAM- | QUINTONE |
| METHYL | VERTATE | ALDEHYDE | JASMATONE |
| LAITONE | PETIOLE | CINNAMYL | HEPTONE |
| ETHYL | VERDILYN | NITRILE | JASMA- |
| LAITONE | PHENYL- | CUMIN- | CYCLENE |
| GIVESCONE | ACET- | ALDEHYDE | ISOBORNYL |
| PLICATONE | ALDEHYDE | CUMIN | ACETATE |
| TERPINEN- | GARDAMIDE | NITRILE | CAMPHOR |
| 4-OL | VETHYMINE | ANETHOLE | CARVACROL |
| THUJONE | CITRONELLAL | DIHYDRO- | 1,8-CINEOLE |
| THYMOL | GARDO- | ANETHOLE | CISTULATE |
| METHYL | CYCLENE | TOSCANOL | CRESS- |
| BENZOATE | ROSACETOL | METHYL- | ANTHER |
| α-IONONE | CEDROL | CHAVICOL | HERBOXANE |

TABLE 1-continued complete list of odorant molecules tested on the OR of the invention:

β-IONONE
α-ISO-METHYL-IONONE
α-IRONE
DIHYDRO-β-IONONE
VIOLET NITRILE
ROSYRANE
CIS-3-HEXENYL TIGLATE
PELARGENE
METHYL TUBERATE
DISPIRONE
ANIS-ALDEHYDE
ANISIC ALCOHOL
ANISIC NITRILE
α-TERPINEOL
BENZYL ALCOHOL
NEROLIN
METHYL NAPHTHYL KETONE
HYDRA-TROPIC ALDEHYDE
PROPYLENE GLYCOL ACETAL
FLORO-CYCLENE
METHYL ANTHRANIL-ATE
CALYXOL
GYRANE
HEXYL SALICYLATE
AMYL SALICYLATE
GLYCOL-IERRAL
FLORANE
GERANYL BENZOATE
2,3-HEPTANE-DIONE
4-HEPTANONE
ⓘ-6-HEXADECEN-LACTONE
HEXANAL
HEXANOIC ACID
TRANS-2-HEXENAL, NATURAL
CIS-3-HEXEN-1-OL
HEXYL OCTANOATE
LAURIC ACID
LAURIC ALDEHYDE
(R)-(+)-LIMONENE
MALTOL
L-MENTHOL
L-MENTHONE
METHYL ACETATE
METHYL CEDRYL KETONE
FELVINONE
AZARBRE BOIS-AMBRENE
TIMBEROL
KEPHALIS
KOAVONE
AMBORYL ACETATE
ISO-LONG-IFOLANONE
CYCLISONE
ISOAMBOIS
PTBCHA
PTBCHA HIGH CIS
EVERNYL
ISOBUTYL-QUINOLENE
TETRAHYDRO NAPHTHOL
O-CRESOL
PROPENYL-GUAETHOL
2-COUMARONE
ACETAL
ACET-ALDEHDYE
ACET-ALDEHYDE, 50 WT. % SOLUTION IN ETHANOL
ANIMONIUM UULFIDE
3-METHYL-1-BUTANOL
ISOAMYL BENZOATE
ⓘ-ARNYL-CINNAN-ALDEHYDE
ISOAMYL CINNAMATE
ⓘ-AMYL-CINNAMYL ALCOHOL
ISOAMYL FORMATE
OCTYL ISOBUTYRATE
OCTYL PROPIONATE
OLEIC ACID
ⓘ-PENTADEC-ALACTONE
2,3-PENTANE-DIONE
2,3-PENTANE-DIONE, NATURAL
4-PENTENOIC ACID
PHENETHYL CINNAMATE
PHENETHYL 2-FUROATE
PHENOXY-ACETIC ACID
1-PHENYL-3-METHYL-3-PENTANOL
2-PHENYL-
AMYL 2-FUROATE
AMYL HEXANOATE
ISOAMYL LAURATE
AMYL OCTANOATE
ISOAMYL OCTANOATE
ISOAMYL SALICYLATE
ISOAMYL ISOVALERATE
ANISYL ACETATE
BENZ-ALDEHYDE
BENZOIC ACID
ISOBORNEOL
2-BUTANONE
ISOBUTYL ACETO-ACETATE
ISOBUTYL ALCOHOL
ISOBUTYL BENZOATE
BUTYL BUTYRIL-ACETATE, NATURAL
BUTYL FORMATE
BUTYL LAURATE
BUTYL LEVULINATE
ⓘ-ISO-BUTYLPHEN-ETHYL ALCOHOL, NATURAL
ISOBUTYL PROPIONATE
BUTYL 10-UNDECENO-ATE
ISOBUTYR-ALDEHYDE
BUTYRIC ACID
ISOBUTYRIC ACID
TRIBUTYRIN
(+)-CAMPHENE
4-CARVO-MEN-THENOL, NATURAL
D-CARVONE
CINNAM-ALDEHYDE
CINNAMYL ACETATE
VANILLIN (SIGMA)
2-ACETYL-PYRAZINE
BUTYL-AMINE
2-ISOBUTYL-3-METHOXY-PYRAZINE
2-ISOBUTYL-
D-LIMONENE
MENTHOL
MYRCENE
OCIMENE
α-PINENE
COGNAC OIL
P-CRESOL
CYCLO-HEXANE-ACETIC ACID
CYCLO-HEXYL ACETATE
P-CYMENE
HEXANAL
ⓘ-DEC-ALACTONE
DIETHYL MALATE
DIETHYL MALONATE
DIETHYL SEBACATE
DIETHYL L-TARTRATE
DIHYDRO-CARVEOL
P-DIMETH-OXYBENZENE
2,6-DIMETHYL-5-HEPTENAL
DIMETHYL SUCCINATE
ETHYL ACRYLATE
ETHYL P-ANISATE
ETHYL ISOBUTYRATE
ETHYL MYRISTATE
ETHYL NONANOATE
ETHYL PALMITATE
ETHYL PYRUVATE
ETHYL TIGLATE
ETHYL VALERATE
ETHYL ISOVALERATE
EUCALYPTOL
EUGENOL
LSOEUGENOL
METHYL EUGENOL
METHYL ISOEUGENOL
FENCHYL ALCOHOL
FURFURYL GERANIUM OIL
PHENE-THYLAMINE
2-PHENYL-2-BUTENAL
1-PHENYL-1,2-PROPANE-DIONE
STYRENE
TETRA-HYDRO-4-RNETHYL-2-

METHYL P-ANISATE
4-METHYL-ANISOLE
ⓘ-METHYL-BENZYL ALCOHOL
METHYL BUTYRATE
METHYL 2-FUROATE
METHYL LAURATE
METHYL 2-METHYL-BUTYRATE
METHYL 3-(METHYL-THIO) PROPIONATE
METHYL B-NAPHTHYL KETONE
METHYL PHENYL-ACETATE
METHYL ISOVALERATE
2-METHYL-PENTANOIC ACID
ⓘ-NONAL-ACTONE
NONYL ACETATE
OCTANOIC ACID
4-HEXEN-3-ONE
HEXYL TRANS-2-BUTENOATE
ⓘ-NONAL-ACTONE
4-(METHYL-THIO)-2-BUTANONE
SAFRANAL
FENCHYL ACETATE
3-ETHYL-PYRIDINE
FURFURYL OCTANOATE
2-HEPTYL-FURAN
2-LSOPROPYL-5-METHYL-2-HEXENAL
3-OCTEN-2-OOE
3-PENTEN-2-ONE
2-UNDECENAL
ETHYL 3-HYDROXY-BUTYRATE ISOBUTYL TRANS-2-BUTENOATE
2-METHOXY-3-ISOBUTYL-PYRAZINE
3-(METHYL-THIO)-1-HEXANOL
HEXYL
PROPION-ALDEHYDE (1S)-(−)-ⓘ-PINENE
(1S)-(−)-ⓘ-PINENE
PIPERINE
PIPERONAL, NATURAL
PRPIONO-ALDEHYDE
1-PROPANOL
P-LSOPROPYL-BENZYL ALCOHOL
ISOPROPYL BUTYRATE
PROPYL ISO-BUTYRATE
PROPYL HEXANOATE
LSOPULEGYL ACETATE
PYRUV-ALDEHYDE
SALICYL-ALDEHYDE
ⓘ-TERPINEOL
TETRA-HYDRO-FURFURYL ALCOHOL
THYMOL
P-TOLYL ACETATE
P-TOLYL PHENYL-ACETATE
UNDECANAL
VALER-ALDEHYDE
VALERIC ACID
ETHYL UNDECANO-ATE
2-, 3-; AND 10-MERCAPTO-PINANE
2-METHYL-BUTYL ISOVALERATE
1,9-NONANE-DITHIOL
1,8-OCTANE-DITHIOL
OCTYL 2-FUROATE
PROPYL MERCAPTAN
PYRROLIDINE 3,5,5-TRIMETHYL-HEXANAL
3-ACETYL-2,5-DIMETHY-LTHIOPHENE
1,3 BUTANE-DITHIOL
CYCLO-HEXANE-CARBOCYLIC ACID
3-DECEN-2-ONE
3-HEPTANOL
THIAZOLE 2,2'-(DITHIO-DIMETHYL-ENE) DIFURAN
ETHYL TRANS-2, CIS-4-DECA-DIENOATE
2-ETHYL-3,5-DIMETHYL-PYRAZINE
5-ETHYL-3-HYDROXY-4-METHYL-2(5H)-FURANONE
2-ETHYL-3-METHYL-PYRAZINE
P-ETHYL-PHENOL
FURFURYL METHYL SULFIDE
2-FURYL METHYL KETONE
TRANS-2-HEPTENAL
3,4-HEXANE-DIONE
3-HEXENOIC ACID
HEXYL ISO-BUTYRATE
4-HYDROXY-2,5-DIMETHYL-3(2H)-FURANONE
P-MENTHA-8-THIOL-3-ONE
2-MERCAPTO-PROPIONIC ACID
2-METHOXY-3-METHYL-PYRAZINE
3-METHYL-CROTONIC ACID
2-METHYL-3-FUR-ANTHIOL
1-METHYL-NAPHTHAL-ENE
TRANS-2-METHYL-2-PENTENOIC ACID
5-METHYL-2-PHENYL-2-HEXENAL
4-METHYL-2-PHENYL-2-PENTENAL
METHYL PROPYL DISULFIDE
4-METHYL-5-THIAZOLT-ETHANOL
(2.METHYL-2-PROPEN-1-YL) PYRAN UNDECANOIC ACID
2,6-XYLENOL
2-ACETYL-PYRIDINE
CIS-4-DECENAL
4,5-DIHYDRO-3(H)THIO-PHENONE
2,4-DIMETHYL-5-ACETYL-THIAZOLE
3,5-DIMETHYL-1,2-CYCLO-PENTADIONE
TRIMETHYL DISULFIDE
ETHYL 2-MERCAPTO-PROPIONATE
FURFURYL 3-METHYL-BUTANOATE
1-FURFURYL PYRROLE
CIS-4-HEPTENAL
4-HYDROXY-BUTANOIC ACID LACTONE
ⓘ-UNDECAL-ACTONE
2-METHOXY-PYRAZINE
5H-5-METHYL-6,7-DIHYDRO-CYCLOPENTA-[B]PYRAZINE
2-METHYL-PYRAZINE
2-NAPH-THALENE-THIOL
5,6,7,8-TETRA-HYDROQUIN-OXALINE
2-ACETYL-3,5(OR 6)-DIMETHYL-PYRAZINE
3-BUTYL-IDENE-PHTHALIDE
ETHYL TRANS-3-HEXENOATE
HEPTANOIC ACID
4-HYDROXY-BENZ-ALDEHYDE
SYRING-ALDEHYDE
CITRO-NELLYL TIGLATE
DIACETIN

TABLE 1-continued complete list of odorant molecules tested on the OR of the invention:

| | | | |
|---|---|---|---|
| PHENYL-ACETATE | α-TERPINENE | ACETATE | ISOBUTYL |
| 2-ISOPROPYL-PHENOL | 1,3-PROPANE-DITHIOL | LSOPENTYL-AMINE | TIGLATE |
| 4-METHYL-PENTANOIC ACID | 2,5-XYLENOL | 2-METHYL-BUTYL ACETATE | HEXYL TIGLATE |
| 1-BUTANE-THIOL | 4-(METHYL-THIO) BUTANOL | 3-METHYL-2-BUTEN-1-OL | METHYL TIGLATE |
| ETHYL TRANS-2-BUTENOATE | D-XYLOSE | 4-PROPYL-PHENOL | FURFURYL BUTYRATE |
| ETHYL MALTOL | 2-ACETYL-5-METHYL-FURAN | 4-ALLYL-2,6-DIMETHOXY-PHENOL | FURFUTYL HEPTENOATE |
| ETHYL 2-METHYL-PENTANOATE | 2,5-XYLENOL THIAZOLE BENZENE-THIOL | 2,5-DI-METHYL-4-METHOXY-3(2H) FURANONE | METHYL STEARATE METHYL DECANOATE |
| ETHYL STEARATE | DI-HYDRO-IONONE | 1-ETHYL-HEXYL TIGLATE | METHYL (P-TOLYLOXY) ACETATE |
| | PHENETHYL 2-METHYL-BUTYRATE | ISOPROPYL 2-METHYL-BUTYRATE | FENCHONE (-) |
| | 4,5-DIMETHYL-3-HYDROXY-2,5-DIHYDRO-FURAN-2-ONE | METHYL 2-METHYL-PENT-ANOATE | 3-METHYL-3-PENTANOL ACETO-VANILLONE |
| | | METHYL NICOTINATE | 2-BUTANOL ETHYL (±)-2-HYDROXY-CAPROATE |
| | | METHYL 3-NONENOATE | α-BROMO-STYRENE, MIXTURE OF ISOMERS |
| | | METHYL TRANS-2-OCTENOATE | TRIDECANAL TETRAHYDRO MYRCENOL DIETHYL PHTALATE |
| | | METHYL SORBATE | GALAXOLIDE 1,4-BUTANE-DITHIOL |
| | | ANISYL PHENYL-ACETATE | L/-MENTHYL LACTATE |
| | | VANILLIN ISO-BUTYRATE | MENTHAL-ACTONE |
| | | OCTA-HYDRO-COUMARIN | 2-PENTANE-THIOL |
| | | 2-ACETYL-2-THIAZOLINE | 3-CARENE |
| | | ISOPROPYL DISULFIDE | 1,4-DITHIANE |
| | | ETHYL METHYL SULFIDE | 2,6-DI-METHYL-THIOPHENOL |
| | | 2-PENTYL BUTYRATE | |

TABLE 2 complete list of musk compounds tested on the OR of the invention, OR5A1, OR5AN1, OR11A1
(Non Active represents negative experiments, no activation after testing)

| Name | Organoletic properties | Structure | Class | OR5A2 | OR5A1 | OR5AN1 | OR11A1 |
|---|---|---|---|---|---|---|---|
| Moskene | sweet musk ambrette ketone powdery dry | 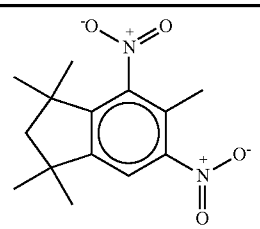 | Nitro Musk | −5.73 | Non Active | Non Active | Non Active |
| Musk ketone | fatty musk soapy dry powdery | 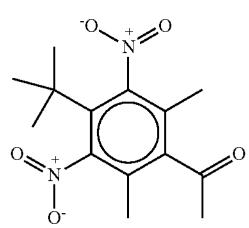 | Nitro Musk | −3.97 | Non Active | −6.54 | Non Active |
| Musk xylol | fatty dry sweet soapy musk | 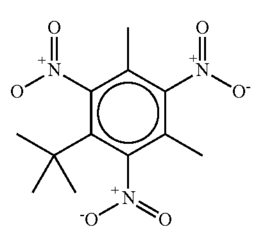 | Nitro Musk | −5.73 | Non Active | −6.18 | −5.73 |

TABLE 2-continued complete list of musk compounds tested on the OR of the invention, OR5A1, OR5AN1, OR11A1
(Non Active represents negative experiments, no activation after testing)

| Name | Organoletic properties | Structure | Class | OR5A2 | OR5A1 | OR5AN1 | OR11A1 |
|---|---|---|---|---|---|---|---|
| Musk ambrette | musty sweet ambrette seed | 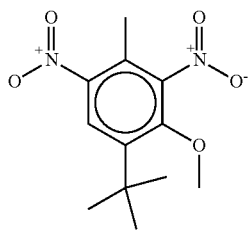 | Nitro Musk | −5.06 | Non Active | −3.16 | Non Active |
| Ethylene brassylate | powdery sweet floral ambrette musk woody | 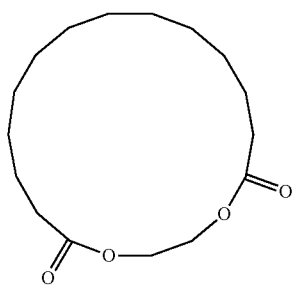 [SMILES: O=C1CCCCCCCCCCCCC(=O)OCCO1] | Polycyclic | −4.31 | Non Active | −4.18 | Non Active |
| Thibetolide = Exaltolide | musk animal powdery natural fruity | 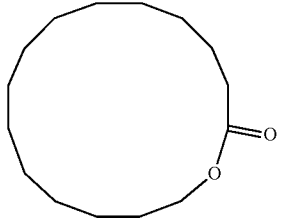 [SMILES: O=C1CCCCCCCCCCCCCCO1] | Polycyclic | −4.36 | Non Active | −4.06 | Non Active |
| 1,16-Hexadecalactone | sweet musk balsam amber animal | 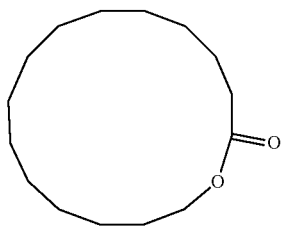 | Polycyclic | −4.39 | Non Active | −3.49 | Non Active |
| Exaltenone | musk animal natural musk floral | 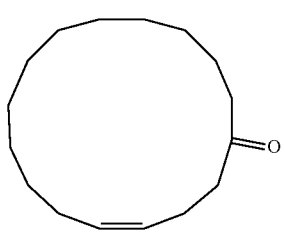 [SMILES: O=C1CC/C=C\CCCCCCCCCCC1] | Polycyclic | −4.81 | Non Active | −5.73 | Non Active |
| Globanone (Animusk) | musk floral | 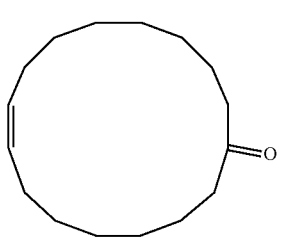 [SMILES: O=C1CCCCCC/C=C\CCCCCCC1] | Polycyclic | −5.4 | Non Active | −5.65 | Non Active |

TABLE 2-continued complete list of musk compounds tested on the OR of the invention, OR5A1, OR5AN1, OR11A1
(Non Active represents negative experiments, no activation after testing)

| Name | Organoletic properties | Structure | Class | OR5A2 | OR5A1 | OR5AN1 | OR11A1 |
| --- | --- | --- | --- | --- | --- | --- | --- |
| Musk R1 | sweet oily incense musk amber animal | 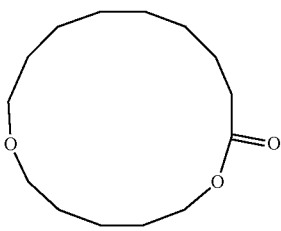 [SMILES: O=C1CCCCCCCCOCCCCCO1] | Polycyclic | −4.72 | Non Active | −4.02 | Non Active |
| Velvione | dry powdery musk amber civet | 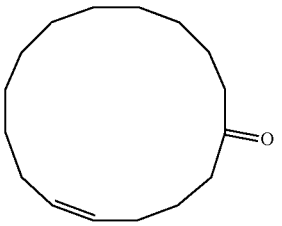 [SMILES: O=C1CCC/C=C\CCCCCCCCCC1] | Polycyclic | −4.54 | Non Active | −4.31 | Non Active |
| Cyclopentadecanone | powdery musk animal natural greasy | 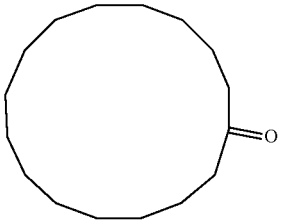 [SMILES: O=C1CCCCCCCCCCCCCCC1] | Polycyclic | 6 | Non Active | −4.95 | Non Active |
| Muscone | sweet musk animal powdery fatty natural | 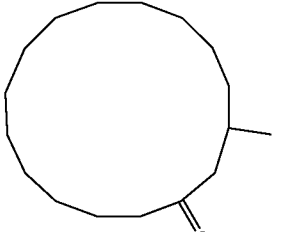 | Polycyclic | −5.25 | Non Active | −5.37 | Non Active |
| Civetone | clean musk dry animal sweet | 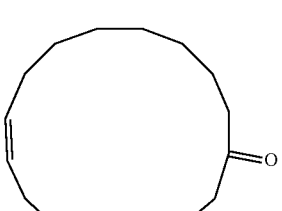 | Polycyclic | −5.29 | Non Active | −5.325 | Non Active |
| Musk MC4 | sweet clean waxy musk animal | 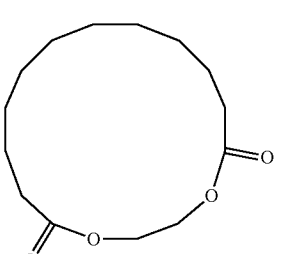 | Polycyclic | −4.42 | Non Active | −4.12 | Non Active |

TABLE 2-continued complete list of musk compounds tested on the OR of the invention, OR5A1, OR5AN1, OR11A1
(Non Active represents negative experiments, no activation after testing)

| Name | Organoletic properties | Structure | Class | OR5A2 | OR5A1 | OR5AN1 | OR11A1 |
| --- | --- | --- | --- | --- | --- | --- | --- |
| Cervolide | musk woody sweet brassylate fruity | 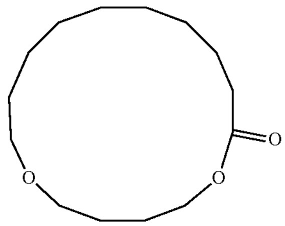 [SMILES: O=C1CCCCCCCCCOCCCCO1] | Polycyclic | −4.52 | Non Active | −4.13 | Non Active |
| ω-6-Hexadecenlactone | sweet soapy musk amber fruity berry | 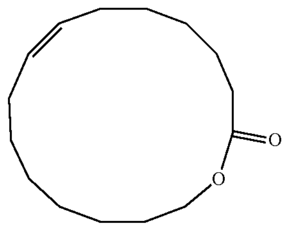 [SMILES: O=C1CCCCC/C=C\CCCCCCCO1] | Polycyclic | −5.17 | Non Active | −4.68 | Non Active |
| nirvanolide | intense musky, fruity, powdery odor with lactonic nuances | 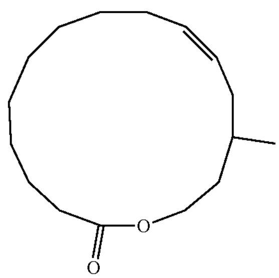 [SMILES: CC1C/C=C\CCCCCCCCC(=O)OCC1] | Polycyclic | −4.71 | Non Active | −3.38 | Non Active |
| Isoambrettolide | sweet musk ambrette fruity waxy | 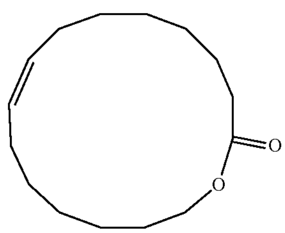 [SMILES: O=C1CCCCCC/C=C\CCCCCCO1] | Polycyclic | −4.72 | Non Active | Non Active | Non Active |
| Habanolide | musk | 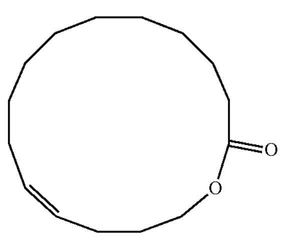 [SMILES: O=C1CCCCCCCCC/C=C\CCCO1] | Polycyclic | −4.79 | Non Active | −4.18 | Non Active |
| Musk 77 | musk-like note | 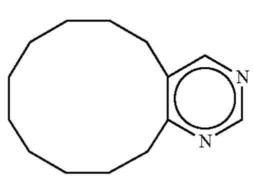 | Polycyclic | −5.29 | Non Active | Non Active | −5.04 |

TABLE 2-continued complete list of musk compounds tested on the OR of the invention, OR5A1, OR5AN1, OR11A1
(Non Active represents negative experiments, no activation after testing)

| Name | Organoletic properties | Structure | Class | OR5A2 | OR5A1 | OR5AN1 | OR11A1 |
| --- | --- | --- | --- | --- | --- | --- | --- |
| Oxalide T | | 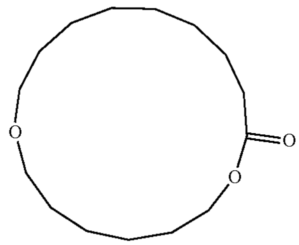 [SMILES: O=C1CCCCCCCCOCCCCCCO1] | Polycyclic | −5.08 | Non Active | −4.49 | Non Active |
| Crysolide | animal musk cedar ambergris woody | 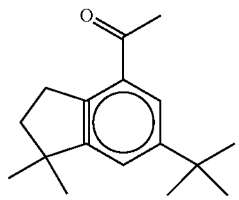 | Polycyclic | −4.65 | Non Active | −3.92 | Non Active |
| Tonalide ® | strong sweet amber fruity musk powdery | 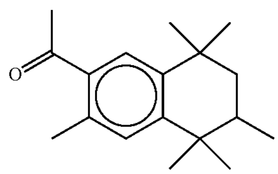 | Polycyclic | −6.12 | Non Active | Non Active | −4.74 |
| Phantolide | strong sweet musk amber powdery dry fruity | 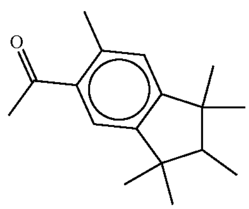 | Polycyclic | −5.34 | Non Active | Non Active | −5.12 |
| Cashmeran | rich spicy musk woody clean | 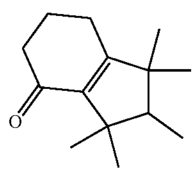 | Polycyclic | −4.75 | Non Active | Non Active | −4.67 |
| Galaxolide® | strong diffusive sweet floral musk | 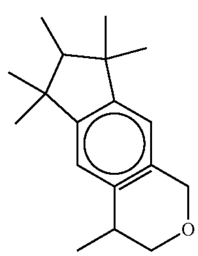 | Polycyclic | −5.98 | Non Active | Non Active | Non Active |
| Traseolide | dry sweet amber musk herbal creamy | 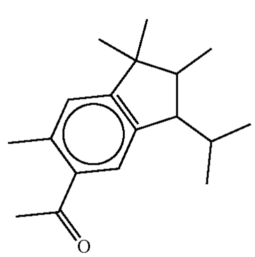 | Polycyclic | −5.71 | Non Active | Non Active | −5.15 |

TABLE 2-continued complete list of musk compounds tested on the OR of the invention, OR5A1, OR5AN1, OR11A1
(Non Active represents negative experiments, no activation after testing)

| Name | Organoletic properties | Structure | Class | OR5A2 | OR5A1 | OR5AN1 | OR11A1 |
|---|---|---|---|---|---|---|---|
| Moxalone | Moxalone ® is a musk fragrance ingredient by Givaudan | 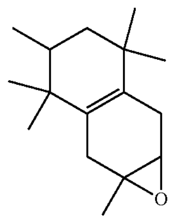 | Polycyclic | −4.53 | Non Active | −3.51 | Non Active |
| Vernolide | sweet intense musk ambrette macrocyclic | 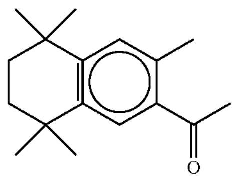 | Polycyclic | −5.17 | Non Active | Non Active | −4.81 |
| Fixal | powerful, very natural-warm, musk-like odor notes | 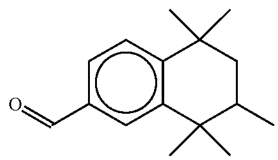 | Polycyclic | −4.99 | Non Active | Non Active | −5.05 |
| Cyclopentenyl propionate musk | sweet musk | 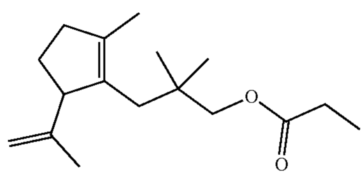 [SMILES: C=C(C)C1CCC(C)=C1CC(C)(C)COC(=O)CC] | Linear | −4.55 | Non Active | Non Active | Non Active |
| serenolide | musk | 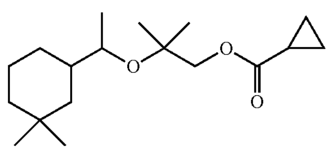 [SMILES: CC(OC(C)(C)COC(=O)C1CC1)C1CCCC(C)(C)C1] | Linear | −4.66 | Non Active | Non Active | Non Active |
| Sylkolide | Sylkolide ™ is a musk by Givaudan | 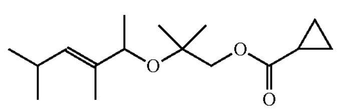 [SMILES: C/C(=C\C(C)C)C(C)OC(C)(C)COC(=O)C1CC1] | Linear | −4.75 | Non Active | Non Active | Non Active |
| Helvetolide | musky, ambrette, pear | 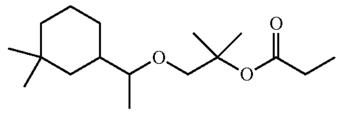 [SMILES: CCC(=O)OC(C)(C)COC(C)C1CCCC(C)(C)C1] | Linear | −3.86 | Non Active | Non Active | Non Active |

SEQ ID No1; OR5A2_variant 1 P172; OR5A2
Nucleotide Sequence
ATGGCTGTAGGAAGGAACAACACAATTGTGACAAAATTCATTCTCCTGGGACTTTCAGACCATCCTCAAA

TGAAGATTTTCCTTTTCATGTTATTTCTGGGGCTCTACCTCCTGACGTTGGCCTGGAACTTAAGCCTCAT

TGCCCTCATTAAGATGGACTCTCACCTGCACATGCCCATGTACTTCTTCCTCAGTAACCTGTCCTTCCTG

GACATCTGCTATGTGTCCTCCACCGCCCCTAAGATGCTGTCTGACATCATCACAGAGCAGAAAACCATTT

CCTTTGTTGGCTGTGCCACTCAGTACTTTGTCTTCTGTGGGATGGGGCTGACTGAATGCTTTCTCCTGGC

AGCTATGGCCTATGACCGGTATGCTGCAATCTGCAACCCCTTGCTTTACACAGTCCTCATATCCCATACA

-continued

```
CTTTGTTTAAAGATGGTGGTTGGCGCCTATGTGGGTGGATTCCTTAGTTCTTTCATTGAAACATACTCTG

TCTATCAGCATGATTTCTGTGGGCCCTATATGATCAACCACTTTTTCTGTGACCTCCCTCCAGTCCTGGC

TCTGTCCTGCTCTGATACCTTCACCAGCGAGGTGGTGACCTTCATAGTCAGTGTTGTCGTTGGAATAGTG

TCTGTGCTAGTGGTCCTCATCTCTTATGGTTACATTGTTGCTGCTGTTGTGAAGATCAGCTCAGCTACAG

GTAGGACAAAGGCCTTCAGCACTTGTGCCTCTCACCTGACTGCTGTGACCCTCTTCTATGGTTCTGGATT

CTTCATGTACATGCGACCCAGTTCCAGCTACTCCCTAAACAGGGACAAGGTGGTGTCCATATTCTATGCC

TTGGTGATCCCCGTGGTGAATCCCATCATCTACAGTTTTAGGAATAAGGAGATTAAAAATGCCATGAGGA

AAGCCATGGAAAGGGACCCCGGGATTTCTCACGGTGGACCATTCATTTTTATGACCTTGGGCTAA
```

SEQ ID No2; OR5A2_variant 1 P172; OR5A2
Translation
MAVGRNNTIVTKFILLGLSDHPQMKIFLFMLFLGLYLLTLAWNLSLIALIKMDSHLHMPMYFFLSNLSFL

DICYVSSTAPKMLSDIITEQKTISFVGCATQYFVFCGMGLTECFLLAAMAYDRYAAICNPLLYTVLISHT

LCLKMVVGAYVGGFLSSFIETYSVYQHDFCGPYMINHFFCDLPPVLALSCSDTFTSEVVTFIVSVVVGIV

SVLVVLISYGYIVAAVVKISSATGRTKAFSTCASHLTAVTLFYGSGFFMYMRPSSSYSLNRDKVVSIFYA

LVIPVVNPIIYSFRNKEIKNAMRKAMERDPGISHGGPFIFMTLG

SEQ ID No3; OR5A2_variant 2 P172L
Nucleotide Sequence
```
ATGGCTGTAGGAAGGAACAACACAATTGTGACAAAATTCATTCTCCTGGGACTTTCAGACCATCCTCAAA

TGAAGATTTTCCTTTTCATGTTATTTCTGGGGCTCTACCTCCTGACGTTGGCCTGGAACTTAAGCCTCAT

TGCCCTCATTAAGATGGACTCTCACCTGCACATGCCCATGTACTTCTTCCTCAGTAACCTGTCCTTCCTG

GACATCTGCTATGTGTCCTCCACCGCCCCTAAGATGCTGTCTGACATCATCACAGAGCAGAAAACCATTT

CCTTTGTTGGCTGTGCCACTCAGTACTTTGTCTTCTGTGGGATGGGGCTGACTGAATGCTTTCTCCTGGC

AGCTATGGCCTATGACCGGTATGCTGCAATCTGCAACCCCTTGCTTTACACAGTCCTCATATCCCATACA

CTTTGTTTAAAGATGGTGGTTGGCGCCTATGTGGGTGGATTCCTTAGTTCTTTCATTGAAACATACTCTG

TCTATCAGCATGATTTCTGTGGGCTCTATATGATCAACCACTTTTTCTGTGACCTCCCTCCAGTCCTGGC

TCTGTCCTGCTCTGATACCTTCACCAGCGAGGTGGTGACCTTCATAGTCAGTGTTGTCGTTGGAATAGTG

TCTGTGCTAGTGGTCCTCATCTCTTATGGTTACATTGTTGCTGCTGTTGTGAAGATCAGCTCAGCTACAG

GTAGGACAAAGGCCTTCAGCACTTGTGCCTCTCACCTGACTGCTGTGACCCTCTTCTATGGTTCTGGATT

CTTCATGTACATGCGACCCAGTTCCAGCTACTCCCTAAACAGGGACAAGGTGGTGTCCATATTCTATGCC

TTGGTGATCCCCGTGGTGAATCCCATCATCTACAGTTTTAGGAATAAGGAGATTAAAAATGCCATGAGGA

AAGCCATGGAAAGGGACCCCGGGATTTCTCACGGTGGACCATTCATTTTTATGACCTTGGGCTAA
```

SEQ ID No4; OR5A2_variant 2 P172L
Translation
MAVGRNNTIVTKFILLGLSDHPQMKIFLFMLFLGLYLLTLAWNLSLIALIKMDSHLHMPMYFFLSNLSFL

DICYVSSTAPKMLSDIITEQKTISFVGCATQYFVFCGMGLTECFLLAAMAYDRYAAICNPLLYTVLISHT

LCLKMVVGAYVGGFLSSFIETYSVYQHDFCGLYMINHFFCDLPPVLALSCSDTFTSEVVTFIVSVVVGIV

SVLVVLISYGYIVAAVVKISSATGRTKAFSTCASHLTAVTLFYGSGFFMYMRPSSSYSLNRDKVVSIFYA

LVIPVVNPIIYSFRNKEIKNAMRKAMERDPGISHGGPFIFMTLG

SEQ ID No5
Ac-FKKSFKL-NH2

SEQ ID No6
RRLIEDAEYAARG

SEQ ID No7; OR5AN1
MTGGGNITEITYFILLGFSDFPRIIKVLFTIFLVIYITSLAWNLSLIVLIRMDSHLHTPMYFFLSNLSFIDVCYI

SSTVPKMLSNLLQGQQTITFVGCIIQYFIFSTMGLSESCLMTAMAYDRYAAICNPLLYSSIMSPTLCVWMVLGAY

MTGLTASLFQIGALLQLHFCGSNVIRHFFCDMPQLLILSCTDTFFVQVMTAILTMFFGIASALVIMISYGYIGIS

IMKITSAKGRSKAFNTCASHLTAVSLFYTSGIFVYLSSSGGSSSFDRFASVFYTVVIPMLNPLIYSLRNKEIKD

ALKRLQKRKCC

SEQ ID No8; OR11A1
MEIVSTGNETITEFVLLGFYDIPELHFLFFIVFTAVYVFIIIGNMLIIVAVVSSQRLHKPMYIFLANLSFLDILY

TSAVMPKMLEGFLQEATISVAGCLLQFFIFGSLATAECLLLAVMAYDRYLAICYPLHYPLLMGPRRYMGLVVTTW

LSGFVVDGLVVALVAQLRFCGPNHIDQFYCDFMLFVGLACSDPRVAQVTTLILSVFCLTIPFGLILTSYARIVVA

VLRVPAGASRRRAFSTCSSHLAVVTTFYGTLMIFYVAPSAVHSQLLSKVFSLLYTVVTPLFNPVIYTMRNKEVHQ

ALRKILCIKQTETLD

SEQ ID No9; OR5A1
MSITKAWNSSSVTMFILLGFTDHPELQALLFVTFLGIYLTTLAWNLALIFLIRGDTHLHTPMYFFLSNLSFIDIC

YSSAVAPNMLTDFFWEQKTISFVGCAAQFFFFVGMGLSECLLLTAMAYDRYAAISSPLLYPTIMTQGLCTRMVVG

AYVGGFLSSLIQASSIFRLHFCGPNIIINHFFCDLPPVLALSCSDTFLSQVVNFLVVVTVGGTSFLQLLISYGYIV

SAVLKIPSAEGRWKACNTCASHLMVVTLLFGTALFVYLRPSSSYLLGRDKVVSVFYSLVIPMLNPLIYSLRNKEI

KDALWKVLERKKVFS

SEQ ID No10; chimeric OR5A2_variant 1
MTKNQTWVTEFILLGFPLSLRIQMLLSGLFSLLYVFTLLGNGAILGLIWLDSRLHTPMYFFLSNLSFLDICYVSS

TAPKMLSDIITEQKTISFVGCATQYFVFCGMGLTECFLLAAMAYDRYAAICNPLLYTVLISHTLCLKMVVGAYVG

GFLSSFIETYSVYQHDFCGPYMINHFFCDLPPVLALSCSDTFTSEVVTFIVSVVVGIVSVLVVLISYGYIVAAVV

KISSATGRTKAFSTCASHLTAVTLFYGSGFFMYMRPSSSYSLNRDKVVSIFYALVIPVVNPLIYSLRNAEVKGAL

KRVLWKQRSK

SEQ ID NOo11; TM2-TM7 region of OR5A2
PMYFFLSNLSFLDICYVSSTAPKMLSDIITEQKTISFVGCATQYFVFCGMGLTECFLLAAMAYDRYAAICNPLLY

TVLISHTLCLKMVVGAYVGGFLSSFIETYSVYQHDFCGPYMINHFFCDLPPVLALSCSDTFTSEVVTFIVSVVVG

IVSVLVVLISYGYIVAAVVKISSATGRTKAFSTCASHLTAVTLFYGSGFFMYMRPSSSYSLNRDKVVSIFYALVI

PVV

SEQ ID NOo12; OR2A5
MTKNQTWVTEFILLGFPLSLRIQMLLSGLFSLLYVFTLLGNGAILGLIWLDSRLHTPMYFFLSHLAIIDISYASN

NVPKMLTNLGLNKRKTISFVPCTMQTFLYMAFAHTECLILVMMSYDRYMAVCHPLQYSVIMRWGVCTVLAVTSWA

CGSLLALVHVVLILRLPFCGPHEINHFFCEILSVLKLACADTWLNQVVIFASSVFILVGPLCLVLVSYSRILAAI

LRIQSGEGRRKAFSTCSSHLCMVGLFFGSTIVMYMAPKSRHPEEQQKVLSLFYSLFNPMLNPLIYSLRNAEVKGA

LKRVLWKQRSK

---

SEQUENCE LISTING

<160> NUMBER OF SEQ ID NOS: 12

<210> SEQ ID NO 1
<211> LENGTH: 975
<212> TYPE: DNA
<213> ORGANISM: Homo sapiens

<400> SEQUENCE: 1
atggctgtag gaaggaacaa cacaattgtg acaaaattca ttctcctggg actttcagac     60
catcctcaaa tgaagatttt cctttcatg ttatttctgg ggtctctacct cctgacgttg    120 gcctggaact taagcctcat tgccctcatt aagatggact ctcacctgca catgcccatg    180

-continued

```
tacttcttcc tcagtaacct gtccttcctg gacatctgct atgtgtcctc caccgcccct      240
aagatgctgt ctgacatcat cacagagcag aaaaccattt cctttgttgg ctgtgccact      300
cagtactttg tcttctgtgg gatggggctg actgaatgct ttctcctggc agctatggcc      360
tatgaccggt atgctgcaat ctgcaacccc ttgctttaca cagtcctcat atcccataca      420
ctttgtttaa agatggtggt tggcgcctat gtgggtggat tccttagttc tttcattgaa      480
acatactctg tctatcagca tgatttctgt gggccctata tgatcaacca cttttttctgt     540 gacctccctc cagtcctggc tctgtcctgc tctgataccot caccagcga ggtggtgacc      600 ttcatagtca gtgttgtcgt tggaatagtg tctgtgctag tggtcctcat ctcttatggt      660
tacattgttg ctgctgttgt gaagatcagc tcagctacag gtaggacaaa ggccttcagc      720
acttgtgcct ctcacctgac tgctgtgacc ctcttctatg gttctggatt cttcatgtac      780
atgcgaccca gttccagcta ctccctaaac agggacaagg tggtgtccat attctatgcc      840
ttggtgatcc ccgtggtgaa tcccatcatc tacagtttta ggaataagga gattaaaaat      900
gccatgagga aagccatgga aagggacccc gggatttctc acggtggacc attcatttt       960 atgaccttgg gctaa                                                       975
```

<210> SEQ ID NO 2
<211> LENGTH: 324
<212> TYPE: PRT
<213> ORGANISM: Homo sapiens

<400> SEQUENCE: 2

```
Met Ala Val Gly Arg Asn Asn Thr Ile Val Thr Lys Phe Ile Leu Leu
 1               5                  10                  15

Gly Leu Ser Asp His Pro Gln Met Lys Ile Phe Leu Phe Met Leu Phe
            20                  25                  30

Leu Gly Leu Tyr Leu Leu Thr Leu Ala Trp Asn Leu Ser Leu Ile Ala
        35                  40                  45

Leu Ile Lys Met Asp Ser His Leu His Met Pro Met Tyr Phe Phe Leu
    50                  55                  60

Ser Asn Leu Ser Phe Leu Asp Ile Cys Tyr Val Ser Ser Thr Ala Pro
65                  70                  75                  80

Lys Met Leu Ser Asp Ile Ile Thr Glu Gln Lys Thr Ile Ser Phe Val
                85                  90                  95

Gly Cys Ala Thr Gln Tyr Phe Val Phe Cys Gly Met Gly Leu Thr Glu
            100                 105                 110

Cys Phe Leu Leu Ala Ala Met Ala Tyr Asp Arg Tyr Ala Ala Ile Cys
        115                 120                 125

Asn Pro Leu Leu Tyr Thr Val Leu Ile Ser His Thr Leu Cys Leu Lys
    130                 135                 140

Met Val Val Gly Ala Tyr Val Gly Gly Phe Leu Ser Ser Phe Ile Glu
145                 150                 155                 160

Thr Tyr Ser Val Tyr Gln His Asp Phe Cys Gly Pro Tyr Met Ile Asn
                165                 170                 175

His Phe Phe Cys Asp Leu Pro Pro Val Leu Ala Leu Ser Cys Ser Asp
            180                 185                 190

Thr Phe Thr Ser Glu Val Val Thr Phe Ile Val Ser Val Val Gly
        195                 200                 205

Ile Val Ser Val Leu Val Val Leu Ile Ser Tyr Gly Tyr Ile Val Ala
    210                 215                 220

Ala Val Val Lys Ile Ser Ser Ala Thr Gly Arg Thr Lys Ala Phe Ser
```

```
                225                 230                 235                 240

Thr Cys Ala Ser His Leu Thr Ala Val Thr Leu Phe Tyr Gly Ser Gly
                        245                 250                 255

Phe Phe Met Tyr Met Arg Pro Ser Ser Tyr Ser Leu Asn Arg Asp
                        260                 265                 270

Lys Val Val Ser Ile Phe Tyr Ala Leu Val Ile Pro Val Asn Pro
                        275                 280                 285

Ile Ile Tyr Ser Phe Arg Asn Lys Glu Ile Lys Asn Ala Met Arg Lys
                        290                 295                 300

Ala Met Glu Arg Asp Pro Gly Ile Ser His Gly Gly Pro Phe Ile Phe
        305                 310                 315                 320

Met Thr Leu Gly

<210> SEQ ID NO 3
        <211> LENGTH: 975
        <212> TYPE: DNA
        <213> ORGANISM: Homo sapiens

<400> SEQUENCE: 3
atggctgtag gaaggaacaa cacaattgtg acaaaattca ttctcctggg actttcagac      60
        catcctcaaa tgaagatttt ccttttcatg ttatttctgg ggctctacct cctgacgttg     120
        gcctggaact taagcctcat tgccctcatt aagatggact ctcacctgca catgcccatg     180
        tacttcttcc tcagtaacct gtccttcctg acatctgct atgtgtcctc caccgcccct     240
        aagatgctgt ctgacatcat cacagagcag aaaaccattt cctttgttgg ctgtgccact     300
        cagtactttg tcttctgtgg gatggggctg actgaatgct ttctcctggc agctatggcc     360
        tatgaccggt atgctgcaat ctgcaacccc ttgctttaca cagtcctcat atcccataca     420
        ctttgtttaa agatggtggt tggcgcctat gtgggtggat ccttagttc tttcattgaa      480
        acatactctg tctatcagca tgatttctgt gggctctata tgatcaacca cttttttctgt     540
        gacctccctc cagtcctggc tctgtcctgc tctgatacct tcaccagcga ggtggtgacc     600
        ttcatagtca gtgttgtcgt tggaatagtg tctgtgctag tggtcctcat ctcttatggt     660
        tacattgttg ctgctgttgt gaagatcagc tcagctacag gtaggacaaa ggccttcagc     720
        acttgtgcct ctcacctgac tgctgtgacc ctcttctatg gttctggatt cttcatgtac     780
        atgcgaccca gttccagcta ctccctaaac agggacaagg tggtgtccat attctatgcc     840
        ttggtgatcc ccgtggtgaa tcccatcatc tacagtttta ggaataagga gattaaaaat     900
        gccatgagga agccatgga aagggacccc gggattctc acggtggacc attcattttt     960
        atgaccttgg gctaa                                                     975

<210> SEQ ID NO 4
        <211> LENGTH: 324
        <212> TYPE: PRT
        <213> ORGANISM: Homo sapiens

<400> SEQUENCE: 4

Met Ala Val Gly Arg Asn Asn Thr Ile Val Thr Lys Phe Ile Leu Leu
        1               5                   10                  15

Gly Leu Ser Asp His Pro Gln Met Lys Ile Phe Leu Phe Met Leu Phe
                        20                  25                  30

Leu Gly Leu Tyr Leu Leu Thr Leu Ala Trp Asn Leu Ser Leu Ile Ala
                        35                  40                  45

Leu Ile Lys Met Asp Ser His Leu His Met Pro Met Tyr Phe Phe Leu
```

-continued

```
                50                  55                  60
Ser Asn Leu Ser Phe Leu Asp Ile Cys Tyr Val Ser Ser Thr Ala Pro
 65                  70                  75                  80

Lys Met Leu Ser Asp Ile Ile Thr Glu Gln Lys Thr Ile Ser Phe Val
                 85                  90                  95

Gly Cys Ala Thr Gln Tyr Phe Val Phe Cys Gly Met Gly Leu Thr Glu
                100                 105                 110

Cys Phe Leu Leu Ala Ala Met Ala Tyr Asp Arg Tyr Ala Ala Ile Cys
                115                 120                 125

Asn Pro Leu Leu Tyr Thr Val Leu Ile Ser His Thr Leu Cys Leu Lys
130                 135                 140

Met Val Val Gly Ala Tyr Val Gly Gly Phe Leu Ser Ser Phe Ile Glu
145                 150                 155                 160

Thr Tyr Ser Val Tyr Gln His Asp Phe Cys Gly Leu Tyr Met Ile Asn
                165                 170                 175

His Phe Phe Cys Asp Leu Pro Pro Val Leu Ala Leu Ser Cys Ser Asp
                180                 185                 190

Thr Phe Thr Ser Glu Val Val Thr Phe Ile Val Ser Val Val Val Gly
                195                 200                 205

Ile Val Ser Val Leu Val Leu Ile Ser Tyr Gly Tyr Ile Val Ala
                210                 215                 220

Ala Val Val Lys Ile Ser Ser Ala Thr Gly Arg Thr Lys Ala Phe Ser
225                 230                 235                 240

Thr Cys Ala Ser His Leu Thr Ala Val Thr Leu Phe Tyr Gly Ser Gly
                245                 250                 255

Phe Phe Met Tyr Met Arg Pro Ser Ser Tyr Ser Leu Asn Arg Asp
                260                 265                 270

Lys Val Val Ser Ile Phe Tyr Ala Leu Val Ile Pro Val Asn Pro
                275                 280                 285

Ile Ile Tyr Ser Phe Arg Asn Lys Glu Ile Lys Asn Ala Met Arg Lys
                290                 295                 300

Ala Met Glu Arg Asp Pro Gly Ile Ser His Gly Gly Pro Phe Ile Phe
305                 310                 315                 320

Met Thr Leu Gly
```

<210> SEQ ID NO 5
<211> LENGTH: 7
<212> TYPE: PRT
<213> ORGANISM: artificial sequence
<220> FEATURE:
<223> OTHER INFORMATION: MARCKS peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: AMIDATION

<400> SEQUENCE: 5

```
Phe Lys Lys Ser Phe Lys Leu
 1               5
```

<210> SEQ ID NO 6
<211> LENGTH: 13
<212> TYPE: PRT
<213> ORGANISM: Artificial seqence
<220> FEATURE:

<223> OTHER INFORMATION: Src-related peptide

<400> SEQUENCE: 6

```
Arg Arg Leu Ile Glu Asp Ala Glu Tyr Ala Ala Arg Gly
1               5                   10
```

<210> SEQ ID NO 7
<211> LENGTH: 311
<212> TYPE: PRT
<213> ORGANISM: Homo sapiens

<400> SEQUENCE: 7

```
Met Thr Gly Gly Gly Asn Ile Thr Glu Ile Thr Tyr Phe Ile Leu Leu
1               5                   10                  15

Gly Phe Ser Asp Phe Pro Arg Ile Ile Lys Val Leu Phe Thr Ile Phe
                20                  25                  30

Leu Val Ile Tyr Ile Thr Ser Leu Ala Trp Asn Leu Ser Leu Ile Val
            35                  40                  45

Leu Ile Arg Met Asp Ser His Leu His Thr Pro Met Tyr Phe Phe Leu
        50                  55                  60

Ser Asn Leu Ser Phe Ile Asp Val Cys Tyr Ile Ser Ser Thr Val Pro
65                  70                  75                  80

Lys Met Leu Ser Asn Leu Leu Gln Gly Gln Gln Thr Ile Thr Phe Val
                85                  90                  95

Gly Cys Ile Ile Gln Tyr Phe Ile Phe Ser Thr Met Gly Leu Ser Glu
            100                 105                 110

Ser Cys Leu Met Thr Ala Met Ala Tyr Asp Arg Tyr Ala Ala Ile Cys
        115                 120                 125

Asn Pro Leu Leu Tyr Ser Ser Ile Met Ser Pro Thr Leu Cys Val Trp
    130                 135                 140

Met Val Leu Gly Ala Tyr Met Thr Gly Leu Thr Ala Ser Leu Phe Gln
145                 150                 155                 160

Ile Gly Ala Leu Leu Gln Leu His Phe Cys Gly Ser Asn Val Ile Arg
                165                 170                 175

His Phe Phe Cys Asp Met Pro Gln Leu Leu Ile Leu Ser Cys Thr Asp
            180                 185                 190

Thr Phe Phe Val Gln Val Met Thr Ala Ile Leu Thr Met Phe Phe Gly
        195                 200                 205

Ile Ala Ser Ala Leu Val Ile Met Ile Ser Tyr Gly Tyr Ile Gly Ile
    210                 215                 220

Ser Ile Met Lys Ile Thr Ser Ala Lys Gly Arg Ser Lys Ala Phe Asn
225                 230                 235                 240

Thr Cys Ala Ser His Leu Thr Ala Val Ser Leu Phe Tyr Thr Ser Gly
                245                 250                 255

Ile Phe Val Tyr Leu Ser Ser Ser Gly Gly Ser Ser Ser Phe Asp
            260                 265                 270

Arg Phe Ala Ser Val Phe Tyr Thr Val Val Ile Pro Met Leu Asn Pro
        275                 280                 285

Leu Ile Tyr Ser Leu Arg Asn Lys Glu Ile Lys Asp Ala Leu Lys Arg
    290                 295                 300

Leu Gln Lys Arg Lys Cys Cys
305                 310
```

<210> SEQ ID NO 8
<211> LENGTH: 315
<212> TYPE: PRT

<213> ORGANISM: Homo sapiens

<400> SEQUENCE: 8

```
Met Glu Ile Val Ser Thr Gly Asn Glu Thr Ile Glu Phe Val Leu
1               5                   10                  15

Leu Gly Phe Tyr Asp Ile Pro Glu Leu His Phe Leu Phe Phe Ile Val
            20                  25                  30

Phe Thr Ala Val Tyr Val Phe Ile Ile Gly Asn Met Leu Ile Ile
        35                  40                  45

Val Ala Val Ser Ser Gln Arg Leu His Lys Pro Met Tyr Ile Phe
    50                  55                  60

Leu Ala Asn Leu Ser Phe Leu Asp Ile Leu Tyr Thr Ser Ala Val Met
65                  70                  75                  80

Pro Lys Met Leu Glu Gly Phe Leu Gln Glu Ala Thr Ile Ser Val Ala
                85                  90                  95

Gly Cys Leu Leu Gln Phe Phe Ile Phe Gly Ser Leu Ala Thr Ala Glu
            100                 105                 110

Cys Leu Leu Leu Ala Val Met Ala Tyr Asp Arg Tyr Leu Ala Ile Cys
        115                 120                 125

Tyr Pro Leu His Tyr Pro Leu Leu Met Gly Pro Arg Arg Tyr Met Gly
    130                 135                 140

Leu Val Val Thr Thr Trp Leu Ser Gly Phe Val Val Asp Gly Leu Val
145                 150                 155                 160

Val Ala Leu Val Ala Gln Leu Arg Phe Cys Gly Pro Asn His Ile Asp
                165                 170                 175

Gln Phe Tyr Cys Asp Phe Met Leu Phe Val Gly Leu Ala Cys Ser Asp
            180                 185                 190

Pro Arg Val Ala Gln Val Thr Thr Leu Ile Leu Ser Val Phe Cys Leu
        195                 200                 205

Thr Ile Pro Phe Gly Leu Ile Leu Thr Ser Tyr Ala Arg Ile Val Val
    210                 215                 220

Ala Val Leu Arg Val Pro Ala Gly Ala Ser Arg Arg Arg Ala Phe Ser
225                 230                 235                 240

Thr Cys Ser Ser His Leu Ala Val Val Thr Thr Phe Tyr Gly Thr Leu
                245                 250                 255

Met Ile Phe Tyr Val Ala Pro Ser Ala Val His Ser Gln Leu Leu Ser
            260                 265                 270

Lys Val Phe Ser Leu Leu Tyr Thr Val Val Thr Pro Leu Phe Asn Pro
        275                 280                 285

Val Ile Tyr Thr Met Arg Asn Lys Glu Val His Gln Ala Leu Arg Lys
    290                 295                 300

Ile Leu Cys Ile Lys Gln Thr Glu Thr Leu Asp
305                 310                 315
```

<210> SEQ ID NO 9
<211> LENGTH: 315
<212> TYPE: PRT
<213> ORGANISM: Homo sapiens

<400> SEQUENCE: 9

```
Met Ser Ile Thr Lys Ala Trp Asn Ser Ser Ser Val Thr Met Phe Ile
1               5                   10                  15

Leu Leu Gly Phe Thr Asp His Pro Glu Leu Gln Ala Leu Leu Phe Val
            20                  25                  30

Thr Phe Leu Gly Ile Tyr Leu Thr Thr Leu Ala Trp Asn Leu Ala Leu
```

```
                35                  40                  45
Ile Phe Leu Ile Arg Gly Asp Thr His Leu His Thr Pro Met Tyr Phe
 50                  55                  60

Phe Leu Ser Asn Leu Ser Phe Ile Asp Ile Cys Tyr Ser Ser Ala Val
 65                  70                  75                  80

Ala Pro Asn Met Leu Thr Asp Phe Phe Trp Glu Gln Lys Thr Ile Ser
                 85                  90                  95

Phe Val Gly Cys Ala Ala Gln Phe Phe Phe Val Gly Met Gly Leu
                100                 105                 110

Ser Glu Cys Leu Leu Leu Thr Ala Met Ala Tyr Asp Arg Tyr Ala Ala
                115                 120                 125

Ile Ser Ser Pro Leu Leu Tyr Pro Thr Ile Met Thr Gln Gly Leu Cys
            130                 135                 140

Thr Arg Met Val Val Gly Ala Tyr Val Gly Gly Phe Leu Ser Ser Leu
145                 150                 155                 160

Ile Gln Ala Ser Ser Ile Phe Arg Leu His Phe Cys Gly Pro Asn Ile
                165                 170                 175

Ile Asn His Phe Phe Cys Asp Leu Pro Pro Val Leu Ala Leu Ser Cys
            180                 185                 190

Ser Asp Thr Phe Leu Ser Gln Val Val Asn Phe Leu Val Val Val Thr
            195                 200                 205

Val Gly Gly Thr Ser Phe Leu Gln Leu Leu Ile Ser Tyr Gly Tyr Ile
210                 215                 220

Val Ser Ala Val Leu Lys Ile Pro Ser Ala Glu Gly Arg Trp Lys Ala
225                 230                 235                 240

Cys Asn Thr Cys Ala Ser His Leu Met Val Val Thr Leu Leu Phe Gly
                245                 250                 255

Thr Ala Leu Phe Val Tyr Leu Arg Pro Ser Ser Ser Tyr Leu Leu Gly
                260                 265                 270

Arg Asp Lys Val Val Ser Val Phe Tyr Ser Leu Val Ile Pro Met Leu
            275                 280                 285

Asn Pro Leu Ile Tyr Ser Leu Arg Asn Lys Glu Ile Lys Asp Ala Leu
        290                 295                 300

Trp Lys Val Leu Glu Arg Lys Lys Val Phe Ser
305                 310                 315

<210> SEQ ID NO 10
<211> LENGTH: 310
<212> TYPE: PRT
<213> ORGANISM: Artificial sequence
<220> FEATURE:
<223> OTHER INFORMATION: chimeric receptor OR5A2_variant 1

<400> SEQUENCE: 10

Met Thr Lys Asn Gln Thr Trp Val Thr Glu Phe Ile Leu Leu Gly Phe
 1                   5                  10                  15

Pro Leu Ser Leu Arg Ile Gln Met Leu Leu Ser Gly Leu Phe Ser Leu
                20                  25                  30

Leu Tyr Val Phe Thr Leu Leu Gly Asn Gly Ala Ile Leu Gly Leu Ile
            35                  40                  45

Trp Leu Asp Ser Arg Leu His Thr Pro Met Tyr Phe Phe Leu Ser Asn
 50                  55                  60

Leu Ser Phe Leu Asp Ile Cys Tyr Val Ser Ser Thr Ala Pro Lys Met
 65                  70                  75                  80

Leu Ser Asp Ile Ile Thr Glu Gln Lys Thr Ile Ser Phe Val Gly Cys
```

```
                        85                  90                  95
Ala Thr Gln Tyr Phe Val Phe Cys Gly Met Gly Leu Thr Glu Cys Phe
                100                 105                 110

Leu Leu Ala Ala Met Ala Tyr Asp Arg Tyr Ala Ala Ile Cys Asn Pro
                115                 120                 125

Leu Leu Tyr Thr Val Leu Ile Ser His Thr Leu Cys Leu Lys Met Val
            130                 135                 140

Val Gly Ala Tyr Val Gly Gly Phe Leu Ser Ser Phe Ile Glu Thr Tyr
145                 150                 155                 160

Ser Val Tyr Gln His Asp Phe Cys Gly Pro Tyr Met Ile Asn His Phe
                165                 170                 175

Phe Cys Asp Leu Pro Pro Val Leu Ala Leu Ser Cys Ser Asp Thr Phe
                180                 185                 190

Thr Ser Glu Val Val Thr Phe Ile Val Ser Val Val Gly Ile Val
            195                 200                 205

Ser Val Leu Val Val Leu Ile Ser Tyr Gly Tyr Ile Val Ala Ala Val
            210                 215                 220

Val Lys Ile Ser Ser Ala Thr Gly Arg Thr Lys Ala Phe Ser Thr Cys
225                 230                 235                 240

Ala Ser His Leu Thr Ala Val Thr Leu Phe Tyr Gly Ser Gly Phe Phe
                245                 250                 255

Met Tyr Met Arg Pro Ser Ser Tyr Ser Leu Asn Arg Asp Lys Val
                260                 265                 270

Val Ser Ile Phe Tyr Ala Leu Val Ile Pro Val Val Asn Pro Leu Ile
            275                 280                 285

Tyr Ser Leu Arg Asn Ala Glu Val Lys Gly Ala Leu Lys Arg Val Leu
            290                 295                 300

Trp Lys Gln Arg Ser Lys
305                 310

<210> SEQ ID NO 11
<211> LENGTH: 228
<212> TYPE: PRT
<213> ORGANISM: Homo sapiens

<400> SEQUENCE: 11

Pro Met Tyr Phe Phe Leu Ser Asn Leu Ser Phe Leu Asp Ile Cys Tyr
1               5                   10                  15

Val Ser Ser Thr Ala Pro Lys Met Leu Ser Asp Ile Ile Thr Glu Gln
                20                  25                  30

Lys Thr Ile Ser Phe Val Gly Cys Ala Thr Gln Tyr Phe Val Phe Cys
            35                  40                  45

Gly Met Gly Leu Thr Glu Cys Phe Leu Leu Ala Ala Met Ala Tyr Asp
50                  55                  60

Arg Tyr Ala Ala Ile Cys Asn Pro Leu Leu Tyr Thr Val Leu Ile Ser
65                  70                  75                  80

His Thr Leu Cys Leu Lys Met Val Val Gly Ala Tyr Val Gly Gly Phe
                85                  90                  95

Leu Ser Ser Phe Ile Glu Thr Tyr Ser Val Tyr Gln His Asp Phe Cys
                100                 105                 110

Gly Pro Tyr Met Ile Asn His Phe Cys Asp Leu Pro Val Leu
            115                 120                 125

Ala Leu Ser Cys Ser Asp Thr Phe Thr Ser Glu Val Val Thr Phe Ile
            130                 135                 140
```

```
Val Ser Val Val Val Gly Ile Val Ser Val Leu Val Leu Ile Ser
145                 150                 155                 160

Tyr Gly Tyr Ile Val Ala Ala Val Val Lys Ile Ser Ser Ala Thr Gly
                165                 170                 175

Arg Thr Lys Ala Phe Ser Thr Cys Ala Ser His Leu Thr Ala Val Thr
            180                 185                 190

Leu Phe Tyr Gly Ser Gly Phe Phe Met Tyr Met Arg Pro Ser Ser Ser
        195                 200                 205

Tyr Ser Leu Asn Arg Asp Lys Val Val Ser Ile Phe Tyr Ala Leu Val
    210                 215                 220

Ile Pro Val Val
225
```

<210> SEQ ID NO 12
<211> LENGTH: 311
<212> TYPE: PRT
<213> ORGANISM: Homo sapiens

<400> SEQUENCE: 12

```
Met Thr Lys Asn Gln Thr Trp Val Thr Glu Phe Ile Leu Leu Gly Phe
1               5                   10                  15

Pro Leu Ser Leu Arg Ile Gln Met Leu Leu Ser Gly Leu Phe Ser Leu
                20                  25                  30

Leu Tyr Val Phe Thr Leu Leu Gly Asn Gly Ala Ile Leu Gly Leu Ile
            35                  40                  45

Trp Leu Asp Ser Arg Leu His Thr Pro Met Tyr Phe Phe Leu Ser His
        50                  55                  60

Leu Ala Ile Ile Asp Ile Ser Tyr Ala Ser Asn Asn Val Pro Lys Met
65                  70                  75                  80

Leu Thr Asn Leu Gly Leu Asn Lys Arg Lys Thr Ile Ser Phe Val Pro
                85                  90                  95

Cys Thr Met Gln Thr Phe Leu Tyr Met Ala Phe Ala His Thr Glu Cys
            100                 105                 110

Leu Ile Leu Val Met Met Ser Tyr Asp Arg Tyr Met Ala Val Cys His
        115                 120                 125

Pro Leu Gln Tyr Ser Val Ile Met Arg Trp Gly Val Cys Thr Val Leu
    130                 135                 140

Ala Val Thr Ser Trp Ala Cys Gly Ser Leu Leu Ala Leu Val His Val
145                 150                 155                 160

Val Leu Ile Leu Arg Leu Pro Phe Cys Gly Pro His Glu Ile Asn His
                165                 170                 175

Phe Phe Cys Glu Ile Leu Ser Val Leu Lys Leu Ala Cys Ala Asp Thr
            180                 185                 190

Trp Leu Asn Gln Val Val Ile Phe Ala Ser Ser Val Phe Ile Leu Val
        195                 200                 205

Gly Pro Leu Cys Leu Val Leu Val Ser Tyr Ser Arg Ile Leu Ala Ala
    210                 215                 220

Ile Leu Arg Ile Gln Ser Gly Glu Gly Arg Arg Lys Ala Phe Ser Thr
225                 230                 235                 240

Cys Ser Ser His Leu Cys Met Val Gly Leu Phe Phe Gly Ser Thr Ile
                245                 250                 255

Val Met Tyr Met Ala Pro Lys Ser Arg His Pro Glu Glu Gln Gln Lys
            260                 265                 270

Val Leu Ser Leu Phe Tyr Ser Leu Phe Asn Pro Met Leu Asn Pro Leu
        275                 280                 285
```

```
Ile Tyr Ser Leu Arg Asn Ala Glu Val Lys Gly Ala Leu Lys Arg Val
    290                 295                 300

Leu Trp Lys Gln Arg Ser Lys
305                 310
```

What is claimed is:

1. A method for identifying an agent or a sample comprising one or more agent(s) that interfere with the binding between an OR5A2 receptor and musk compounds, said method comprising:
   a) contacting a chimeric receptor with said agent or sample, wherein said chimeric receptor comprises a central region of the OR5A2 receptor, encompassing the transmembrane domains 2 to 7 having the amino acid sequence of SEQ ID NO: 11, or a polypeptide sequence having at least 95% sequence identity to SEQ ID NO: 11, with the proviso that said polypeptide has a proline at position 114 of said polypeptide sequence having at least 95% sequence identity to SEQ ID NO: 11 and,
   wherein the central region is fused at its N-terminus to the N-terminal extracellular moiety, the transmembrane domain 1 and the intracellular loop 1 of a G protein-coupled receptor, and which is fused at its C-terminus to the intracellular C-terminal end of a G protein-coupled receptor,
   wherein the chimeric receptor is capable of binding musk compounds selected from the group consisting of: nitromusks, macrocyclic musks, polycyclic musks, and linear musks;
   b) measuring a signaling activity of the chimeric receptor in the presence of said agent or sample; and
   c) comparing the activity measured in the presence of said agent or sample to the activity measured in a reaction in which the chimeric receptor is contacted with one or more musk compound(s) at its/their $EC_{50}$, wherein said agent or sample is identified as an agent or a sample, that modulates the activity of said chimeric receptor as defined herein when the amount of the activity measured in the presence of the agent or sample is at least 10% of the amount induced by said musk compound(s) at its/their $EC_{50}$.

2. The method according to claim 1, said method comprising:
   a) contacting a chimeric receptor that comprises the central region of OR5A2, encompassing the transmembrane domains 2 to 7 having the amino acid sequence of SEQ ID NO: 11, which is fused at its N-terminus to the N-terminal extracellular moiety, the transmembrane domain 1 and the intracellular loop 1 of a G protein-coupled receptor; and which is fused at its C-terminus to the intracellular C-terminal end of a G protein-coupled receptor, for identifying agents or samples that interfere with the binding between said OR5A2 chimeric receptor and musk compounds, with said agent or sample, wherein said chimeric receptor is capable of binding musk compounds selected from the group consisting of: nitromusks, macrocyclic musks, polycyclic musks and linear musks;
   b) measuring a signaling activity of said chimeric receptor in the presence of said agent or sample; and
   c) comparing the activity measured in the presence of said agent or sample to the activity measured in a reaction in which said chimeric receptor is contacted with one or more musk compound(s) at its/their $EC_{50}$, wherein said agent or sample is identified as an agent or a sample, that modulates the activity of said chimeric receptor as defined herein when the amount of the activity measured in the presence of the agent or sample is at least 10% of the amount induced by said musk compound(s) at its/their $EC_{50}$.

3. The method according to claim 1, wherein said G protein-coupled receptor is an olfactory receptor.

4. The method according to claim 1, wherein said G protein-coupled receptor is an OR2A5 receptor having the amino acid sequence of SEQ ID NO: 12, thereby resulting in a chimeric receptor as having the amino acid sequence of SEQ ID NO: 10.

5. The method according to claim 1, wherein said chimeric receptor has the amino acid sequence of SEQ ID NO: 2.

6. The method according to claim 1, wherein said chimeric receptor has a polypeptide sequence having at least 95% sequence identity to SEQ ID NO: 2, with the proviso that said polypeptide has a proline at position 172 of said polypeptide sequence having at least 95% sequence identity to SEQ ID NO: 2, wherein said chimeric receptor is capable of binding musk compounds selected from the group consisting of: nitromusks, macrocyclic musks, polycyclic musks and linear musks.

7. The method according to claim 1, wherein an increase in the activity in the presence of said agent or sample relative to the activity in the absence of said agent or sample identifies said agent or sample as an agent or sample that increases the activity of the chimeric receptor.

8. The method according to claim 1, wherein a decrease in the activity in the presence of said agent or sample relative to the activity in the absence of said agent or sample identifies said agent or sample as an agent or a sample that decreases the activity of the chimeric receptor.

9. The method according to claim 1, wherein an increase in the binding in the presence of said agent or sample relative to the binding in the absence of said agent or sample identifies said agent or sample as an agent or sample that increases the binding of the chimeric receptor.

10. The method according to claim 1, wherein a decrease in the binding in the presence of said agent or sample relative to the binding in the absence of said agent or sample identifies said agent or sample as an agent or a sample that decreases the binding of the chimeric receptor.

11. The method according to claim 1, wherein the one or more musk compound(s) is detectably labeled.

12. The method according to claim 1, wherein the contacting is performed in, or on a cell expressing said chimeric receptor.

13. The method according to claim 1, wherein the measuring is performed using a method selected from label displacement, surface plasmon resonance, fluorescence resonance energy transfer, fluorescence quenching, and fluorescence polarization.

14. The method according to claim 8, wherein the step of measuring a signaling activity of the chimeric receptor as defined herein comprises detecting a change in the level of a second messenger.

15. The method according to claim 8, wherein measuring the signaling activity comprises using a fluorescence or luminescence assay, or assay comprising an automated fluorometric or luminescent reader.

16. The method according to claim 8, wherein the one or more musk compound(s) is detectably labeled with a moiety selected from the group consisting of a radioisotope, a fluorophore, and a quencher of fluorescence.

17. The method according to claim 12, wherein said cell is selected from the group consisting of Human embryonic kidney cells (HEK293), Chinese hamster cells (CHO), Monkey cells (COS), primary olfactory cells, *Xenopus* cells, insect cells, yeast, and bacteria.

18. The method according to claim 15, wherein the fluorescence or luminescence assay comprises using $Ca^{2+}$ sensitive fluorophores selected from the group consisting of fluo3, Fluo4, Fura-2, Ca3 kit, Ca6 kit, and aequorin.

19. The method according to claim 15, wherein the assay comprising an automated fluorometric or luminescent reader is selected from the group consisting of Functional Drug Screening System (FDSS) and Fluorometric Imaging Plate Reader (FLIPR).

\* \* \* \* \*